United States Patent
Hilpert et al.

(10) Patent No.: US 9,988,390 B2
(45) Date of Patent: Jun. 5, 2018

(54) PYRIMIDONE DERIVATIVES AND THEIR USE IN THE TREATMENT, AMELIORATION OR PREVENTION OF A VIRAL DISEASE

(71) Applicant: F. Hoffmann-La Roche AG, Basel (CH)

(72) Inventors: Hans Hilpert, Basel (CH); Lukas Kreis, Basel (CH); Christian Lerner, Basel (CH); Roland Humm, Auggen (DE); Thorsten Muser, Lowrrach (DE); Bernd Kuhn, Reinach BL (CH)

( * ) Notice: Subject to any disclaimer, the term of this patent is extended or adjusted under 35 U.S.C. 154(b) by 0 days. days.

(21) Appl. No.: 15/337,367

(22) Filed: Oct. 28, 2016

(65) Prior Publication Data

US 2017/0267680 A1    Sep. 21, 2017

(30) Foreign Application Priority Data

Oct. 30, 2015 (EP) .................................. 15 19 2460
Mar. 14, 2016 (EP) .................................. 16 16 0213

(51) Int. Cl.
*C07D 487/04* (2006.01)

(52) U.S. Cl.
CPC .................................. *C07D 487/04* (2013.01)

(58) Field of Classification Search
CPC .................................................. C07D 487/04
See application file for complete search history.

(56) References Cited

FOREIGN PATENT DOCUMENTS

WO    2005/092099 A1    10/2005
WO    2014/108406 A1    7/2014

OTHER PUBLICATIONS

Jan. 4, 2017 International Search Report issued in International Application No. PCT/EP2016/076168.

Pflug, et al., "Structural insights into RNA synthesis by the influenza virus transcription-replication machine" Virus Research 234 (2017) 103-117.

Stevaert, et al., "The Influenza Virus Polymerase Complex: An Update on Its Structure, Functions, and Significance for Antiviral Drug Design" Medicinal Research Reviews, Oct. 2016, DOI: 10.1002/med.21401.

Jones, et al., "A novel endonuclease inhibitor exhibits broad-spectrum anti-influenza activity in vitro", Antimicrob. Agents Chemother, doi:10.1128/AAC.00868-16, 2016, American Society for Microbiology.

*Primary Examiner* — Bruck Kifle

(74) *Attorney, Agent, or Firm* — Mintz, Levin, Cohn, Ferris, Glovsky and Popeo, P.C.

(57) ABSTRACT

The present invention relates to compounds having the general formula (Ia) or (Ib), optionally in the form of a pharmaceutically acceptable salt, solvate, polymorph, codrug, cocrystal, prodrug, tautomer, racemate, enantiomer, or diastereomer or mixture thereof,

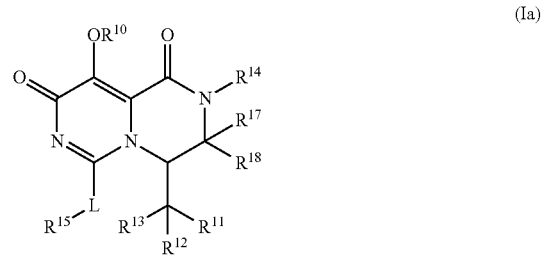

(Ia)

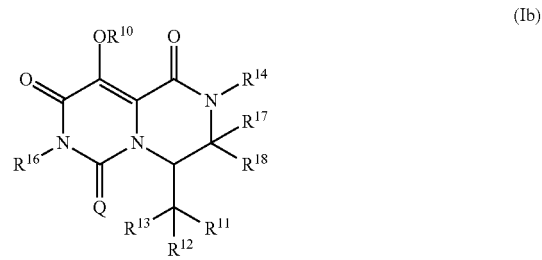

(Ib)

which are useful in treating, ameliorating or preventing a viral disease, in particular influenza.

9 Claims, No Drawings

PYRIMIDONE DERIVATIVES AND THEIR USE IN THE TREATMENT, AMELIORATION OR PREVENTION OF A VIRAL DISEASE

CROSS-REFERENCE TO RELATED APPLICATIONS

This application claims priority to and the benefit of European Patent Application No. 16 16 0213.1, filed Mar. 14, 2016, and European Patent Application No. 15 19 2460.2, filed Oct. 30, 2015, the disclosure of which is incorporated herein by reference in its entirety.

FIELD OF THE INVENTION

The present invention relates to compounds having the general formula (Ia) or (Ib), optionally in the form of a pharmaceutically acceptable salt, solvate, polymorph, codrug, cocrystal, prodrug, tautomer, racemate, enantiomer, or diastereomer or mixture thereof,

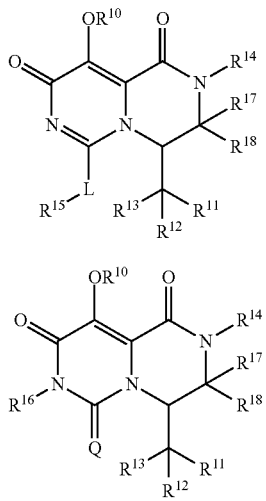

which are useful in treating, ameloriating or preventing a viral disease, in particular influenza.

BACKGROUND OF THE INVENTION

Influenza viruses belong to the Orthomyxoviridae family of RNA viruses. Based on antigenic differences of viral nucleocapsid and matrix proteins, influenza viruses are further divided into three types named influenza A, B, and C viruses. All influenza viruses have an envelope, and their genomes are composed of eight or seven single-stranded, negative-sensed RNA segments. These viruses cause respiratory diseases in humans and animals with a significant morbidity and mortality. The influenza pandemic of 1918, Spanish flu, is thought to have killed up to 100 million people. The reassortment of avian flu RNA fragments with circulating human viruses caused the other two pandemics in 1957 H2N2 "Asian influenza" and 1968 H3N2 "Hong Kong influenza". Now, people around the world face the challenges of influenza from various angles: seasonal influenza epidemics affect about 5-15% of the world's population with an annual mortality ranging from 250,000 to 500,000. Infections of avian flu strains, mostly H5N1, have been reported in many Asian countries. Although no frequent human-to-human spreading has been observed, avian flu infection is serious and associated with a high mortality of up to 60% of infected persons. In 2009, an H1N1 swine flu infection appeared initially in North America and evolved into a new pandemic. Currently, seasonal trivalent influenza vaccines and vaccines specific for H5N1 or swine flu are either available or in the phase of clinical trials. The prophylaxis is an effective method, at least in some populations, for preventing influenza virus infection and its potentially severe complications. However, continuous viral antigenicity shifting and drafting makes future circulating flu strains unpredictable. Furthermore, due to the limitations of mass production of vaccines within a relatively short period of time during a pandemic, other anti-flu approaches such as anti-flu drugs are highly desirable. On the market, there are two types of anti-flu drugs available: neuraminidase inhibitors such as oseltamivir phosphate (Tamilflu) and zanamivir (Relenza); and M2 ion channel blockers such as amantadine and rimantadine. To increase the effectiveness of current anti-flu drugs and prevent or attenuate appearance of drug-resistant viruses, it is invaluable to discover compounds with new mechanisms of anti-influenza action that can be used as a therapeutic or prophylactic agent alone or combined with current anti-flu drugs.

It appears realistic that H5N1 and related highly pathogenic avian influenza viruses could acquire mutations rendering them more easily transmissible between humans. In addition, the new A/H1N1 could become more virulent and only a single point mutation would be enough to confer resistance to oseltamivir (Neumann et al., Nature 2009, 18, 459(7249), 931-939). This has already happened in the case of some seasonal H1N1 strains which have recently been identified (Dharan et al., The Journal of the American Medical Association, 2009, 301(10), 1034-1041; Moscona et al., The New England Journal of Medicine 2009, 360(10), 953-956). The unavoidable delay in generating and deploying a vaccine could in such cases be catastrophically costly in human lives and societal disruption.

In view of the currently elevated risk of infections of pandemic H1N1 swine flu, highly pathogenic H5N1 avian flu, and drug-resistant seasonal flu, the development of new anti-influenza drugs has again become high priority.

In many cases, the development of anti-viral medicament may be facilitated by the availability of structural data of viral proteins. The availability of structural data of influenza virus surface antigen neuraminidase has, e.g. led to the design of improved neuraminidase inhibitors (Von Itzstein et al., Nature 1993, 363, 418-423). Examples of active compounds which have been developed based on such structural data include zanamivir (Glaxo) and oseltamivir (Roche). However, although these medicaments may lead to a reduction of the duration of the disease, there remains an urgent need for improved medicaments which may also be used for curing these diseases.

Adamantane-containing compounds such as amantadine and rimantadine are another example of active compounds which have been used in order to treat influenza. However, they often lead to side effects and have been found to be ineffective in a growing number of cases (Magden et al., Appl. Microbiol. Biotechnol. 2005, 66, 612-621).

More unspecific viral drugs have been used for the treatment of influenza and other virus infections (Eriksson et al., Antimicrob. Agents Chemother. 1977, 11, 946-951), but their use is limited due to side effects (Furuta et al., Antimicrobial Agents and Chemotherapy 2005, 981-986).

Influenza viruses being Orthomyxoviridae, as described above, are negative-sense ssRNA viruses. Other examples of viruses of this group include Arenaviridae, Bunyaviridae, Ophioviridae, Deltavirus, Bornaviridae, Filoviridae, Paramyxoviridae, Rhabdoviridae and Nyamiviridae. These viruses use negative-sense RNA as their genetic material. Single-stranded RNA viruses are classified as positive or negative depending on the sense or polarity of the RNA. Before transcription, the action of an RNA polymerase is necessary to produce positive RNA from the negative viral RNA. The RNA of a negative-sense virus alone is therefore considered non-infectious.

The trimeric viral RNA-dependent RNA polymerase, consisting of polymerase basic protein 1 (PB1), polymerase basic protein 2 (PB2) and polymerase acidic protein (PA) subunits, is responsible for the transcription and replication of the viral RNA genome segments. Structural data of the two key domains of the polymerase, the mRNA cap-binding domain in the PB2 subunit (Guilligay et al., Nature Structural & Molecular Biology 2008, 15(5), 500-506) and the endonuclease-active site in the PA subunit (Dias et al., Nature 2009, 458, 914-918) has become available.

The ribonucleoprotein represents the minimal transcriptional and replicative machinery of an influenza virus. During transcription, the viral RNA polymerase synthesizes capped and polyadenylated mRNA using 5' capped RNA primers. During replication, the viral RNA polymerase generates a complementary RNA (cRNA) replication intermediate, a full-length complement of the vRNA that serves as a template for the synthesis of new copies of vRNA. The nucleoprotein is also an essential component of the viral transcriptional machinery. The polymerase complex which is responsible for transcribing the single-stranded negative-sense viral RNA into viral mRNAs and for replicating the viral mRNAs, is thus a promising starting points for developing new classes of compounds which may be used in order to treat influenza (Fodor, Acta virologica 2013, 57, 113-122). This finding is augmented by the fact that the polymerase complex contains a number of functional active sites which are expected to differ to a considerable degree from functional sites present in proteins of cells functioning as hosts for the virus (Magden et al., Appl. Microbiol. Biotechnol. 2005, 66, 612-621). As one example, a substituted 2,6-diketopiperazine has been identified which selectively inhibits the cap-dependent transcriptase of influenza A and B viruses without having an effect on the activities of other polymerases (Tomassini et al., Antimicrob. Agents Chemother. 1996, 40, 1189-1193). In addition, it has been reported that phosphorylated 2'-deoxy-2'-fluoroguanosine reversibly inhibits influenza virus replication in chick embryo cells. While primary and secondary transcription of influenza virus RNA were blocked even at low concentrations of the compound, no inhibition of cell protein synthesis was observed even at high compound concentrations (Tisdale et al., Antimicrob. Agents Chemother. 1995, 39, 2454-2458).

WO 2005/087766 discloses certain pyridopyrazine- and pyrimidopyrazine-dione compounds which are stated to be inhibitors of HIV integrase and inhibitors of HIV replication. The compounds are described as being useful in the prevention and treatment of infection caused by HIV and in the prevention, delay in the onset, and treatment of AIDS.

WO 2010/147068 also discloses compounds which allegedly have antiviral activities, especially inhibiting activity for influenza viruses.

WO 2012/039414 relates to compounds which are described as having antiviral effects, particularly having growth inhibitory activity on influenza viruses.

WO 2014/108406 discloses certain pyrimidone derivatives and their use in the treatment, amelioration or prevention of a viral disease.

It is an object of the present invention to identify further compounds which are effective against viral diseases and which have improved pharmacological properties.

SUMMARY OF THE INVENTION

Accordingly, in a first embodiment, the present invention provides compounds having the general formulae (Ia) and (Ib).

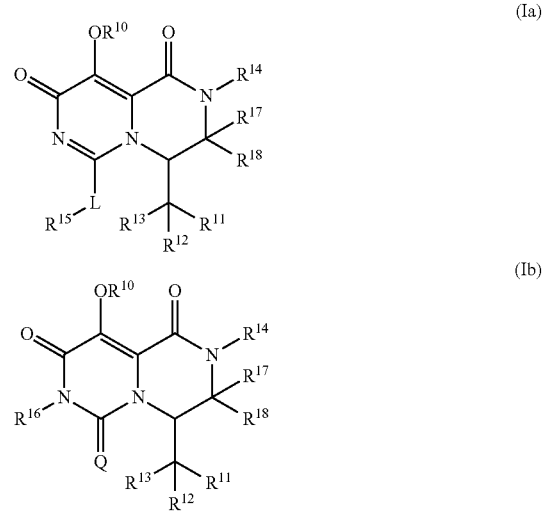

It is understood that throughout the present specification the term "a compound having the general formula (Ia) or (Ib)" encompasses pharmaceutically acceptable salts, solvates, polymorphs, prodrugs, codrugs, cocrystals, tautomers, racemates, enantiomers, or diastereomers or mixtures thereof unless mentioned otherwise.

A further embodiment of the present invention relates to a pharmaceutical composition comprising a compound having the general formula (Ia) or (Ib) and optionally one or more pharmaceutically acceptable excipient(s) and/or carrier(s).

The compounds having the general formula (Ia) and (Ib) are useful for treating, ameliorating or preventing viral diseases.

It has been surprisingly found that the compounds according to the present invention have improved pharmcological properties.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which is limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

The term "alkyl" refers to a saturated straight or branched carbon chain.

The term "alkenyl" refers to a straight or branched carbon chain which contains at least one C=C double bond. The double bond may be at an end of the carbon chain or within the carbon chain.

The term "cycloalkyl" represents a cyclic version of "alkyl". The term "cycloalkyl" is also meant to include bicyclic, tricyclic and polycyclic versions thereof. Unless specified otherwise, the cycloalkyl group can have 3 to 12 carbon atoms.

"Hal" or "halogen" represents F, Cl, Br and I.

"3- to 7-membered carbo- or heterocyclic ring" refers to a three-, four-, five-, six- or seven-membered ring wherein none, one or more of the carbon atoms in the ring have been replaced by 1 or 2 (for the three-membered ring), 1, 2 or 3 (for the four-membered ring), 1, 2, 3, or 4 (for the five-membered ring) or 1, 2, 3, 4, or 5 (for the six-membered ring) and 1, 2, 3, 4, 5 or 6 (for the seven-membered ring) of the same or different heteroatoms, wherein the heteroatoms are selected from O, N and S.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl, preferably phenyl.

The term "heteroaryl" preferably refers to a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from O, N and S. Examples of the heteroaryl group include pyrrole, pyrrolidine, oxolane, furan, imidazolidine, imidazole, triazole, tetrazole, pyrazole, oxazolidine, oxazole, thiazole, piperidine, pyridine, morpholine, piperazine, and dioxolane.

The term "hydrocarbon group which contains from 5 to 20 carbon atoms and optionally 1 to 4 heteroatoms selected from O, N and S" refers to any group having 5 to 20 carbon atoms and optionally 1 to 4 heteroatoms selected from O, N and S. The term is also meant to include bicyclic, tricyclic and polycyclic versions thereof. If more than one ring is present, they can be separate from each other or be annelated.

The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —$(CH_2)_p$— with p=1 to 6). Examples of these groups include -(optionally substituted $C_{3-7}$ cycloalkyl), -(optionally substituted aryl) wherein the aryl group can be, for example, phenyl, -(optionally substituted biphenyl), adamantyl, —($C_{3-7}$ cycloalkyl)-aryl as well as the corresponding compounds with a linker.

If a compound or moiety is referred to as being "optionally substituted", it can in each instance include 1 or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counter anions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichiometric ratio of a target molecule or ion (i.e., compound of the present invention) and one or more neutral molecular cocrystal formers. A detailed discussion can be found, for example, in Ning Shan et al., Drug Discovery Today 2008, 13(9/10), 440-446 and in Good et al., Cryst. Growth Des. 2009, 9(5), 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups as well as the groups disclosed in Prog. Med. 5: 2157-2161 (1985) and provided by The British Library—"The world's Knowledge". Preferred examples of the prodrug include compounds in which $R^{10}$ is replaced by $P(O)(O)OR^{19}$; $C(O)OR^{19}$; $C(O)R^{19}$; $C(R)_2$—$R^{19}$ or $R^{19}$; wherein $R^{19}$ is selected from $C_{5-10}$ aryl, $C_{1-6}$ alkylene-$C_{5-10}$ aryl, $C_{1-6}$ alkyl, $C_{1-6}$ alkylene(-O—$C_{1-6}$ alkyl)$_n$ (with n=1 to 30), $C_{1-6}$ alkylene-C(O)OR, $C_{5-10}$ arylene-C(O)OR, $C_{1-6}$ alkylene-O—C(O)OR and $C_{1-6}$ alkylene-O—C(O)R. The group R is H or $C_{1-6}$ alkyl.

In the prodrugs of the present invention, the "$R^{10}$" group in —$OR^{10}$ may be a group converted into an —OH group in vivo. Preferably the groups selected from various substituted carbonyl groups, substituted lower alkyl oxy groups (e.g., substituted oxymethyl), optionally substituted cyclic group lower alkyl (e.g., optionally substituted cyclic methyl group), and optionally substituted imino lower alkyl (e.g., optionally substituted imino methyl) are exemplified, and examples preferably include a group selected from the following formulae a) to y).

a) —C(=O)—$R^{10a}$,
b) —C(=O)—$R^{10b}$,
c) —C(=O)-L'-$R^{10b}$,
d) —C(=O)-L'-O—$R^{10b}$,
e) —C(=O)-L'-O-L'-O—$R^{10b}$,
f) —C(=O)-L'-O—C(=O)—$R^{10b}$,
g) —C(=O)—O—$R^{10c}$,
h) —C(=O)—N($R^{10c}$)$_2$,
i) —C(=O)—O-L'-O—$R^{10c}$,
j) —CH$_2$—$R^{10d}$,
k) —CH$_2$—O-L'-O—$R^{10d}$,
l) —CH$_2$—O—C(=O)—$R^{10d}$,
m) —CH$_2$—O—C(=O)—O—$R^{10d}$,
n) —CH(—CH$_3$)—O—C(=O)—O—$R^{10d}$,
o) —CH$_2$—O—C(=O)—N(—K)—$R^{10d}$,
p) —CH$_2$—O—C(=O)—O-L'-O—$R^{10d}$,
q) —CH$_2$—O—C(=O)—O-L'—N($R^{10d}$)$_2$,
r) —CH$_2$—O—C(=O)—N(—K)-L'—O—$R^{10d}$,
s) —CH$_2$—O—C(=O)—N(—K)-L'-N($R^{10d}$)$_2$,
t) —CH$_2$—O—C(=O)—O-L'-O-L'-O—$R^{10d}$,
u) —CH$_2$—O—C(=O)—O-L'-N(—K)—C(=O)—$R^{10d}$,
v) —CH$_2$—O—P(=O)(—OH)$_2$,
w) —CH$_2$—O—P(=O)(—OBn)$_2$,
x) —CH$_2$—$R^{10e}$,
y) —C(=N$^+$$R^{10f}$$_2$)(—N$R^{10f}$$_2$)

wherein
L' is straight or branched lower alkylene,
K is hydrogen, or straight or branched lower alkylene, or straight or branched lower alkenylene,
$R^{10a}$ is lower alkyl optionally substituted with one or more $R^{10g}$, or lower alkenyl optionally substituted with one or more $R^{10g}$,
$R^{10b}$ is a carbocyclic group optionally substituted with one or more $R^{10g}$, a heterocyclic group optionally substituted with one or more $R^{10g}$, lower alkyl amino optionally substituted with one or more $R^{10g}$, or lower alkylthio optionally substituted with one or more $R^{10g}$,
$R^{10c}$ is lower alkyl optionally substituted with one or more $R^{10g}$, a carbocyclic group optionally substituted with one or more $R^{10g}$, or a heterocyclic group optionally substituted with one or more $R^{10g}$
$R^{10d}$ is lower alkyl optionally substituted with one or more $R^{10g}$, a carbocyclic group optionally substituted with one or more $R^{10g}$, a heterocyclic group optionally substituted with one or more $R^{10g}$, lower alkyl amino optionally substituted with one or more $R^{10g}$, carbocycle lower alkyl optionally substituted with one or more $R^{10g}$, heterocycle lower alkyl optionally substituted with one or more $R^{10g}$, or lower alkylsilyl,
$R^{10e}$ is carbocyclic group optionally substituted with one or more $R^{10g}$, or heterocyclic group optionally substituted with one or more $R^{10g}$, and
$R^{10f}$ is lower alkyl optionally substituted with one or more $R^{10g}$,
$R^{10g}$ is selected from oxo, lower alkyl, hydroxy lower alkyl, amino, lower alkylamino, carbocycle lower alkyl, lower alkylcarbonyl, halogen, hydroxy, carboxy, lower alkylcarbonylamino, lower alkylcarbonyloxy, lower alkyloxycarbonyl, lower alkyloxy, cyano, and nitro.

In the above definitions of $R^{10a}$ to $R^{10g}$, the term "lower" refers to $C_{1-7}$, except for lower alkenyl and alkenylene, where it refers to $C_{2-7}$.

As the group to form a prodrug, the "$R^{10}$" group in —$OR^{10}$ group in the formula (I) is preferably a group selected from the following b), l), m), and n).

b) —C(=O)—$R^{10b}$,
l) —CH$_2$—O—C(=O)—$R^{10d}$,
m) —CH$_2$—O—C(=O)—O—$R^{10d}$,
n) —CH(—CH$_3$)—O—C(=O)—O—$R^{10d}$
wherein each symbol is as defined above.

As used herein, the abbreviation Boc refers to t-butyloxycarbonyl, and the abbreviation Z refers to benzyloxycarbonyl.

Compounds Having the General Formulae (Ia) and (Ib)

The present invention provides compounds having the formulae (Ia) and (Ib):

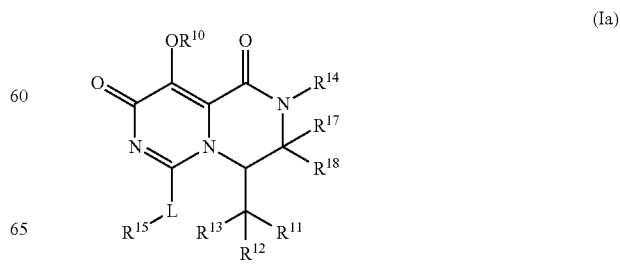

(Ia)

-continued

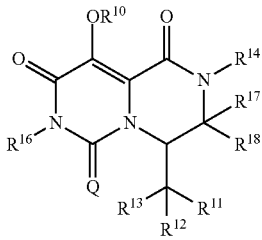

(Ib)

The present invention provides a compound having the general formula (I) in which the following definitions apply.

L is selected from $NR^L$, $N(R^L)C(O)$, $N(R^L)C(O)O$, $N(R^L)C(=NR^L)NR^L$, $C(O)N(R^L)$, $SO_2N(R^L)$, $N(R^L)SO_2$, O, C(O)O, OC(O), $OSO_2$, S, SO, $SO_2$ and a bond. L is preferably selected from $N(R^L)C(O)$, $C(O)N(R^L)$, $SO_2N(R^L)$, $N(R^L)SO_2O$, C(O)O, OC(O), $OSO_2S$, SO and $SO_2$. More preferably, L is selected from $NR^L$, $N(R^L)C(O)$, $C(O)N(R^L)$, $SO_2N(R^L)$, $N(R^L)SO_2$, O, S, SO and $SO_2$. Still more preferably, L is selected from $NR^L$, $N(R^L)C(O)$, $C(O)N(R^L)$, O, S, SO and $SO_2$. Still more preferably, L is selected from NHC(O), C(O)NH, O, S, SO and $SO_2$. Most preferably, L is selected from NHC(O), O, S, SO and $SO_2$. In another embodiment, L is preferably selected from O, S, SO, $SO_2$ and a bond.

$R^L$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) or —$C_{1-4}$ alkyl-(optionally substituted aryl). Preferably $R^L$ is —H, -(optionally substituted $C_{1-6}$ alkyl), -(optionally substituted $C_{3-7}$ cycloalkyl) or -(optionally substituted aryl). More preferably, $R^L$ is —H, -(optionally substituted $C_{1-6}$ alkyl) or -(optionally substituted $C_{3-7}$ cycloalkyl). Even more preferably, $R^L$ is —H or -(optionally substituted $C_{1-6}$ alkyl). Still more preferably, $R^L$ is —H or -(optionally substituted $C_{1-4}$ alkyl). Still more preferably, $R^L$ is —H.

L is selected from $NR^L$, $N(R^L)C(O)$, $N(R^L)C(O)O$, $N(R^L)C(=NR^L)NR^L$, $C(O)N(R^L)$, $SO_2N(R^L)$, $N(R^L)SO_2$, O, C(O)O, OC(O), $OSO_2$, S, SO, $SO_2$ and a bond; wherein $R^L$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) or —$C_{1-4}$ alkyl-(optionally substituted aryl). L is preferably selected from $NR^L$, $N(R^L)C(O)$, $C(O)N(R^L)$, $SO_2N(R^L)$, $N(R^L)SO_2O$, C(O)O, OC(O), $OSO_2$, S, SO and $SO_2$; wherein $R^L$ is —H, -(optionally substituted $C_{1-6}$ alkyl), -(optionally substituted $C_{3-7}$ cycloalkyl) or -(optionally substituted aryl). More preferably, L is selected from $NR^L$, $N(R^L)C(O)$, $C(O)N(R^L)$, $SO_2N(R^L)$, $N(R^L)SO_2O$, C(O)O, OC(O), $OSO_2$, S, SO and $SO_2$; wherein $R^L$ is —H, -(optionally substituted $C_{1-6}$ alkyl) or -(optionally substituted $C_{3-7}$ cycloalkyl). Even more preferably, L is selected from $NR^L$, $N(R^L)C(O)$, $C(O)N(R^L)$, $SO_2N(R^L)$, $N(R^L)SO_2$, O, S, SO and $SO_2$; wherein $R^L$ is —H or -(optionally substituted $C_{1-6}$ alkyl). Still more preferably, L is selected from $NR^L$, $N(R^L)C(O)$, $C(O)N(R^L)$, O, S, SO and $SO_2$; wherein $R^L$ is —H or -(optionally substituted $C_{1-4}$ alkyl). Still more preferably, L is selected from $NR^L$, $N(R^L)C(O)$, $C(O)N(R^L)$, and O; wherein $R^L$ is —H. Still more preferably, L is selected from $N(R^L)C(O)$, $C(O)N(R^L)$ and O. In another embodiment, L is more preferably selected from O, S, SO and $SO_2$. Still more preferably, L is O.

In all embodiments, it is furthermore preferred, that in the case where L is NH, $R^{15}$ is not hydrogen.

Q is selected from $NR^Q$, O and S. Preferably, Q is selected from O and S. Most preferably, Q is O.

$R^Q$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) or —$C_{1-4}$ alkyl-(optionally substituted aryl). Preferably $R^Q$ is —H, -(optionally substituted $C_{1-6}$ alkyl) or -(optionally substituted $C_{3-7}$ cycloalkyl). More preferably, $R^Q$ is —H or -(optionally substituted $C_{1-4}$ alkyl). Even more preferably, $R^Q$ is —H.

Q is selected from $NR^Q$, O and S; wherein $R^Q$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) or —$C_{1-4}$ alkyl-(optionally substituted aryl). Q is preferably selected from $NR^Q$, O and S; wherein $R^Q$ is —H, -(optionally substituted $C_{1-6}$ alkyl) or -(optionally substituted $C_{3-7}$ cycloalkyl). More preferably, Q is selected from $NR^Q$, O and S; wherein $R^Q$ is —H or -(optionally substituted $C_{1-4}$ alkyl). Even more preferably, Q is selected from $NR^Q$, O and S; wherein $R^Q$ is —H. Still more preferably, Q is selected from O and S. Most preferably, Q is O.

$R^{10}$ is —H, -(optionally substituted $C_{1-6}$ alkyl group) or —C(O)-(optionally substituted $C_{1-6}$ alkyl group). $R^{10}$ is preferably —H, —C(O)—$C_{1-6}$ alkyl group, wherein the alkyl group can be optionally substituted by one or more halogen atoms, or a —$C_{1-6}$ alkyl group which may optionally be substituted by one or more halogen atoms. More preferably, $R^{10}$ is —H, —$C_{1-6}$ alkyl group or —C(O)—$C_{1-6}$ alkyl group. Even more preferably $R^{10}$ is —H or —$C_{1-6}$ alkyl group. Most preferably, $R^{10}$ is —H.

$R^{11}$ is —H, a —$C_{1-6}$ alkyl group, or a —$C_{1-6}$ alkyl group which is substituted by one or more halogen atoms. $R^1$ is preferably —H, a —$C_{1-4}$ alkyl group, or a —$C_{1-4}$ alkyl group which is substituted by one or more halogen atoms. More preferably, $R^1$ is —H or a —$C_{1-4}$ alkyl group. Most preferably, $R^{11}$ is —H.

$R^{12}$ is selected from -(optionally substituted hydrocarbon group which contains from 5 to 20 carbon atoms and optionally 1 to 4 heteroatoms selected from O, N and S). $R^{12}$ is preferably selected from -(optionally substituted hydrocarbon group which contains from 5 to 10 carbon atoms and optionally 1 to 4 heteroatoms selected from O, N and S). More preferably, $R^{12}$ is selected from -(optionally substituted aryl or heteroaryl group which contains from 5 to 10 carbon atoms and optionally 1 to 4 heteroatoms selected from O, N and S). Still more preferably, $R^{12}$ is selected from -(aryl which contains 6 to 10 carbon atoms and is optionally substituted with one or more selected from halogen and $C_{1-4}$-alkyl). Still more preferably, $R^{12}$ is selected from -(phenyl which is optionally substituted with one or more selected from halogen and $C_{1-4}$-alkyl).

$R^{13}$ is -(optionally substituted hydrocarbon group which contains from 5 to 20 carbon atoms and optionally 1 to 4 heteroatoms selected from O, N and S and which contains at least one ring). Preferably, the at least one ring is aromatic such as an aryl or heteroaryl ring. More preferably, $R^{13}$ is a hydrocarbon group which contains from 5 to 20 carbon atoms and optionally 1 to 4 heteroatoms and which contains at least two rings, wherein the hydrocarbon group can be optionally substituted. Still more preferably, $R^{13}$ is selected from -(aryl which contains 6 to 10 carbon atoms and is optionally substituted with one or more selected from halogen and $C_{1-4}$-alkyl). Still more preferably, $R^{13}$ is selected from -(phenyl which is optionally substituted with one or more selected from halogen and $C_{1-4}$-alkyl).

In another embodiment, $R^{12}$ and $R^{13}$ are optionally joined together to form an -(optionally substituted hydrocarbon group which contains from 5 to 20 carbon atoms and optionally 1 to 4 heteroatoms selected from O, N and S and which contains at least one ring). In this embodiment, the group formed by joining together $R^{12}$ and $R^{13}$ preferably contains at least two carbo- or heterocyclic rings which are connected to each other via a linking group $R^c$ which is selected from a bond, —$CH_2$—, —C(O)—, —O—, —S—, —S(O)—, —N(H)—, —N(optionally substituted $C_{1-6}$ alkyl)-, —N(optionally substituted aryl)-, —C(O)NH—, —$CH_2$—$CH_2$—, —$CH_2$—O—, —$CH_2$—S—, —$CH_2$—N(H)—, —$CH_2$—N(optionally substituted $C_{1-6}$ alkyl)-, —$CH_2$—N(optionally substituted aryl)-, —$CH_2$—C(O)NH—, —$CH_2$—O—$CH_2$—, —$CH_2$—S—$CH_2$—, —$CH_2$—N(H)—$CH_2$—, —$CH_2$—N(optionally substituted $C_{1-6}$ alkyl)-$CH_2$—, —$CH_2$—N(optionally substituted aryl)-$CH_2$—, —$CH_2$—C(O)NH—$CH_2$— and —O—$CH_2$—O—. In a preferred embodiment, the linking group $R^c$ is selected from —$CH_2$—$CH_2$—, —$CH_2$—O—, —$CH_2$—S—, —$CH_2$—N(H)—, —$CH_2$—C(O)NH—, —$CH_2$—N(optionally substituted $C_{1-6}$ alkyl)- and —$CH_2$—N(optionally substituted aryl)-. Even more preferably, the linking group $R^c$ is selected from —$CH_2$—$CH_2$—, —$CH_2$—O— and —$CH_2$—S—.

Specific examples of the moiety

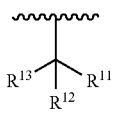

include

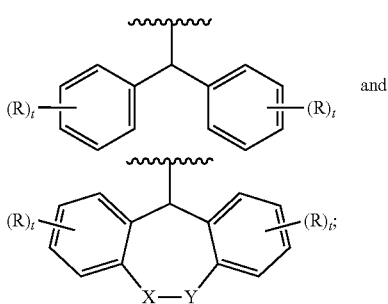

wherein
—X—Y— corresponds to the linking group $R^c$.
X is absent, $CH_2$, NH, C(O)NH, S or O.
Y is $CH_2$.
Specific examples of X—Y include —$CH_2$—$CH_2$—, —$CH_2$—O— and —$CH_2$—S—.
R is independently selected from —H, —$C_{1-6}$ alkyl, —$CF_3$, -halogen, —CN, —OH, and —O—$C_{1-6}$ alkyl, preferably —H or -halogen.
t is 1 to 5, preferably 1 to 3.
$R^{14}$ is —H, -(optionally substituted $C_{1-6}$ alkyl), -(optionally substituted $C_{3-7}$ cycloalkyl), -(optionally substituted aryl), -(optionally substituted heterocycloalkyl), -(optionally substituted heteroaryl), —$C_{1-4}$ alkyl-(optionally substituted $C_{3-7}$ cycloalkyl), —$C_{1-4}$ alkyl-(optionally substituted aryl), —$C_{1-4}$ alkyl-(optionally substituted heterocycloalkyl), or —$C_{1-4}$ alkyl-(optionally substituted heteroaryl). $R^{14}$ is preferably -(optionally substituted $C_{1-6}$ alkyl). $R^{14}$ is more preferably selected from —$CH_3$, $CH(CH_3)_2$ and $CH(CH_3)(CF_3)$.

$R^{15}$ is selected from —H, —CN, -(optionally substituted $C_{1-6}$ alkyl), -(optionally substituted $C_{2-6}$ alkenyl), -(optionally substituted $C_{3-7}$ cycloalkyl), -(optionally substituted aryl), -(optionally substituted heteroaryl), —$C_{1-4}$ alkyl-(optionally substituted $C_{3-7}$ cycloalkyl), —$C_{1-4}$ alkyl-(optionally substituted aryl) and —$C_{1-4}$ alkyl-(optionally substituted heteroaryl). Preferably, $R^{15}$ is selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) and —$C_{1-4}$ alkyl-(optionally substituted aryl). More preferably, $R^{15}$ is selected from —H, -(optionally substituted $C_{1-6}$ alkyl), -(optionally substituted aryl), —$C_{1-4}$ alkyl-(optionally substituted $C_{3-7}$ cycloalkyl) and —$C_{1-4}$ alkyl-(optionally substituted aryl). Even more preferably, $R^{15}$ is selected from —H, -(optionally substituted $C_{1-6}$ alkyl), —$C_{1-4}$ alkyl-(optionally substituted $C_{3-7}$ cycloalkyl) and —$C_{1-4}$ alkyl-(optionally substituted aryl). Still more preferably, $R^{15}$ is selected from —H, -(optionally substituted $C_{1-6}$ alkyl) and —$C_{1-4}$ alkyl-(optionally substituted aryl). Still more preferably, $R^{15}$ is selected from —H, -(optionally substituted $C_{1-6}$ alkyl) and —$C_{1-4}$ alkyl-($C_{6-10}$ aryl optionally substituted with one or more selected from —O—$C_{1-4}$ alkyl, halogen and —$C_{1-4}$ alkyl). Still more preferably, $R^{15}$ is selected from —H, -(optionally substituted $C_{1-6}$ alkyl) and —$CH_2$-(phenyl optionally substituted with one or more selected from —O—$C_{1-4}$ alkyl, halogen and —$C_{1-4}$ alkyl). Still more preferably, $R^{15}$ is -(optionally substituted $C_{1-4}$ alkyl). Most preferably, $R^{15}$ is methyl or ethyl.

$R^{16}$ is selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) and —$C_{1-4}$ alkyl-(optionally substituted aryl). $R^{16}$ is preferably selected from —H, -(optionally substituted $C_{1-6}$ alkyl), -(optionally substituted aryl), —$C_{1-4}$ alkyl-(optionally substituted $C_{3-7}$ cycloalkyl) and —$C_{1-4}$ alkyl-(optionally substituted aryl). More preferably, $R^{16}$ is selected from —H, -(optionally substituted $C_{1-6}$ alkyl), —$C_{1-4}$ alkyl-(optionally substituted $C_{3-7}$ cycloalkyl) and —$C_{1-4}$ alkyl-(optionally substituted aryl). Even more preferably, $R^{16}$ is selected from —H, -(optionally substituted $C_{1-6}$ alkyl) and —$C_{1-4}$ alkyl-(optionally substituted aryl). Still more preferably, $R^{16}$ is selected from —H, -(optionally substituted $C_{1-6}$ alkyl) and —$C_{1-4}$ alkyl-($C_{6-10}$ aryl optionally substituted with one or more selected from —O—$C_{1-4}$ alkyl, halogen and —$C_{1-4}$ alkyl). Still more preferably, $R^{16}$ is selected from —H, -(optionally substituted $C_{1-6}$ alkyl) and —$CH_2$-(phenyl optionally substituted with one or more selected from —O—$C_{1-4}$ alkyl, halogen and —$C_{1-4}$ alkyl). Still more preferably, $R^{16}$ is selected from —H, -(optionally substituted $C_{1-4}$ alkyl) and —$CH_2$-(phenyl optionally substituted with —O—$C_{1-4}$ alkyl). Still more preferably, $R^{16}$ is selected from —H and -(optionally substituted $C_{1-4}$ alkyl). Still more preferably, $R^{16}$ is -(optionally substituted $C_{1-4}$ alkyl). Most preferably, $R^{16}$ is methyl or ethyl.

$R^{17}$ is selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) and —$C_{1-4}$ alkyl-(optionally substituted aryl). $R^{17}$ is preferably selected from —H, -(optionally substituted $C_{1-6}$ alkyl), -(optionally substituted $C_{3-7}$ cycloalkyl), -(optionally substituted aryl) and —$C_{1-4}$ alkyl-(optionally substituted aryl). More preferably, $R^{17}$ is selected from —H, -(optionally substituted $C_{1-6}$ alkyl), -(optionally substituted $C_{3-7}$ cycloalkyl) and -(optionally substituted aryl). Even more preferably, $R^{17}$ is selected from —H, -(optionally substituted $C_{1-6}$ alkyl), -(optionally substituted $C_{3-7}$ cycloalkyl) and -(optionally substituted $C_{6-10}$ aryl). Still more preferably, $R^{17}$ is selected from —H, -(optionally substituted $C_{1-6}$ alkyl), -(optionally substituted $C_{3-7}$ cycloalkyl) and -(optionally substituted phenyl). Still more preferably, $R^{17}$ is selected from —H, -(optionally substituted $C_{1-6}$ alkyl) and -(optionally substituted $C_{3-7}$ cycloalkyl). Still more preferably, $R^{17}$ is selected from —H and -(optionally substituted $C_{1-4}$ alkyl). Still more preferably, $R^{17}$ is selected from —H and —($C_{1-4}$ alkyl optionally substituted with one or more halogen).

$R^{18}$ is selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) and —$C_{1-4}$ alkyl-(optionally substituted aryl). $R^{18}$ is preferably selected from —H, -(optionally substituted $C_{1-6}$ alkyl), -(optionally substituted $C_{3-7}$ cycloalkyl), -(optionally substituted aryl) and —$C_{1-4}$ alkyl-(optionally substituted aryl). More preferably, $R^{18}$ is selected from —H, -(optionally substituted $C_{1-6}$ alkyl), -(optionally substituted $C_{3-7}$ cycloalkyl) and -(optionally substituted aryl). Even more preferably, $R^{18}$ is selected from —H, -(optionally substituted $C_{1-6}$ alkyl), -(optionally substituted $C_{3-7}$ cycloalkyl) and -(optionally substituted $C_{6-10}$ aryl). Still more preferably, $R^{18}$ is selected from —H, -(optionally substituted $C_{1-6}$ alkyl), -(optionally substituted $C_{3-7}$ cycloalkyl) and -(optionally substituted phenyl). Still more preferably, $R^{18}$ is selected from —H, -(optionally substituted $C_{1-6}$ alkyl) and -(optionally substituted $C_{3-7}$ cycloalkyl). Still more preferably, $R^{18}$ is selected from —H and -(optionally substituted $C_{1-6}$ alkyl). Still more preferably, $R^{18}$ is selected from —H and -(optionally substituted $C_{1-4}$ alkyl). Still more preferably, $R^{18}$ is selected from —H and —($C_{1-4}$ alkyl optionally substituted with one or more halogen).

It is preferred that at least one of $R^{17}$ and $R^{18}$ be —H. More preferably, both $R^{17}$ and $R^{18}$ are —H.

The optional substituent(s) of the optionally substituted alkyl group is one or more substituents $R^a$, wherein each $R^a$ is independently selected from —C(O)—$C_{1-6}$ alkyl, -Hal, —$CF_3$, —CN, —COOR*, —OR*, —$(CH_2)_q NR*R**$, —C(O)—NR*R** and —NR*—C(O)—$C_{1-6}$ alkyl; Still more preferably, each $R^a$ is selected from —$C_{1-6}$ alkyl, —C(O)—$C_{1-6}$ alkyl, -Hal, —$CF_3$, —CN and —OR*. Still more preferably, each $R^a$ is selected from —$C_{1-4}$ alkyl, -Hal, —$CF_3$, —CN and —OMe. Still more preferably, each $R^a$ is selected from —$C_{1-4}$ alkyl, -Hal and —$CF_3$.

The optional substituent(s) of the optionally substituted cycloalkyl group, optionally substituted alkenyl group, optionally substituted heterocycloalkyl group, optionally substituted aryl group, optionally substituted heteroaryl group is one or more substituents $R^b$, wherein each $R^b$ is independently selected from —$C_{1-6}$ alkyl, —C(O)—$C_{1-6}$ alkyl, -Hal, —$CF_3$, —CN, —COOR*, —OR*, —$(CH_2)_q$ NR*R**, —C(O)—NR*R** and —NR*—C(O)—$C_{1-6}$ alkyl; Still more preferably, each $R^b$ is selected from —$C_{1-6}$ alkyl, —C(O)—$C_{1-6}$ alkyl, -Hal, —$CF_3$, —CN and —OR*. Still more preferably, each $R^b$ is selected from —$C_{1-4}$ alkyl, -Hal, —$CF_3$, —CN and —OMe. Still more preferably, each $R^b$ is selected from —$C_{1-4}$ alkyl, -Hal and —$CF_3$.

The optional substituent(s) of the optionally substituted hydrocarbon group is one or more substituents $R^d$, wherein each $R^d$ is independently selected from —$C_{1-6}$ alkyl, —C(O)—$C_{1-6}$ alkyl, -Hal, —$CF_3$, —CN, —COOR*, —OR*, —$(CH_2)_q NR*R**$, —C(O)—NR*R** and —NR*—C(O)—$C_{1-6}$ alkyl; Still more preferably, each $R^d$ is selected from —$C_{1-6}$ alkyl, —C(O)—$C_{1-6}$ alkyl, -Hal, —$CF_3$, —CN and —OR*. Still more preferably, each $R^d$ is selected from —$C_{1-4}$ alkyl, -Hal, —$CF_3$, —CN and —OMe. Still more preferably, each $R^d$ is selected from —$C_{1-4}$ alkyl, -Hal and —$CF_3$.

Each R is —H, or —$C_{1-6}$ alkyl. Still more preferably, each R is —H.

Each R* is —H, —$C_{1-6}$ alkyl, or —$(CH_2CH_2O)_r$H. Even more preferably, each R* is —H or —$C_{1-6}$ alkyl.

q is 0 to 4. Preferably q is 0, 1 or 2. More preferably, q is 0 or 1.

r is 1 to 3. Preferably r is 1 or 2. More preferably, r is 1.

Furthermore, the optional substituent(s) of any group which is indicated as being "optionally substituted" in the present specification may be one or more substituents $R^a$ as defined above, unless other substituents are defined for this group.

Each $R^a$ is preferably selected from —$C_{1-6}$ alkyl, —C(O)—$C_{1-6}$ alkyl, -Hal, —$CF_3$, —CN, —COOR*, —OR*, —$(CH_2)_q NR*R**$, —C(O)—NR*R** and —NR*—C(O)—$C_{1-6}$ alkyl; wherein each R** is —H, or —$C_{1-6}$ alkyl; each R* is —H, —$C_{1-6}$ alkyl, or —$(CH_2CH_2O)_r$H; r is 1 or 2 and q is 0, 1 or 2. More preferably, each $R^a$ is selected from —$C_{1-6}$ alkyl, —C(O)—$C_{1-6}$ alkyl, -Hal, —$CF_3$, —CN, —COOR*, —OR*, —$(CH_2)_q$ NR*R**, —C(O)—NR*R** and —NR*—C(O)—$C_{1-6}$ alkyl; wherein each R** is —H, or —$C_{1-6}$ alkyl; each R* is —H, —$C_{1-6}$ alkyl, or —$(CH_2CH_2O)_r$H; r is 1 and q is 0, 1 or 2. Even more preferably, each $R^a$ is selected from —$C_{1-6}$ alkyl, —C(O)—$C_{1-6}$ alkyl, -Hal, —$CF_3$, —CN, —COOR*, —OR*, —$(CH_2)_q NR*R**$, —C(O)—NR*R** and —NR*—C(O)—$C_{1-6}$ alkyl; wherein each R** is —H, or —$C_{1-6}$ alkyl; each R* is —H or —$C_{1-6}$ alkyl; and q is 0 or 1. Still more preferably, each $R^a$ is selected from —$C_{1-6}$ alkyl, —C(O)—$C_{1-6}$ alkyl, -Hal, —$CF_3$, —CN, —COOR*, —OR*, —$(CH_2)_q NR*R**$, —C(O)—NR*R** and —NR*—C(O)—$C_{1-6}$ alkyl; wherein each R** is —H; each R* is —H or —$C_{1-6}$ alkyl and q is 0 or 1. Still more preferably, each $R^a$ is selected from —$C_{1-6}$ alkyl, —C(O)—$C_{1-6}$ alkyl, -Hal, —$CF_3$, —CN, —OR*. Still more preferably, each $R^a$ is selected from —$C_{1-4}$ alkyl, —C(O)—$C_{1-4}$ alkyl, -Hal, —$CF_3$, —CN, —OR*. Still more preferably, each $R^a$ is selected from —$C_{1-4}$ alkyl, -Hal, —$CF_3$, —CN and —OR*. Still more preferably, each $R^a$ is selected from —$C_{1-4}$ alkyl, -Hal and —$CF_3$.

Preferably, the optional substituent(s) of the optionally substituted cycloalkyl group, optionally substituted heterocycloalkyl group, optionally substituted aryl group, optionally substituted heteroaryl group and/or optionally substituted hydrocarbon group is -halogen (preferably F), —O—$C_{1-4}$ alkyl or —CN. Preferably, the optional substituent of the alkyl group is selected from halogen, —CN, —NR*R* (wherein each R* is chosen independently of each other), —OH and —O—$C_{1-6}$ alkyl. More preferably the substituent of the alkyl group is -halogen, even more preferably F.

In preferred compounds of formula (Ia)

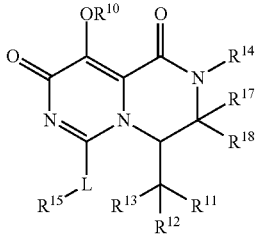

(Ia)

L is selected from $NR^L$, $N(R^L)C(O)$, $N(R^L)SO_2O$, $OC(O)$, $OSO_2$, S, SO and $SO_2$; wherein $R^L$ is —H, -(optionally substituted $C_{1-6}$ alkyl), -(optionally substituted $C_{3-7}$ cycloalkyl) or -(optionally substituted aryl);

$R^{10}$ is —H or a —$C_{1-6}$ alkyl group which may optionally be substituted by one or more halogen atoms;

$R^{11}$ is —H or a —$C_{1-4}$ alkyl group;

$R^{12}$ and $R^{13}$ are each selected from -(optionally substituted aryl or heteroaryl group which contains from 5 to 10 carbon atoms and optionally 1 to 4 heteroatoms selected from O, N and S);

or $R^{12}$ and $R^{13}$ are optionally joined together to form an -(optionally substituted hydrocarbon group which contains from 5 to 20 carbon atoms and optionally 1 to 4 heteroatoms selected from O, N and S and which contains at least one ring);

$R^{14}$ is —H, -(optionally substituted $C_{1-6}$ alkyl), or -(optionally substituted aryl);

$R^{15}$ is selected from —H, -(optionally substituted $C_{1-6}$ alkyl), —$C_{1-4}$ alkyl-(optionally substituted $C_{3-7}$ cycloalkyl) and —$C_{1-4}$ alkyl-(optionally substituted aryl);

$R^{17}$ is selected from —H, -(optionally substituted $C_{1-6}$ alkyl), -(optionally substituted $C_{3-7}$ cycloalkyl) and -(optionally substituted aryl);

$R^{18}$ is selected from —H, -(optionally substituted $C_{1-6}$ alkyl), -(optionally substituted $C_{3-7}$ cycloalkyl) and -(optionally substituted aryl);

each $R^a$ is selected from —$C_{1-6}$ alkyl, —C(O)—$C_{1-6}$ alkyl, -Hal, —$CF_3$, —CN, —COOR*, —OR*, —$(CH_2)_q NR^*R^{**}$, —C(O)—$NR^*R^{**}$ and —NR*—C(O)—$C_{1-6}$ alkyl; wherein each $R^{**}$ is —H, or —$C_{1-6}$ alkyl; each $R^*$ is —H, —$C_{1-6}$ alkyl, or —$(CH_2CH_2O)_rH$; r is 1 and q is 0, 1 or 2.

In more preferred compounds of formula (Ia),
L is selected from $NR^L$, $N(R^L)C(O)$, O, S, SO and $SO_2$; wherein $R^L$ is —H or -(optionally substituted $C_{1-4}$ alkyl);
$R^{10}$ is —H or $C_{1-6}$ alkyl;
$R^{11}$ is —H;
$R^{12}$ and $R^{13}$ are each selected from -(aryl which contains 6 to 10 carbon atoms and is optionally substituted with one or more selected from halogen and $C_{1-4}$alkyl);
or $R^{12}$ and $R^{13}$ are optionally joined together to form an -(optionally substituted hydrocarbon group which contains from 5 to 20 carbon atoms and optionally 1 to 4 heteroatoms selected from O, N and S and which contains at least one ring);
$R^{14}$ is —H, $C_{1-6}$ alkyl which is optionally substituted with one or more halogen, or $C_{6-10}$ aryl which is optionally substituted with one or more halogen;
$R^{15}$ is selected from —H, -(optionally substituted $C_{1-6}$ alkyl) and —$C_{1-4}$ alkyl-($C_{6-10}$ aryl optionally substituted with one or more selected from —O—$C_{1-4}$ alkyl, halogen and —$C_{1-4}$ alkyl);

$R^{17}$ is selected from —H, -(optionally substituted $C_{1-6}$ alkyl), -(optionally substituted $C_{3-7}$ cycloalkyl) and -(optionally substituted phenyl);

$R^{18}$ is selected from —H, -(optionally substituted $C_{1-6}$ alkyl), -(optionally substituted $C_{3-7}$ cycloalkyl) and -(optionally substituted phenyl);

each $R^a$ is selected from —$C_{1-6}$ alkyl, —C(O)—$C_{1-6}$ alkyl, -Hal, —$CF_3$, —CN, —COOR*, —OR*, —$(CH_2)_q NR^*R^{**}$, —C(O)—$NR^*R^{**}$ and —NR*—C(O)—$C_{1-6}$ alkyl; wherein each $R^{**}$ is —H or $C_{1-4}$ alkyl; each $R^*$ is —H or $C_{1-4}$ alkyl; and q is 0 or 1.

In preferred compounds of formula (Ia), L is selected from O, S, SO and $SO_2$ and $R^{15}$ is -(optionally substituted $C_{1-6}$ alkyl). More preferably, L is selected from O, S, SO and $SO_2$ and $R^{15}$ is methyl.

In other preferred compounds of formula (Ia), L is O and $R^{15}$ is -(optionally substituted $C_{1-6}$ alkyl). More preferably, L is O and $R^{15}$ is methyl.

In preferred compounds of formula (Ib)

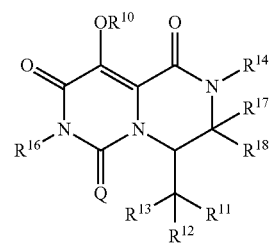

(Ib)

Q is selected from $NR^Q$, O and S; wherein $R^Q$ is —H or -(optionally substituted $C_{1-4}$ alkyl);

$R^{10}$ is —H or a —$C_{1-6}$ alkyl group which may optionally be substituted by one or more halogen atoms;

$R^{11}$ is —H or a —$C_{1-4}$ alkyl group;

$R^{12}$ and $R^{13}$ are each selected from -(optionally substituted aryl or heteroaryl group which contains from 5 to 10 carbon atoms and optionally 1 to 4 heteroatoms selected from O, N and S);

or $R^{12}$ and $R^{13}$ are optionally joined together to form an -(optionally substituted hydrocarbon group which contains from 5 to 20 carbon atoms and optionally 1 to 4 heteroatoms selected from O, N and S and which contains at least one ring);

$R^{14}$ is —H, -(optionally substituted $C_{1-6}$ alkyl), or -(optionally substituted aryl);

$R^{16}$ is selected from —H, -(optionally substituted $C_{1-6}$ alkyl), —$C_{1-4}$ alkyl-(optionally substituted $C_{3-7}$ cycloalkyl) and —$C_{1-4}$ alkyl-(optionally substituted aryl);

$R^{17}$ is selected from —H, -(optionally substituted $C_{1-6}$ alkyl), -(optionally substituted $C_{3-7}$ cycloalkyl) and -(optionally substituted aryl);

$R^{18}$ is selected from —H, -(optionally substituted $C_{1-6}$ alkyl), -(optionally substituted $C_{3-7}$ cycloalkyl) and -(optionally substituted aryl);

each $R^a$ is selected from —$C_{1-6}$ alkyl, —C(O)—$C_{1-6}$ alkyl, -Hal, —$CF_3$, —CN, —COOR*, —OR*, —$(CH_2)_q NR^*R^{**}$, —C(O)—$NR^*R^{**}$ and —NR*—C(O)—$C_{1-6}$ alkyl; wherein each $R^{**}$ is —H, or —$C_{1-6}$ alkyl; each $R^*$ is —H, —$C_{1-6}$ alkyl, or —$(CH_2CH_2O)_rH$; r is 1 and q is 0, 1 or 2.

In more preferred compounds of formula (Ib),
Q is selected from O and S;
$R^{10}$ is —H or $C_{1-4}$ alkyl;
$R^{11}$ is —H;

$R^{12}$ and $R^{13}$ are each selected from -(aryl which contains 6 to 10 carbon atoms and is optionally substituted with one or more selected from halogen and $C_{1-4}$-alkyl);

or $R^{12}$ and $R^{13}$ are optionally joined together to form an -(optionally substituted hydrocarbon group which contains from 5 to 20 carbon atoms and optionally 1 to 4 heteroatoms selected from O, N and S and which contains at least one ring);

$R^{14}$ is —H, $C_{1-6}$ alkyl which is optionally substituted with one or more halogen, or $C_{6-10}$ aryl which is optionally substituted with one or more halogen;

$R^{16}$ is selected from —H, -(optionally substituted $C_{1-6}$ alkyl) and —$C_{1-4}$ alkyl-($C_{6-10}$ aryl optionally substituted with one or more selected from —O—$C_{1-4}$ alkyl, halogen and —$C_{1-4}$ alkyl);

$R^{17}$ is selected from —H, -(optionally substituted $C_{1-6}$ alkyl), -(optionally substituted $C_{3-7}$ cycloalkyl) and -(optionally substituted phenyl);

$R^{18}$ is selected from —H, -(optionally substituted $C_1$-6 alkyl), -(optionally substituted $C_{3-7}$ cycloalkyl) and -(optionally substituted phenyl);

each $R^a$ is selected from —$C_{1-6}$ alkyl, —C(O)—$C_{1-6}$ alkyl, -Hal, —$CF_3$, —CN, —COOR*, —OR*, —$(CH_2)_q NR*R**$, —C(O)—NR*R** and —NR*—C(O)—$C_{1-6}$ alkyl; wherein each R** is —H or $C_{1-4}$ alkyl; each R* is —H or $C_1$-4 alkyl; and q is 0 or 1.

The present inventors have surprisingly found that the compounds according to the present invention which have N, O or S directly attached to the left hand ring have improved pharmacological properties such as improved bioavailability. Without wishing to be bound by theory it is assumed that the presence of the additional nitrogen atom in the left ring leads to improved potency of these compounds. This potency may be even further increased by the selection of $R^{15}$-L.

The compounds of the present invention can be administered to a patient in the form of a pharmaceutical composition which can optionally comprise one or more pharmaceutically acceptable excipient(s) and/or carrier(s).

The compounds of the present invention can be administered by various well known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a spray, a tablet, a capsule, a capslet, lozenge, a liposome, a suppository, a plaster, a band-aid, a retard capsule, a powder, or a slow release formulation. Preferably, the diluent is water, a buffer, a buffered salt solution or a salt solution and the carrier preferably is selected from cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride, may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following non-limiting list:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;

b) lubricants such as magnesium stearate, talc, calcium stearate, zinc stearate, stearic acid, hydrogenated vegetable oil, leucine, glycerides and sodium stearyl fumarates, c) disintegrants such as starches, croscarmellose, sodium methyl cellulose, agar, bentonite, alginic acid, carboxymethyl cellulose, polyvinyl pyrrolidone and the like.

In one embodiment the formulation is for oral administration and the formulation comprises one or more or all of the following ingredients: pregelatinized starch, talc, povidone K 30, croscarmellose sodium, sodium stearyl fumarate, gelatin, titanium dioxide, sorbitol, monosodium citrate, xanthan gum, titanium dioxide, flavoring, sodium benzoate and saccharin sodium.

If a compound of the invention is administered intranasally in a preferred embodiment, it may be administered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoro-alkane such as 1,1,1,2-tetrafluoroethane (HFA 134A™) or 1,1,1,2,3,3,3-heptafluoropropane (HFA 227EA™), carbon dioxide, or another suitable gas. The pressurized container, pump, spray or nebulizer may contain a solution or suspension of the compound of the invention, e.g., using a mixture of ethanol and the propellant as the solvent, which may additionally contain a lubricant, e.g., sorbitan trioleate.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g of the active ingredient (i.e. compound of the invention) per kg body weight. However, in a preferred use of the present invention a compound of the invention is administered to a subject in need thereof in an amount ranging from 1.0 to 500 mg/kg body weight, preferably ranging from 1 to 200 mg/kg body weight. The duration of therapy with a compound of the invention will vary, depending on the severity of the disease being treated and the condition and idiosyncratic response of each individual patient. In one preferred embodiment of a prophylactic or therapeutic use, from 10 mg to 200 mg of the compound are orally administered to an adult per day, depending on the severity of the disease and/or the degree of exposure to disease carriers.

As is known in the art, the pharmaceutically effective amount of a given composition will also depend on the administration route. In general, the required amount will be higher if the administration is through the gastrointestinal tract, e.g., by suppository, rectal, or by an intragastric probe, and lower if the route of administration is parenteral, e.g., intravenous. Typically, a compound of the invention will be administered in ranges of 50 mg to 1 g/kg body weight, preferably 10 mg to 500 mg/kg body weight, if rectal or intragastric administration is used and in ranges of 1 to 100 mg/kg body weight if parenteral administration is used. For intranasal administration, 1 to 100 mg/kg body weight are envisaged.

If a person is known to be at risk of developing a disease treatable with a compound of the invention, prophylactic administration of the biologically active blood serum or the pharmaceutical composition according to the invention may be possible. In these cases the respective compound of the invention is preferably administered in above outlined preferred and particular preferred doses on a daily basis. Preferably, from 0.1 mg to 1 g/kg body weight once a day, preferably 10 to 200 mg/kg body weight. This administration can be continued until the risk of developing the respective viral disorder has lessened. In most instances, however, a compound of the invention will be administered once a disease/disorder has been diagnosed. In these cases it is preferred that a first dose of a compound of the invention is administered one, two, three or four times daily.

The compounds of the present invention are particularly useful for treating, ameliorating, or preventing viral diseases. The type of viral disease is not particularly limited. Examples of possible viral diseases include, but are not limited to, viral diseases which are caused by Poxviridae, Herpesviridae, Adenoviridae, Papillomaviridae, Polyomaviridae, Parvoviridae, Hepadnaviridae, Reoviridae, Filoviridae, Paramyxoviridae, Rhabdoviridae, Orthomyxoviridae, Bunyaviridae, Arenaviridae, Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Filoviridae, Paramyxoviridae, Rhabdoviridae, Orthomyxoviridae, Bunyaviridae, Arenaviridae, Coronaviridae, Picornaviridae, Togaviridae, Flaviviridae, more preferably viral diseases which are caused by orthomyxoviridae.

Examples of the various viruses are given in the following table.

| Family | Virus (preferred examples) |
|---|---|
| Poxviridae | Smallpox virus |
| | Molluscum contagiosum virus |
| Herpesviridae | Herpes simplex virus |
| | Varicella zoster virus |
| | Cytomegalovirus |
| | Epstein Barr virus |
| | Kaposi's sarcoma-associated herpesvirus |
| Adenoviridae | Human adenovirus A-F |
| Papillomaviridae | Papillomavirus |
| Polyomaviridae | BK-virus |
| | JC-Virsu |
| Parvoviridae | B19 virus |
| | Adeno associated virus 2/3/5 |
| Hepadnaviridae | Hepatitis B virus |
| Reoviridae | Reovirus 1/2/3 |
| | Rotavirus A/B/C |
| | Colorado tick fever virus |
| Filoviridae | Ebola virus |
| | Marburg virus |
| Paramyxoviridae | Parainfluenza virus 1-4 |
| | Mumps virus |
| | Measles virus |
| | Respiratory syncytial virus |
| | Hendravirus |
| Rhabdoviridae | Vesicular stomatitis virus |
| | Rabies virus |
| | Mokola virus |
| | European bat virus |
| | Duvenhage virus |
| Orthomyxoviridae | Influenza virus types A-C |
| Bunyaviridae | California encephalitis virus |
| | La Crosse virus |
| | Hantaan virus |
| | Puumala virus |
| | Sin Nombre virus |
| | Seoul virus |
| | Crimean - Congo hemorrhagic fever virus |
| | Sakhalin virus |
| | Rift valley virus |
| | Sandfly fever virus |
| | Uukuniemi virus |
| Arenaviridae | Lassa virus |
| | Lymphocytic choriomeningitis virus |
| | Guanarito virus |
| | Junin virus, |
| | Machupo virus |
| | Sabia virus |
| Coronaviridae | Human coronavirus |
| Picornaviridae | Human enterovirus types A-D (Poliovirus, Echovirus, Coxsackie virus A/B) |
| | Rhinovirus types A/B/C |
| | Hepatitis A virus |
| | Parechovirus |
| | Food and mouth disease virus |
| Hepeviridae | Hepatitis E virus |
| Caliciviridae | Norwalk virus |
| | Sapporo virus |
| Astroviridae | Human astrovirus 1 |
| Togaviridae | Ross River virus |
| | Chikungunya virus |
| | O'nyong-nyong virus |
| | Rubella virus |
| Flaviviridae | Tick-borne encephalitis virus |
| | Dengue virus |
| | Yellow Fever virus |
| | Japanese encephalitis virus |
| | Murray Valley virus |
| | St. Louis encephalitis virus |
| | West Nile virus |
| | Hepatitis C virus |
| | Hepatitis G virus |
| | Hepatitis GB virus |
| Deltavirus | Hepatitis deltavirus |
| Bornaviridae | Bornavirus |
| Prions | |

Preferably, the compounds of the present invention are employed to treat influenza. The present invention covers all virus genera belonging to the family of orthomyxoviridae, specifically influenza virus type A, B, and C, isavirus, and thogotovirus. Within the present invention, the term "influenza" includes influenza caused by any influenza virus such as influenza virus type A, B, and C including their various stains and isolates, and also covers influenza A virus strains commonly referred to as bird flu and swine flu. The subject to be treated is not particularly restricted and can be any vertebrate, such as birds and mammals (including humans).

Without wishing to be bound by theory it is assumed that the compounds of the present invention are capable of inhibiting endonuclease activity, particularly that of influenza virus.

A possible measure of the in vitro endonuclease inhibitory activity of the compounds having the formula (Ia) or (Ib) is the FRET (fluorescence-resonance energy transfer)-based endonuclease activity assay disclosed herein. In this context, the % reduction is the % reduction of the initial reaction velocity (v0) measured as fluorescence increase of a dual-labelled RNA substrate cleaved by the influenza virus endonuclease subunit (PA-Nter) upon compound treatment compared to untreated samples.

The compounds having the general formula (Ia) or (Ib) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza that has been caused by influenza virus infection and conditions associated with this viral infection such as viral pneumonia or secondary bacterial pneumonia and medicaments to treat symptoms such as chills, fever, sore throat, muscle pains, severe headache, coughing, weakness and fatigue. Furthermore, the compounds having the general formula (Ia) or (Ib) can be used in combination with anti-inflammatories.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention which is defined by the appended claims in any way.

EXAMPLES

Biological Assays and Data

Luciferase Reporter Assay (LRA)
Assay Purpose and Principle

This in vitro, cell-based assay, is used to identify small molecule inhibitors of influenza A virus and relies upon a replication competent influenza reporter virus. This virus was generated in a A/WSN background (Szretter K J, Balish A L, Katz J M. Curr Protoc Microbiol. Influenza: propagation, quantification, and storage. 2006 December; Chapter 15:Unit 15G.1. doi: 10.1002/0471729256.mc15g01s3) and contains the extremely bright luciferase variant, NanoLuc (Promega), which has been appended to the C-terminus of the polymerase subunit, PA. The reporter virus replicates with near native properties both in cell culture and in vivo. Thus, NanoLuc luciferase activity can be used as a readout of viral infection.

In order to identify small molecule inhibitors of influenza A virus, A549 (human non-small cell lung cancer) cells are infected with the reporter virus and following infection, the cells are treated with serially diluted compounds. The inhibitory effect of the small molecules tested is a direct measure of viral levels and can be rapidly obtained by measuring a reduction in luciferase activity.

Determination of Viral Replication Inhibition by Luciferase Reporter Assay (LRA)

A549 cells were plated in 384-well plates at a density of 10,000 cells per well in Dulbecco's modified Eagle's medium with Glutamax (DMEM, Invitrogen) supplemented 10% fetal bovine serum (FBS, Invitrogen) and 1× penicillin/streptomycin (Invitrogen), herein referred to as complete DMEM, and incubated at 37° C., 5% $CO_2$ overnight. The following day, cells were washed once with 1×PBS and then infected with virus, MOI 0.1 in 10 µl of infection media for 60 min. 15 µl of complete media and diluted compounds (1% DMSO final) added to the wells, and the plates were incubated for 24 h at 37° C., 5% $CO_2$. 15 µl of Nano-Glo reagent (Promega) was added to each well and luminescence was read using a Paradigm Microplate reader (Molecular Devices). Cell viability was determined similarly, in the absence of virus, by measurement of ATP levels with Cell-Titer-Glo reagent (Promega). $EC_{50}$ and $CC_{50}$ values were calculated by fitting dose-response curves with XLFit 4-parameter model 205 software (IDBS).

Virus and Cell Culture Methods

A/WSN/33 influenza virus containing the NanoLuc reporter construct was obtained from the laboratory of Andrew Mehle (University of Wisconsin). A549 human lung carcinoma cells were purchased (ATCC). All studies were performed with A549 cells cultured in complete DMEM. Influenza virus stocks were propagated in MDBK cells (ATCC) using standard methods (Szretter K J, Balish A L, Katz J M. Curr Protoc Microbiol. Influenza: propagation, quantification, and storage. 2006 December; Chapter 15:Unit 15G.1. doi: 10.1002/0471729256.mc15g01s3), and stocks frozen at −80° C. Viral infections were carried out using DMEM Glutamax supplemented with 0.3% BSA (Sigma), 25 mM Hepes (Sigma), and 1× penicillin/streptomycin (Invitrogen).

| $IC_{50}$ values of viral replication inhibition in a cell-based Luciferase Reporter Assay (LRA) | | |
|---|---|---|
| Example | Structure | $IC_{50}$ [uM] |
| 1a-1 | (chemical structure) | 0.153 |

-continued

IC$_{50}$ values of viral replication inhibition in a cell-based Luciferase Reporter Assay (LRA)

| Example | Structure | IC$_{50}$ [uM] |
|---|---|---|
| 1a-2 | 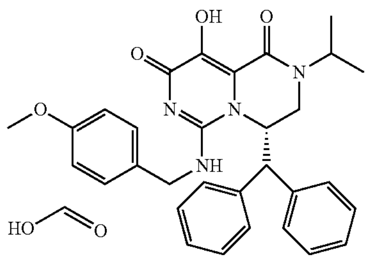 | 2.067 |
| 1a-3 | 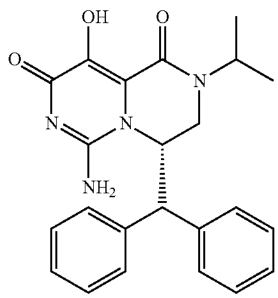 [SMILES: CC(C)N1C[C@H](C(c2ccccc2)c2ccccc2)n2c(N)nc(=O)c(O)c2C1=O] | >50 |
| 1a-4 | 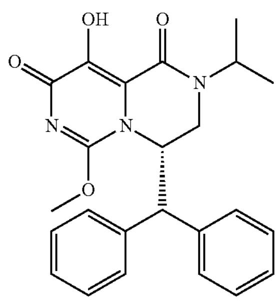 [SMILES: COc1nc(=O)c(O)c2n1[C@@H](C(c1ccccc1)c1ccccc1)CN(C(C)C)C2=O] | 0.014 |
| 1a-5 | 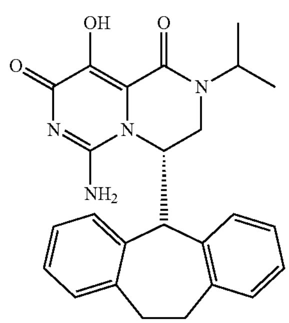 [SMILES: CC(C)N1C[C@H](C2c3ccccc3CCc3ccccc32)n2c(N)nc(=O)c(O)c2C1=O] | >50 |
| 1a-6 | 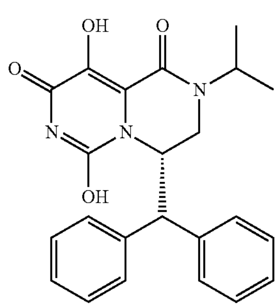 [SMILES: CC(C)N1C[C@H](C(c2ccccc2)c2ccccc2)n2c(O)nc(=O)c(O)c2C1=O] | 0.218 |
| 1a-7 | 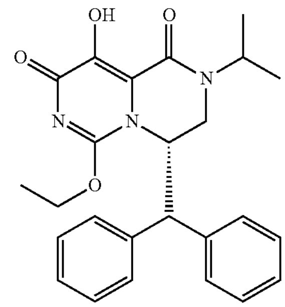 [SMILES: CCOc1nc(=O)c(O)c2n1[C@@H](C(c1ccccc1)c1ccccc1)CN(C(C)C)C2=O] | 0.069 |
| 1a-8 | 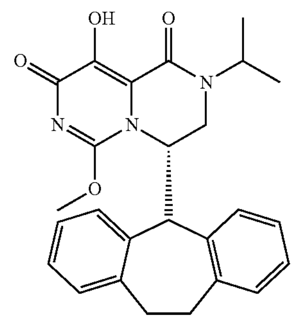 [SMILES: COc1nc(=O)c(O)c2n1[C@@H](C1c3ccccc3CCc3ccccc31)CN(C(C)C)C2=O] | 0.006 |
| 1a-9 | 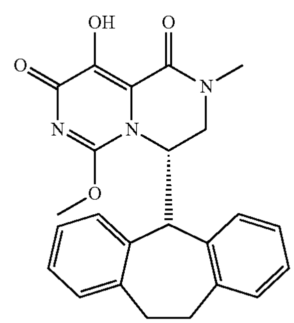 [SMILES: COc1nc(=O)c(O)c2n1[C@@H](C1c3ccccc3CCc3ccccc31)CN(C)C2=O] | 0.006 |
| 1a-10 | 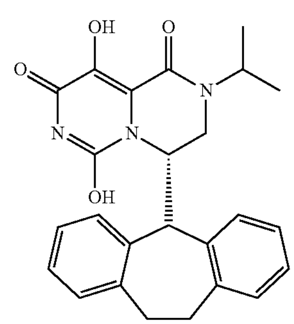 [SMILES: CC(C)N1C[C@H](C2c3ccccc3CCc3ccccc32)n2c(O)nc(=O)c(O)c2C1=O] | 0.098 |

IC$_{50}$ values of viral replication inhibition in a cell-based Luciferase Reporter Assay (LRA)

| Example | Structure | IC$_{50}$ [uM] |
|---|---|---|
| 1a-11 | 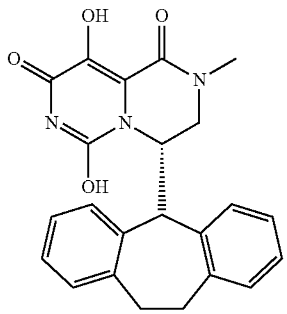 [SMILES: CN1C[C@H](C2c3ccccc3CCc3ccccc32)n2c(O)nc(=O)c(O)c2C1=O] | 0.128 |
| 1a-12 | 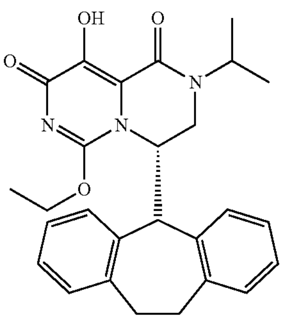 [SMILES: CCOc1nc(=O)c(O)c2n1[C@@H](C1c3ccccc3CCc3ccccc31)CN(C(C)C)C2=O] | 0.024 |
| 1a-13 | 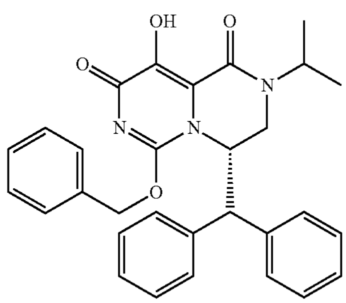 [SMILES: CC(C)N1C[C@H](C(c2ccccc2)c2ccccc2)n2c(OCc3ccccc3)nc(=O)c(O)c2C1=O] | 8.317 |
| 1a-14 | 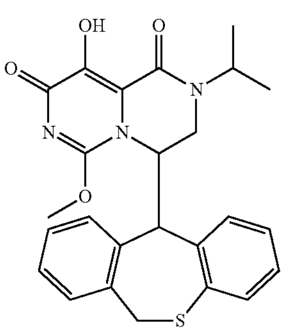 [SMILES: COc1nc(=O)c(O)c2n1C(C1c3ccccc3CSc3ccccc31)CN(C(C)C)C2=O] | separate isomers:<br>0.002<br>0.035<br>0.004<br>0.028 |
| 1a-15 | 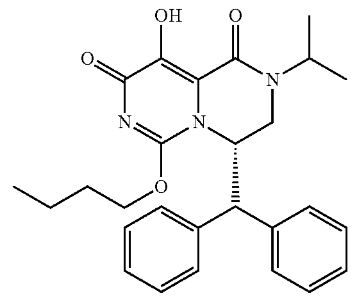 [SMILES: CCCCOc1nc(=O)c(O)c2n1[C@@H](C(c1ccccc1)c1ccccc1)CN(C(C)C)C2=O] | 15.3 |
| 1a-16 | 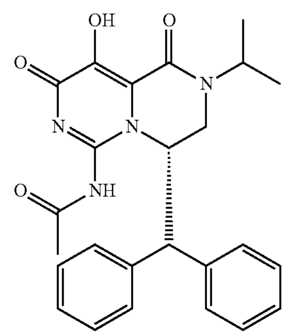 [SMILES: CC(=O)Nc1nc(=O)c(O)c2n1[C@@H](C(c1ccccc1)c1ccccc1)CN(C(C)C)C2=O] | 0.023 |
| 1a-17 | 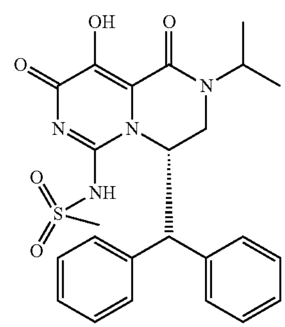 [SMILES: CC(C)N1C[C@H](C(c2ccccc2)c2ccccc2)n2c(NS(C)(=O)=O)nc(=O)c(O)c2C1=O] | 1.67 |
| 1a-18 | 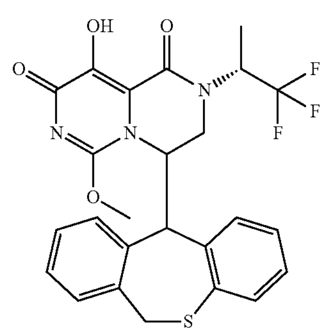 [SMILES: COc1nc(=O)c(O)c2n1C(C1c3ccccc3CSc3ccccc31)CN([C@H](C)C(F)(F)F)C2=O] | separate isomers:<br>0.121<br>0.014<br>0.425<br>0.022 |

27
-continued
IC$_{50}$ values of viral replication inhibition in a cell-based Luciferase Reporter Assay (LRA)
| Example | Structure | IC$_{50}$ [uM] |
|---|---|---|
| 1a-19 | 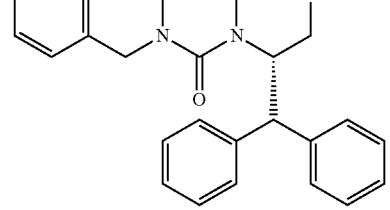 | separate isomers: 0.134 0.002 0.136 0.006 |
| 1a-20 | 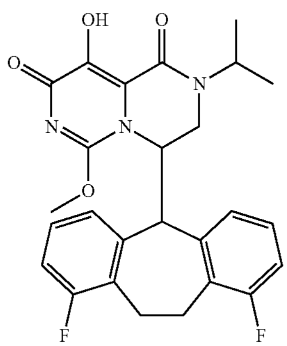 [SMILES: COc1nc(=O)c(O)c2n1C(C1c3cccc(F)c3CCc3c(F)cccc31)CN(C(C)C)C2=O] | 0.016 |
| 1a-21 | 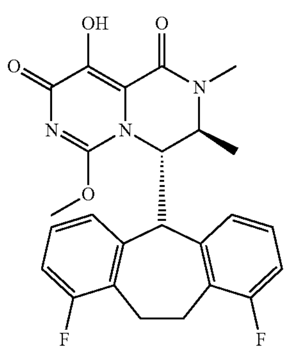 [SMILES: COc1nc(=O)c(O)c2n1[C@@H](C1c3cccc(F)c3CCc3c(F)cccc31)[C@H](C)N(C)C2=O] | 0.015 |
| 1b-1 | 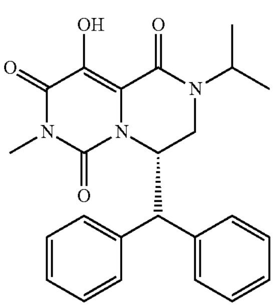 [SMILES: CC(C)N1C[C@H](C(c2ccccc2)c2ccccc2)n2c(c(O)c(=O)n(C)c2=O)C1=O] | 1.658 |
28
-continued
IC$_{50}$ values of viral replication inhibition in a cell-based Luciferase Reporter Assay (LRA)
| Example | Structure | IC$_{50}$ [uM] |
|---|---|---|
| 1b-2 | 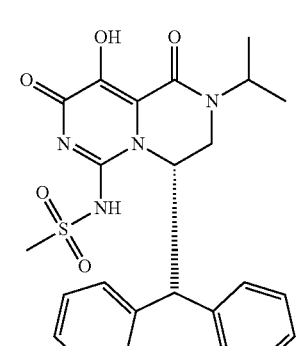 | 4.298 |
| Ia-22 | 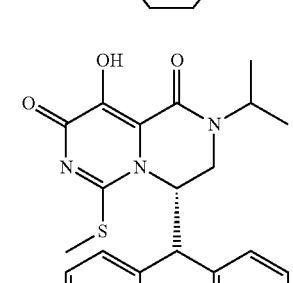 | 0.144 |
| Ia-23 | | 0.036 |
| Ia-24 | 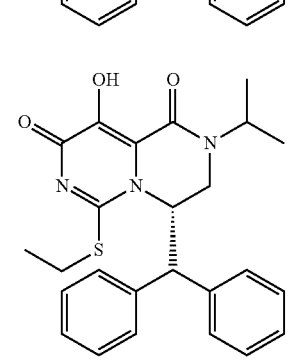 | 11.9 |

-continued

IC$_{50}$ values of viral replication inhibition in a cell-based Luciferase Reporter Assay (LRA)

| Example | Structure | IC$_{50}$ [uM] |
|---|---|---|
| Ia-25 | 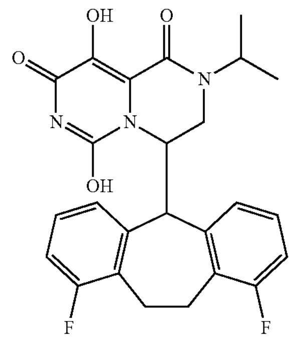 [SMILES: CC(C)N1CC(C2c3cccc(F)c3CCc3c(F)cccc32)n2c(O)nc(=O)c(O)c2C1=O] | 0.086 |
| Ia-26 | 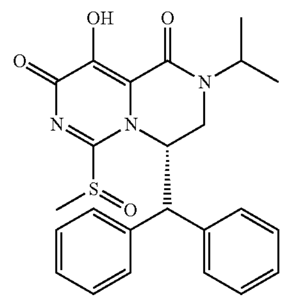 [SMILES: CC(C)N1C[C@H](C(c2ccccc2)c2ccccc2)n2c(S(C)=O)nc(=O)c(O)c2C1=O] | 0.127 |
| Ia-27 | 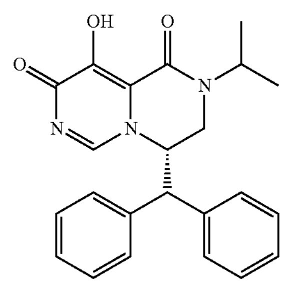 [SMILES: CC(C)N1C[C@H](C(c2ccccc2)c2ccccc2)n2cnc(=O)c(O)c2C1=O] | 0.232 |
| Ia-28 | 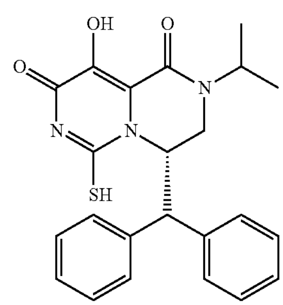 | 0.061 |
| Ia-29 | 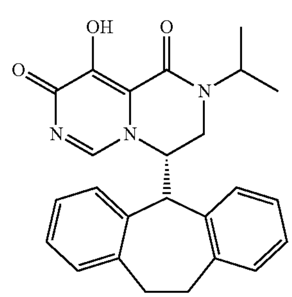 [SMILES: CC(C)N1C[C@H](C2c3ccccc3CCc3ccccc32)n2cnc(=O)c(O)c2C1=O] | 0.022 |
| Ia-30 | | 0.017 |
| Ia-31 | | 0.015 |
| Ia-32 | | 0.117 |
| Ia-33 | | 0.273 |

| Example | Structure | IC$_{50}$ [uM] |
|---|---|---|
| Ia-34 | 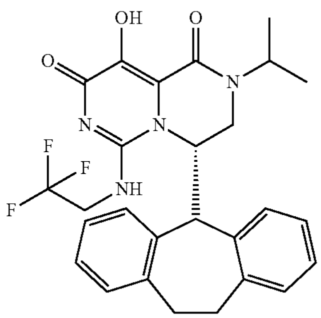 [SMILES: CC(C)N1C[C@H](C2c3ccccc3CCc3ccccc32)n2c(NCC(F)(F)F)nc(=O)c(O)c2C1=O] | 0.05 |
| Ia-35 | 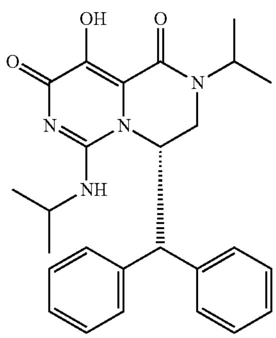 [SMILES: CC(C)Nc1nc(=O)c(O)c2n1[C@@H](C(c1ccccc1)c1ccccc1)CN(C(C)C)C2=O] | 0.324 |
| Ia-36 | 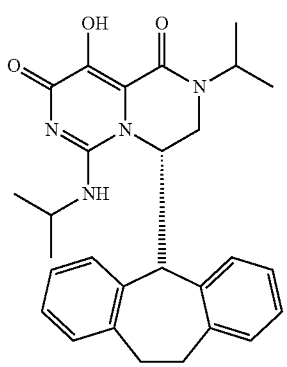 [SMILES: CC(C)Nc1nc(=O)c(O)c2n1[C@@H](C1c3ccccc3CCc3ccccc31)CN(C(C)C)C2=O] | 0.103 |
| Ia-37 | 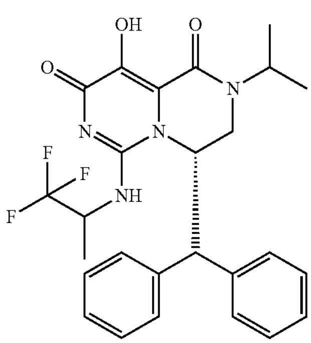 [SMILES: CC(C)N1C[C@H](C(c2ccccc2)c2ccccc2)n2c(NC(C)C(F)(F)F)nc(=O)c(O)c2C1=O] | 0.516 |
| Ia-38 | 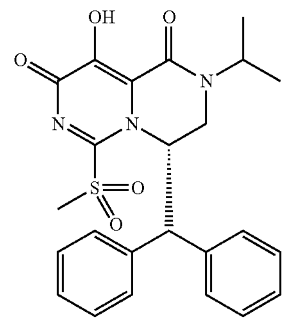 [SMILES: CC(C)N1C[C@H](C(c2ccccc2)c2ccccc2)n2c(S(C)(=O)=O)nc(=O)c(O)c2C1=O] | 0.11 |
| Ia-39 | 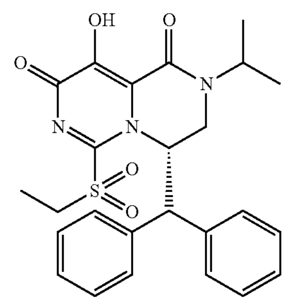 [SMILES: CCS(=O)(=O)c1nc(=O)c(O)c2n1[C@@H](C(c1ccccc1)c1ccccc1)CN(C(C)C)C2=O] | 0.47 |
| Ia-40 | 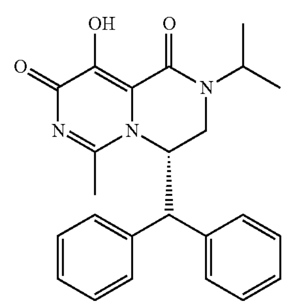 [SMILES: Cc1nc(=O)c(O)c2n1[C@@H](C(c1ccccc1)c1ccccc1)CN(C(C)C)C2=O] | 0.119 |
| Ia-41 | 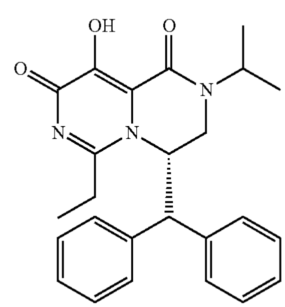 [SMILES: CCc1nc(=O)c(O)c2n1[C@@H](C(c1ccccc1)c1ccccc1)CN(C(C)C)C2=O] | 0.077 |

IC₅₀ values of viral replication inhibition in a cell-based Luciferase Reporter Assay (LRA)

| Example | Structure | IC₅₀ [uM] |
|---|---|---|
| Ia-42 | 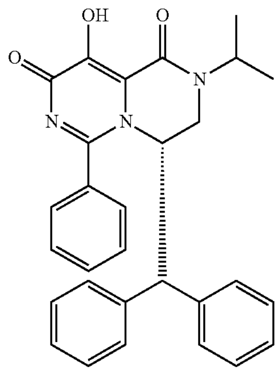 [SMILES: CC(C)N1C[C@H](C(c2ccccc2)c2ccccc2)n2c(-c3ccccc3)nc(=O)c(O)c2C1=O] | 0.126 |
| Ia-43 | 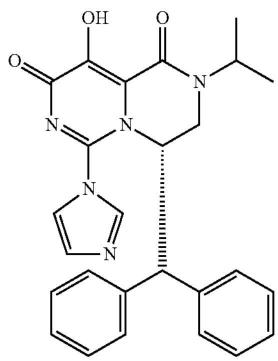 [SMILES: CC(C)N1C[C@H](C(c2ccccc2)c2ccccc2)n2c(-n3ccnc3)nc(=O)c(O)c2C1=O] | 0.495 |
| Ia-44 | 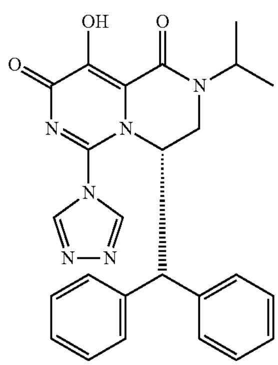 [SMILES: CC(C)N1C[C@H](C(c2ccccc2)c2ccccc2)n2c(-n3cnnc3)nc(=O)c(O)c2C1=O] | 0.13 |
| Ia-45 | 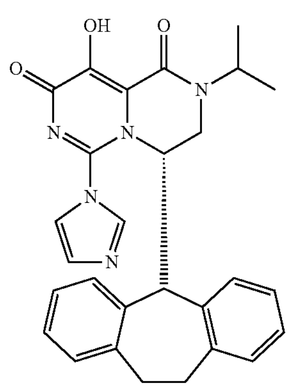 [SMILES: CC(C)N1C[C@H](C2c3ccccc3CCc3ccccc32)n2c(-n3ccnc3)nc(=O)c(O)c2C1=O] | 0.062 |
| Ia-46 | | 0.055 |
| Ia-47 | | 0.04 |
| Ia-48 | | 0.02 |
| Ia-49 | | 0.88 |

IC$_{50}$ values of viral replication inhibition in a cell-based Luciferase Reporter Assay (LRA)

| Example | Structure | IC$_{50}$ [uM] |
|---|---|---|
| Ia-50 | 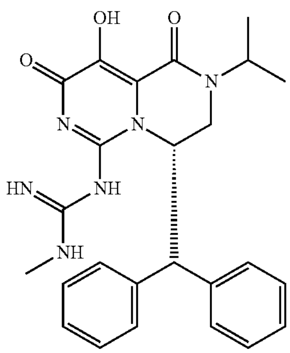 [SMILES: CNC(=N)Nc1nc(=O)c(O)c2n1[C@@H](C(c1ccccc1)c1ccccc1)CN(C(C)C)C2=O] | 1.067 |
| Ia-51 | 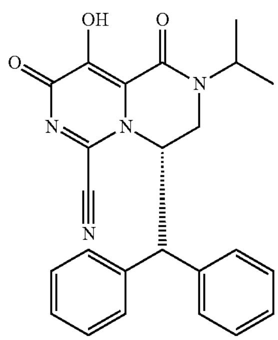 [SMILES: CC(C)N1C[C@H](C(c2ccccc2)c2ccccc2)n2c(C#N)nc(=O)c(O)c2C1=O] | 0.368 |
| Ia-52 | 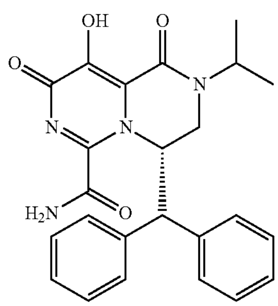 [SMILES: CC(C)N1C[C@H](C(c2ccccc2)c2ccccc2)n2c(C(N)=O)nc(=O)c(O)c2C1=O] | 0.093 |
| Ia-53 | 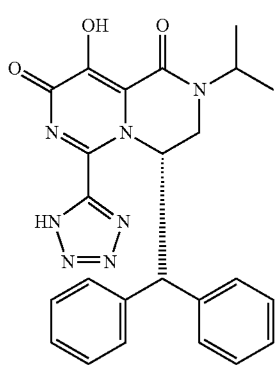 [SMILES: CC(C)N1C[C@H](C(c2ccccc2)c2ccccc2)n2c(-c3nnn[nH]3)nc(=O)c(O)c2C1=O] | 20.2 |
| Ia-54 | 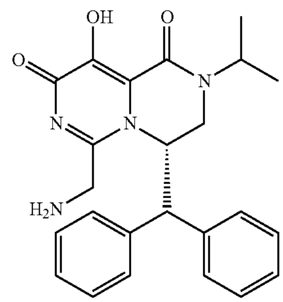 | 0.931 |
| Ia-55 | 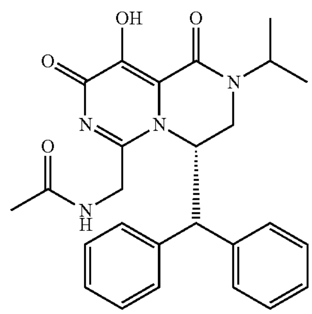 [SMILES: CC(=O)NCc1nc(=O)c(O)c2n1[C@@H](C(c1ccccc1)c1ccccc1)CN(C(C)C)C2=O] | 0.473 |
| Ia-56 | 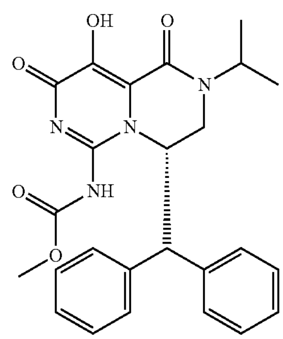 [SMILES: COC(=O)Nc1nc(=O)c(O)c2n1[C@@H](C(c1ccccc1)c1ccccc1)CN(C(C)C)C2=O] | 0.2 |
| Ia-57 | 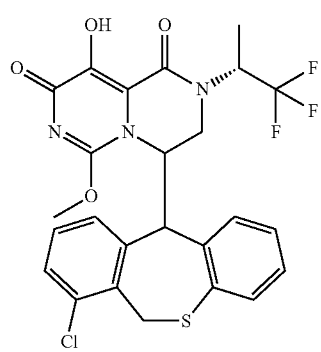 [SMILES: COc1nc(=O)c(O)c2n1C(C1c3ccccc3SCc3c(Cl)cccc31)CN([C@H](C)C(F)(F)F)C2=O] | separate isomers: 0.329 μM, 0.016 μM, 2.730 μM, 0.111 μM |

IC$_{50}$ values of viral replication inhibition in a cell-based Luciferase Reporter Assay (LRA)

| Example | Structure | IC$_{50}$ [uM] |
|---|---|---|
| Ia-58 | | separate isomers: 0.128 0.002 0.018 0.488 |
| Ia-59 | | separate isomers: 0.052 0.0008 0.518 0.014 |
| Ia-60 | | separate isomers: 0.015 0.008 9.300 3.580 |
| Ia-61 | | separate isomers: 0.022 0.025 2.790 not tested |
| Ia-62 | 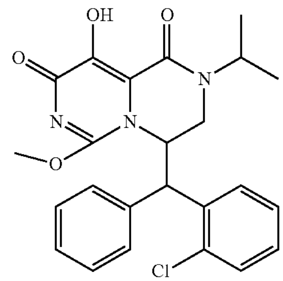 [SMILES: COc1nc(=O)c(O)c2n1C(C(c1ccccc1)c1ccccc1Cl)CN(C(C)C)C2=O] | separate isomers: 0.013 13.08 0.016 |
| Ia-63 | 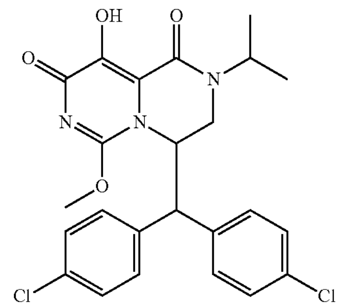 [SMILES: COc1nc(=O)c(O)c2n1C(C(c1ccc(Cl)cc1)c1ccc(Cl)cc1)CN(C(C)C)C2=O] | 0.302 |
| Ia-64 | 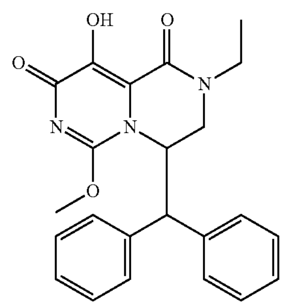 [SMILES: CCN1CC(C(c2ccccc2)c2ccccc2)n2c(OC)nc(=O)c(O)c2C1=O] | 0.05 |
| Ia-65 | 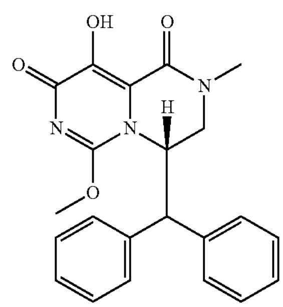 | 0.026 |
| Ia-66 | 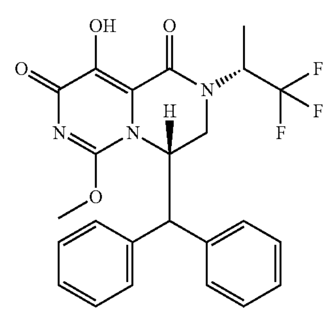 | 0.026 |

TABLE (continued): IC$_{50}$ values of viral replication inhibition in a cell-based Luciferase Reporter Assay (LRA)

| Example | Structure | IC$_{50}$ [uM] |
|---|---|---|
| Ia-67 | (structure) | not tested |
| Ia-68 | (structure) | separate isomers: 2.930, 0.135, 0.020, 0.043 |
| Ia-69 | (structure) | separate isomers: 0.028, 7.140 |
| Ia-70 | (structure) | 0.027 |
| Ia-71 | (structure) | 0.047 |
| Ia-72 | (structure) | 0.04 |
| Ia-73 | (structure) | 0.119 |
| Ia-74 | (structure) | 0.125 |

TABLE -continued

IC$_{50}$ values of viral replication inhibition in a cell-based Luciferase Reporter Assay (LRA)

| Example | Structure | IC$_{50}$ [uM] |
|---|---|---|
| Ia-75 | 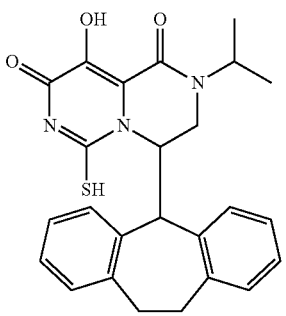 [SMILES: CC(C)N1CC(C2c3ccccc3CCc3ccccc32)n2c(S)nc(=O)c(O)c2C1=O] | 0.045 |
| Ia-76 | 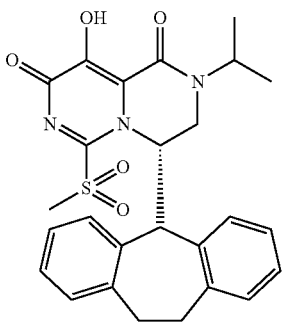 [SMILES: CC(C)N1C[C@H](C2c3ccccc3CCc3ccccc32)n2c(S(C)(=O)=O)nc(=O)c(O)c2C1=O] | 0.013 |
| Ia-77 | 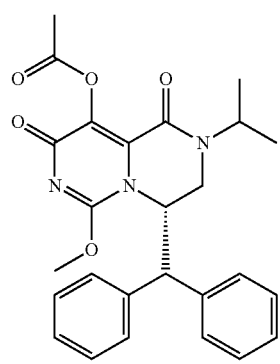 [SMILES: COc1nc(=O)c(OC(C)=O)c2n1[C@@H](C(c1ccccc1)c1ccccc1)CN(C(C)C)C2=O] | prodrug |
| Ia-78 | 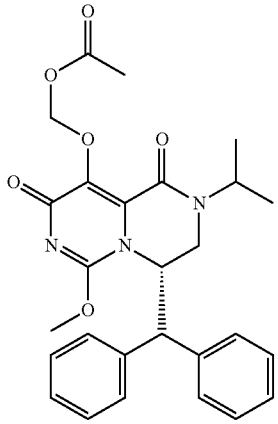 [SMILES: COc1nc(=O)c(OCOC(C)=O)c2n1[C@@H](C(c1ccccc1)c1ccccc1)CN(C(C)C)C2=O] | prodrug |
| Ia-79 | 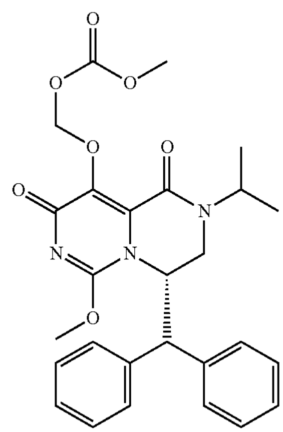 [SMILES: COC(=O)OCOc1c2n(c(OC)nc1=O)[C@@H](C(c1ccccc1)c1ccccc1)CN(C(C)C)C2=O] | prodrug |

Experimental

General: Silica gel chromatography was either performed using cartridges packed with silica gel (ISOLUTE® Columns, TELOS™ Flash Columns) on ISCO Combi Flash Companion or on glass columns on silica gel 60 (32-60 mesh, 60 Å). MS: Mass spectra (MS) were measured with electrospray ionization (ESI) on a Perkin-Elmer SCIEX API 300.

Compounds having the general formula (Ia) or (Ib) may be prepared by any method known in the art. In the following, general methods of their preparation are exemplified which are, however, not limiting on the scope of the present invention.

Scheme 1
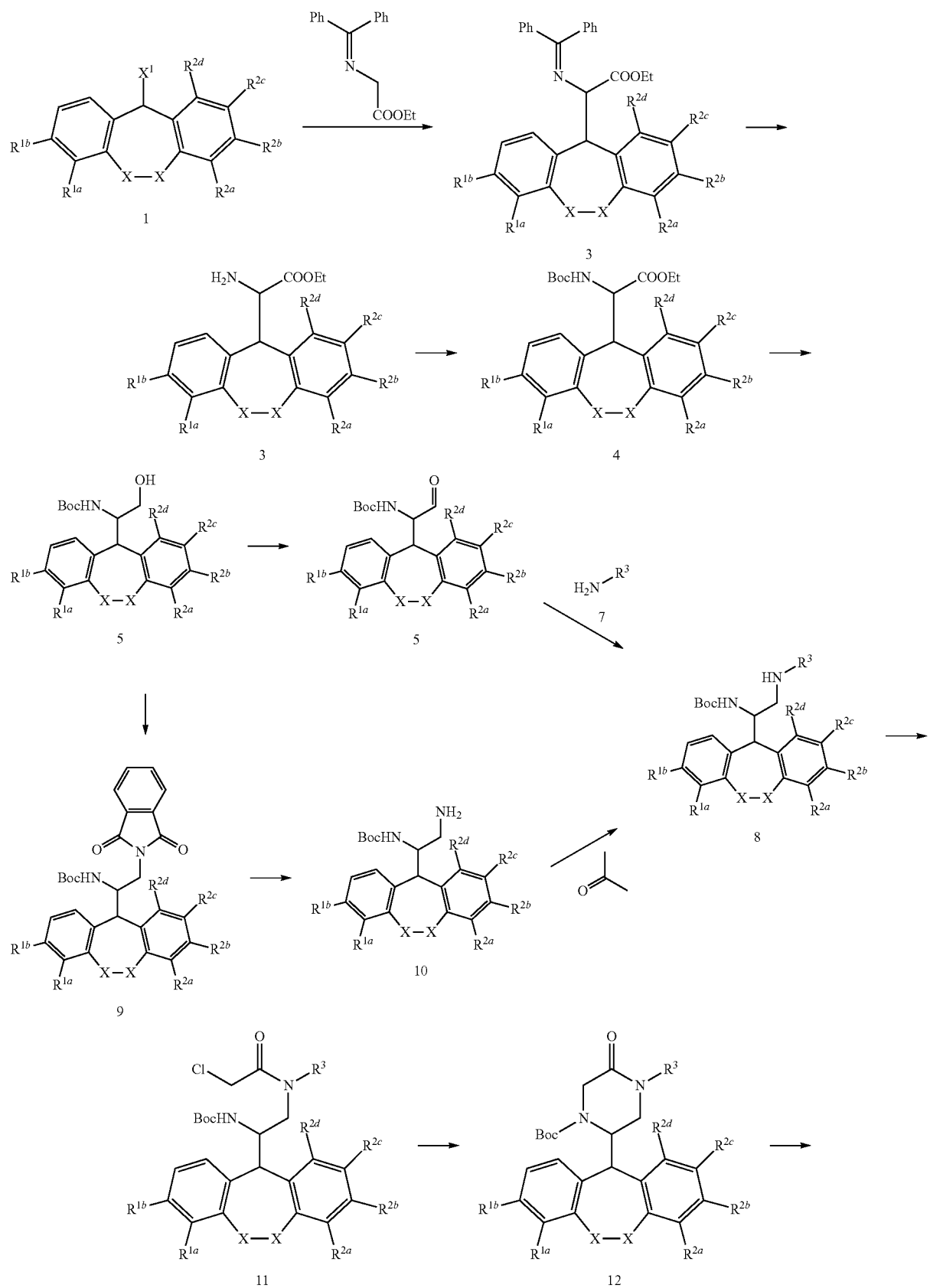

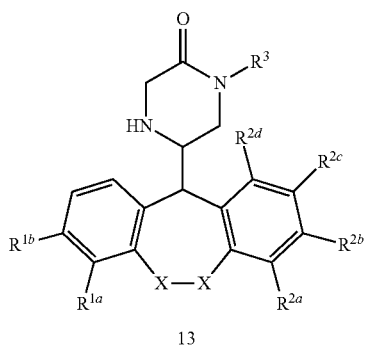
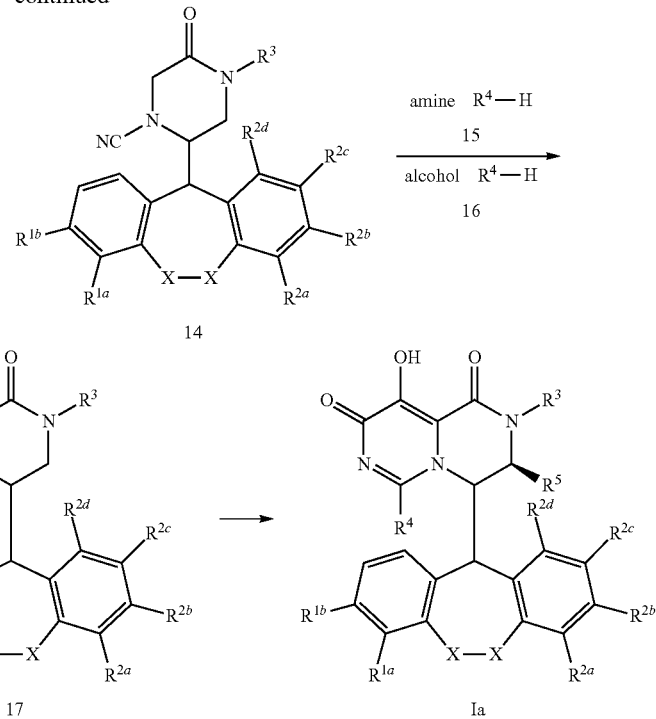

Compounds of Formula (Ia) Having the Following Substitution Patterns were Prepared According to Scheme 1:

| | $R^{1a}$ | $R^{1b}$ | $R^{2a}$ | $R^{2b}$ | $R^{2b}$ | $R^{2d}$ | X-X | $R^3$ | $R^4$ | $R^5$ |
|---|---|---|---|---|---|---|---|---|---|---|
| 1a-1 | H | H | H | H | H | H | — | i-Pr | NHCH$_2$Ph | H |
| 1a-2 | H | H | H | H | H | H | — | i-Pr | NHCH$_2$PhOMe | H |
| 1a-3 | H | H | H | H | H | H | — | i-Pr | NH$_2$ | H |
| 1a-4 | H | H | H | H | H | H | — | i-Pr | OMe | H |
| 1a-5 | H | H | H | H | H | H | CH$_2$CH$_2$ | i-Pr | NH$_2$ | H |
| 1a-6 | H | H | H | H | H | H | — | i-Pr | OH | H |
| 1a-7 | H | H | H | H | H | H | — | i-Pr | OEt | H |
| 1a-8 | H | H | H | H | H | H | CH$_2$CH$_2$ | i-Pr | OMe | H |
| 1a-9 | H | H | H | H | H | H | CH$_2$CH$_2$ | Me | OMe | H |
| 1a-10 | H | H | H | H | H | H | CH$_2$CH$_2$ | i-Pr | OH | H |
| 1a-11 | H | H | H | H | H | H | CH$_2$CH$_2$ | Me | OH | H |
| 1a-12 | H | H | H | H | H | H | CH$_2$CH$_2$ | i-Pr | OEt | H |
| 1a-13 | H | H | H | H | H | H | — | i-Pr | OCH$_2$Ph | H |
| 1a-14 | H | H | H | H | H | H | CH$_2$S | i-Pr | OMe | H |
| 1a-15 | H | H | H | H | H | H | — | i-Pr | O-n-Bu | H |
| 1a-16 | H | H | H | H | H | H | — | i-Pr | NHAc | H |
| 1a-17 | H | H | H | H | H | H | — | i-Pr | NHSO$_2$Me | H |
| 1a-18 | H | H | H | H | H | H | CH$_2$S | CH(Me)CF$_3$ | OMe | H |
| 1a-19 | H | H | H | H | H | H | CH$_2$S | Me | OMe | H |

According to this first pathway, compounds of formula Ia can be prepared by reaction of halogen substituted diphenylmethyl derivatives 1 (X$^1$=Cl, Br, I; X-X=CH$_2$—CH$_2$, CH$_2$—S or H, H; R$^1$ and R$^2$=H or halogen) with ethyl 2-((diphenylmethylene)amino)acetate in the presence of a phase transfer catalyst such as (n-Bu)$_4$NBr and a base such as NaOH or KOH in a solvent mixture of water and an organic solvent, e.g. dichloromethane, to give compounds of general formula 2.

Compounds 2 can be hydrolyzed with a strong acid such as hydrochloric acid in water at elevated temperature, preferably at 100° C., to afford the aminoesters 3.

Protection of the amine group of 3 can be effected with a Z or preferably a Boc group using ZCl or Boc$_2$O and an organic base, preferably triethylamine, in an alcohol as the solvent, preferably methanol, at temperatures between 0 to 60° C., preferably 0° C., thus furnishing the protected aminoesters 4.

Reduction of the protected aminoesters 4 may be performed with a reducing agent such as diisobutylaluminium hydride or preferably LiAlH$_4$ in a solvent such as ethers, preferably tetrahydrofuran, at 0 to 65° C., preferably 0° C., to give the alcohols 5.

Oxidation of the alcohols 5 may be effected by sodium hypochlorite oxidation using 2,2,6,6-tetramethyl-1-piperidinyloxyl radical (TEMPO) in a solvent mixture of water and an organic solvent, preferably dichloromethane with additives such as NaBr and NaHCO$_3$ at 0 to 35° C., preferably 0° C., to give the aldehydes 6. Alternatively, Parikh-Doring conditions such as dimethyl sulfoxide, sulfur trioxide-pyridine complex in the presence of triethylamine as a base or Swern oxidation using oxalyl chloride, dimethyl sulfoxide and an organic base, such as triethylamine, in a solvent such dichloromethane may be used.

In a further variant, the conversion of the protected aminoesters 4 directly to the aldehydes 6 can be accomplished with reduction using diisobutylaluminium hydride.

Reductive amination of the aldehydes 6 with amines $NH_2—R^3$ ($R^3$=alkyl or fluoroalkyl) can be performed with a borohydride derivative, preferably $NaBH(OAc)_3$, and an organic acid, preferably AcOH, in an alcohol as solvent, preferably methanol, at 0 to 65° C., preferably 5° C., to afford the amines 8.

An alternative variant to prepare the amines 8 proceeds via the phthaloyl protected amines 9 by Mitsunobu reaction of the alcohols 5 in the presence of phthalimide, diethyl azodicarboxylate and triphenylphoshine in dichloromethane at 0° C. to give phthaloyl protected amines 9, which can be deprotected with hydrazine in a mixture of solvents such as tetrahydrofuran and methanol at elevated temperature, preferably 70° C., to give the amines 10.

Reductive amination of 10 with acetone ($R^3$=iPr) and $NaBH_3CN$ in an alcohol, preferably methanol, at 0 to 65° C., preferably 5° C., afforded the amines 8.

Chloromethyl amides 11 can be prepared from the amines 8 and 2-chloroacetyl chloride in the presence of an amine, e.g. triethylamine, in a solvent such as dichloromethane at 0 to 35° C., preferably 0 to 5° C.

t-butyloxycarbonyl protected piperazinones of formula 12 may be prepared by cyclization of the chloromethyl amides 11 and a hydride, preferably NaH, in a solvent such as an ether or an amide, preferably dimethylformamide, at 0 to 40° C., preferably 0° C. Racemic compounds of formula 12 may be resolved by supercritical fluid chromatography on a chiral column.

Compounds 12 can be deprotected with a strong acid such as $H_2SO_4$, trifluoroacetic acid or preferably HCl, in an alcohol such as methanol at 0 to 70° C., preferably at 0° C., to give the piperazinones 13.

Introduction of a nitrile group can be effected by the reaction of the piperazinones 13 with cyanogen bromide in the presence of a base, e.g. diisopropylethylamine, in an organic solvent such as dichloromethane at 0 to 25° C., preferably at 22° C., to afford the nitriles 14.

Conversion of the nitriles 14 to substituted amidines 17 ($R^4$=N-benzyl, N-p-methoxybenzyl, $NH_2$) can be achieved by the reaction with an amine $R^4$—H 15 and hexafluoroisopropanol (HFIP) in a microwave oven at elevated temperature between 60 to 120° C. Substituted amidines 17 ($R^4$=OMe, OEt, O-nBu, O-benzyl) can be prepared from nitriles 14 and an alcohol $R^4$—H 16 under basic conditions, e.g. with sodium hydroxide in water, at 60 to 100° C., preferably at 80° C.

Compounds of formula Ia ($R^4$=N-benzyl, N-p-methoxybenzyl, $NH_2$, OMe, OEt, O-nBu, O-benzyl) are prepared by the reaction of substituted amidines 17 ($R^4$=N-benzyl, N-p-methoxybenzyl, $NH_2$, OMe, OEt, O-nBu, O-benzyl) with an alkyl oxalate, preferably diethyl oxalate, and a base, preferably lithium hexamethyldisilazide, in an ether as the solvent, preferably tetrahydrofuran, at −78 to −20° C., preferably at −50 to −20° C. The four isomers of compounds of formula Ia (X-X=$CH_2$—S, R4=OMe) can be separated by achiral HPLC followed by resolution of the two diastereomers using supercritical fluid chromatography on a chiral column.

Compounds of formula Ia wherein $R^4$ is OH can be prepared from compounds of formula Ia wherein $R^4$ is OMe by hydrolysis using a strong acid, such as HCl in an alcohol, preferably methanol, at 0 to 60° C., preferably at 10 to 20° C.

Compounds of formula Ia wherein $R^4$ is NHAc can be prepared from compounds of formula 17 wherein $R^4$—H is $NH_2$ by the reaction with AcCl and a base, e.g. triethylamine, and a solvent such as dichloromethane to afford the intermediates of formula 17 in which $R^4$ is NHAc, These intermediates are then reacted with alkyl oxalate, preferably diethyl oxalate, and a base, preferably lithium hexamethyldisilazide, in an ether as the solvent, preferably tetrahydrofuran, at −78 to −20° C., preferably at −50° C. to give compounds of formula Ia in which $R^4$ is NHAc.

Compounds of formula Ia in which $R^4$ is NHMs (Ms=mesylate) can be prepared from compounds of formula 17 in which $R^4$—H is $NH_2$ by the reaction with methanesulfonyl chloride and a base, e.g. triethylamine, and a solvent, e.g. dichloromethane, to yield intermediates of formula 17 in which $R^4$ is NHMs. These intermediates are then reacted with alkyl oxalate, preferably diethyl oxalate, and a base, preferably lithium hexamethyldisilazide, in an ether as the solvent, preferably tetrahydrofuran, at −50 to 20° C. to give compounds of formula Ia in which $R^4$ is NHMs.

Example 1

Preparation of (1a-1)

(4S)-4-Benzhydryl-6-(benzylamino)-9-hydroxy-2-isopropyl-3,4-dihydropyrazino[1,2-c]pyrimidine-1,8-dione

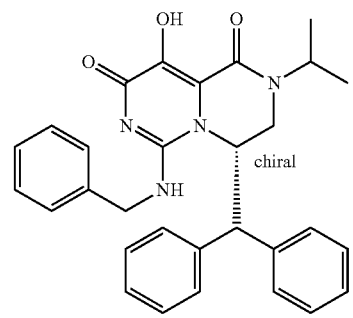

a) tert-Butyl N-[(1S)-1-[(1,3-dioxoisoindolin-2-yl)methyl]-2,2-diphenyl-ethyl]carbamate (9-1)

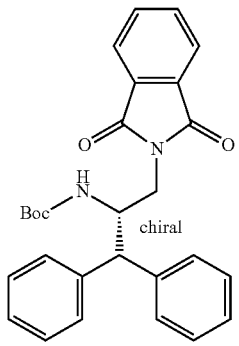 [SMILES: CC(C)(C)OC(=O)N[C@H](CN1C(=O)c2ccccc2C1=O)C(c1ccccc1)c1ccccc1]

To a solution of tert-butyl N-[(1S)-1-(hydroxymethyl)-2,2-diphenyl-ethyl]carbamate (25 g, 76.5 mmol, preparation: Baker, R., Laddhwahetty, T., Seward, E. M., Swain, C. J., WO 93/21181 A1), phthalimide (22.5 g, 153 mmol) and triphenylphoshine (30 g, 114.7 mmol) in dichloromethane (300 ml) was added diethyl azodicarboxylate (20 g, 114.7 mmol) at 0° C. and the mixture was stirred at 5° C. for 16 h. The mixture was evaporated and the residue purified by flash chromatography (silica gel, n-heptane/ethyl acetate, 1:1) to afford the title compound (19.0 g) as a colorless oil.

MS (ESI, m/z): 479.2 [(M+Na)$^+$].

b) tert-Butyl N-[(1S)-1-(aminomethyl)-2,2-diphenyl-ethyl]carbamate (10-1)

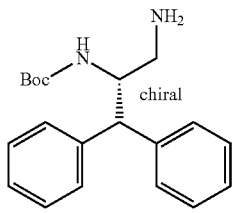 [SMILES: CC(C)(C)OC(=O)N[C@H](CN)C(c1ccccc1)c1ccccc1]

A solution of tert-butyl N-[(1S)-1-[(1,3-dioxoisoindolin-2-yl)methyl]-2,2-diphenyl-ethyl]carbamate (19.0 g, 41.7 mmol) and hydrazine hydrate (41.7 g, 834 mmol) in tetrahydrofuran (150 ml) and methanol (150 ml) was stirred at 70° C. for 2 h. The solution was filtered, the filtrate evaporated and the residue purified by flash chromatography (silica gel, dichloromethane/methanol, 50:1) to give the title compound (12.0 g) as a colorless oil.

MS (ESI, m/z): 327.0 [(M+H)$^+$].

c) tert-Butyl N-[(1S)-1-[(isopropylamino)methyl]-2,2-diphenyl-ethyl]carbamate (8-1)

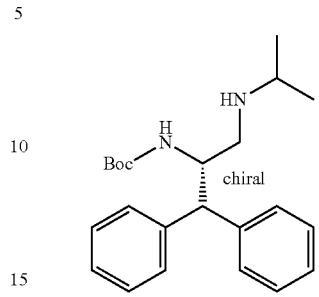

A solution of tert-butyl N-[(1S)-1-(aminomethyl)-2,2-diphenyl-ethyl]carbamate (12.0 g, 37 mmol) and acetone (10.7 g, 185 mmol) in methanol (150 ml) was stirred at 0° C. for 2 h, then NaBH$_3$CN (18.7 g, 296 mmol) was added and stirring was continued at 5° C. for 14 h. The solution was evaporated and the residue partitioned between water (100 ml) and ethyl acetate (2×100 ml), the organic layers were dried, evaporated and the residue (9.0 g recrystallized from methyl-tert-butyl ether (100 ml) to afford the title compound (6.4 g) as a white solid.

MS (ESI, m/z): 369.1[(M+H)$^+$].

d) tert-Butyl N-[(1S)-1-[[(2-chloroacetyl)-isopropylamino]methyl]-2,2-diphenyl-ethyl]carbamate (11-1)

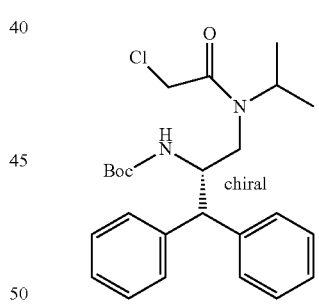

To a stirred mixture of tert-butyl N-[(1S)-1-[(isopropylamino)methyl]-2,2-diphenyl-ethyl]carbamate (33.0 g, 0.089 mol) and NaHCO$_3$ (15.1 g, 0.18 mol) in ethyl acetate (250 ml) and water (250 ml) was added dropwise at 0° C. 2-chloroacetyl chloride (11.3 g, 0.1 mol) and stirring was continued for 10 minutes. The organic layer was concentrated to afford the crude title compound (25.0 g) as a colorless oil.

MS (ESI, m/z): 467.1 [(M+Na)$^+$].

e) tert-Butyl (2S)-2-benzhydryl-4-isopropyl-5-oxo-piperazine-1-carboxylate (12-1)

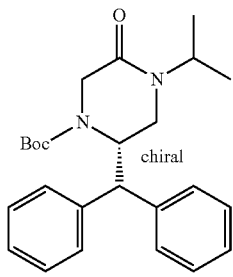 [SMILES: CC(C)N1C[C@H](C(c2ccccc2)c2ccccc2)N(C(=O)OC(C)(C)C)CC1=O]

To a stirred solution of tert-butyl N-[(1S)-1-[[(2-chloroacetyl)-isopropyl-amino]methyl]-2,2-diphenyl-ethyl]carbamate (25.0 g, 0.05 mol) in dimethylformamide (250 ml) was added portion wise at 0° C. NaH (6.0 g, 0.15 mol) and stirring was continued for 1 h. The solution was partitioned between aqueous NH$_4$Cl solution (1.0 L) and ethyl acetate (2×1.0 L), the organic layers were dried over Na$_2$SO$_4$ and evaporated to afford the crude title compound (20.4 g) as a colorless oil.

MS (ESI, m/z): 431.2 [(M+Na)$^+$].

f) (5S)-5-Benzhydryl-1-isopropyl-piperazin-2-one hydrochloride (13-1)

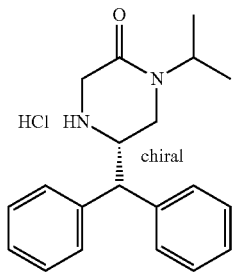 [SMILES: CC(C)N1C[C@H](C(c2ccccc2)c2ccccc2)NCC1=O ; Cl]

To a solution of tert-butyl (2S)-2-benzhydryl-4-isopropyl-5-oxo-piperazine-1-carboxylate (20.4 g, 0.05 mmol) in methanol (200 ml) was added a solution of HCl in methanol (4N, 200 ml) and stirring was continued at 0° C. for 16 h. The solution was evaporated and the residue triturated with methyl-tert-butyl ether (200 ml) to afford the title compound (16.0 g) as a white solid.

MS (ESI, m/z): 309.0 [(M+H)$^+$].

g) (2S)-2-Benzhydryl-4-isopropyl-5-oxo-piperazine-1-carbonitrile (14-1)

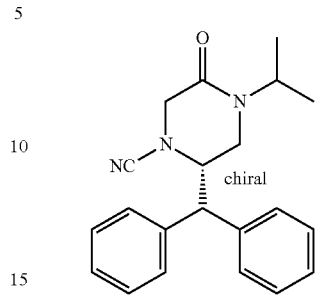

To a stirred solution of (5S)-5-benzhydryl-1-isopropyl-piperazin-2-one-hydrochloride (8.3 g, 0.024 mol) and diisopropylethylamine (10.5 ml, 0.06 mol) in anhydrous dichloromethane (100 ml) was added at 10° C. cyanogen bromide (3.08 g, 0.029 mol) and stirring was continued at 22° C. for 16 h. The solution was washed with aqueous saturated NaHCO$_3$ solution and aqueous HCl (1N), the organic layer was dried, evaporated and the residue purified by flash chromatography (silica gel, n-heptane/ethyl acetate, 1:1) to afford the title compound (7.2 g) as a white solid.

MS (ESI, m/z): 334.1 [(M+H)$^+$].

h) (2S)-2-Benzhydryl-N-benzyl-4-isopropyl-5-oxo-piperazine-1-carboxamidine (17-1)

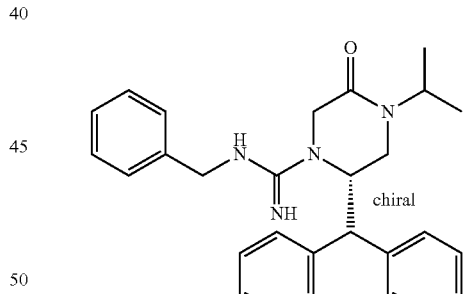

A solution of (2S)-2-benzhydryl-4-isopropyl-5-oxo-piperazine-1-carbonitrile (0.40 g, 1.2 mmol), benzylamine (5 ml) and hexafluoroisopropanol (HFIP) (2 ml) in a sealed vial (12 ml) was heated in microwave on a Biotage Smith Synthesizer at 80° C. for 2 h. The solution was evaporated and the residue purified by preparative HPLC (RP-18, acetonitrile/water containing 0.23% formic acid) to afford the title compound (0.40 g) as a white solid.

MS (ESI, m/z): 441.1 [(M+H)$^+$]

i) (4S)-4-Benzhydryl-6-(benzylamino)-9-hydroxy-2-isopropyl-3,4-dihydropyrazino[1,2-c]-pyrimidine-1,8-dione (1a-1)

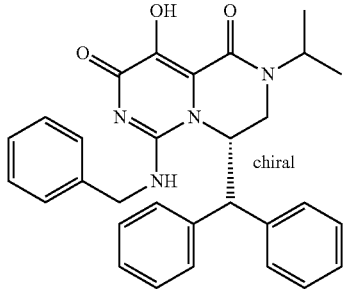 [SMILES: CC(C)N1C[C@H](C(c2ccccc2)c2ccccc2)n2c(NCc3ccccc3)nc(=O)c(O)c2C1=O]

To a stirred solution of (2S)-2-benzhydryl-N-benzyl-4-isopropyl-5-oxo-piperazine-1-carboxamidine (360 mg, 0.9 mmol) in tetrahydrofuran (10 ml) were subsequently added at −20° C. lithium hexamethyldisilazide (1 M, 4.0 ml, 4.0 mmol) and diethyl oxalate (580 mg, 4.0 mmol) and stirring was continued at 0° C. for 1 h. The mixture was partitioned between aqueous HCl (1N, 20 ml) and ethyl acetate (3×20 ml), the organic layers were dried, evaporated and the residue was triturated with methanol (10 ml) to afford the title compound (45 mg) as a white solid.

MS (ESI, m/z): 495.2 [(M+H)$^+$].

Example 2

Preparation of (1a-2)

(4S)-4-Benzhydryl-9-hydroxy-2-isopropyl-6-[(4-methoxyphenyl)methylamino]-3,4-dihydropyrazino[1,2-c]pyrimidine-1,8-dione formate

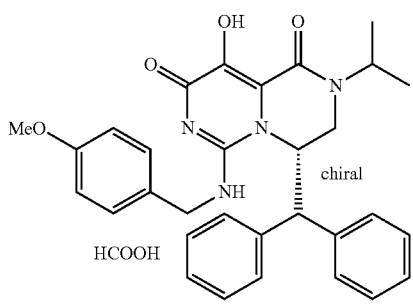 [SMILES: COc1ccc(CNc2nc(=O)c(O)c3n2[C@@H](C(c2ccccc2)c2ccccc2)CN(C(C)C)C3=O)cc1 ; "HCOOH"]

a) (2S)-2-Benzhydryl-4-isopropyl-N-[(4-methoxyphenyl)methyl]-5-oxo-piperazine-1-carboxamidine formiate (17-2)

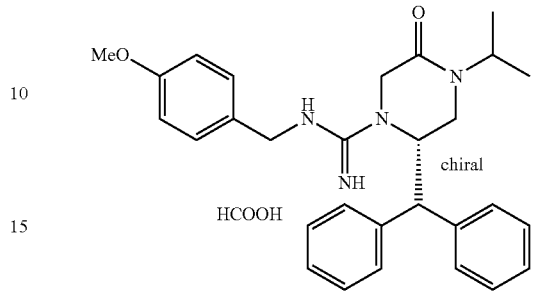

To a solution of (2S)-2-benzhydryl-4-isopropyl-5-oxo-piperazine-1-carbonitrile (from example 1g, 750 mg, 2.3 mmol) in hexafluoroisopropanol (HFIP) (10 ml) was added p-methoxybenzylamine (630 mg, 4.6 mmol) and stirring was continued at 60° C. for 3 d. The solution was evaporated and the residue purified by preparative HPLC (RP-18, acetonitrile/water containing 0.23% formic acid) to afford the title compound (130 mg) as a white solid.

MS (ESI, m/z): 471.1 [(M+H)$^+$].

b) (4S)-4-Benzhydryl-9-hydroxy-2-isopropyl-6-[(4-methoxyphenyl)methylamino]-3,4-dihydropyrazino [1,2-c]pyrimidine-1,8-dione formate (1a-2)

(2S)-2-Benzhydryl-4-isopropyl-N-[(4-methoxyphenyl)methyl]-5-oxo-piperazine-1-carboxamidine formiate was converted according to the procedure described for example 1i to give example 2 as a white solid.

MS (ESI, m/z): 525.2 [(M+H)$^+$].

Example 3

Preparation of (1a-3)

(4S)-6-Amino-4-benzhydryl-9-hydroxy-2-isopropyl-3,4-dihydropyrazino[1,2-c]pyrimidine-1,8-dione

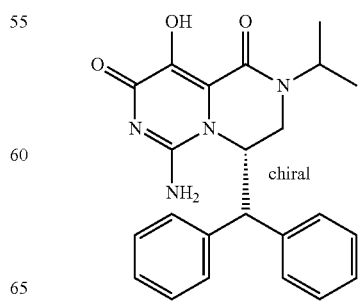

a) (2S)-2-Benzhydryl-4-isopropyl-5-oxo-piperazine-1-carboxamidine (17-3)

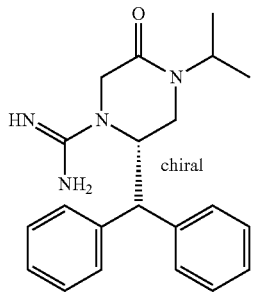 [SMILES: CC(C)N1C[C@H](C(c2ccccc2)c2ccccc2)N(C(=N)N)CC1=O]

A solution of (2S)-2-benzhydryl-4-isopropyl-5-oxo-piperazine-1-carbonitrile (from example 1g, 1.0 g, 3 mmol), ammonia in methanol (7N, 5 ml) and hexafluoroisopropanol (HFIP) (10 ml) was heated in a sealed vial (35 ml) in a microwave (Biotage Smith Synthesizer) at 120° C. for 2 h. The mixture was evaporated and the residue purified by flash chromatography to give the title compound (710 mg) as a white solid.
MS (ESI, m/z): 351.3 [(M+H)$^+$].

b) (4S)-6-Amino-4-benzhydryl-9-hydroxy-2-isopropyl-3,4-dihydropyrazino[1,2-c]pyrimidine-1,8-dione (1a-3)

To a solution of (2S)-2-benzhydryl-4-isopropyl-5-oxo-piperazine-1-carboxamidine (571 mg, 1.9 mmol) in tetrahydrofuran (10 ml) were subsequently added at −50° C. lithium hexamethyldisilazide (5.7 ml, 5.7 mmol) and diethyl oxalate (1.38 g, 9.5 mmol) and stirring was continued at −50° C. for 1 h. The reaction was partitioned between aqueous HCl (0.5 N, 30 ml) and ethyl acetate (2×30 ml), the organic layers were washed with brine (50 ml), dried, evaporated and the residue was purified by preparative HPLC (RP-18, acetonitrile/water containing 0.23% formic acid) to afford example 3 (24 mg) as a white solid.
MS (ESI, m/z): 405.3 [(M+H)$^+$].

Example 4

Preparation of (1a-4)

(4S)-4-Benzhydryl-9-hydroxy-2-isopropyl-6-methoxy-3,4-dihydropyrazino[1,2-c]pyrimidine-1,8-dione

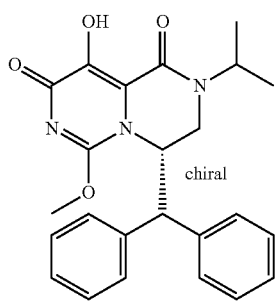 [SMILES: COc1nc(=O)c(O)c2n1[C@@H](C(c1ccccc1)c1ccccc1)CN(C(C)C)C2=O]

a) Methyl (2S)-2-benzhydryl-4-isopropyl-5-oxo-piperazine-1-carboximidate (17-4)

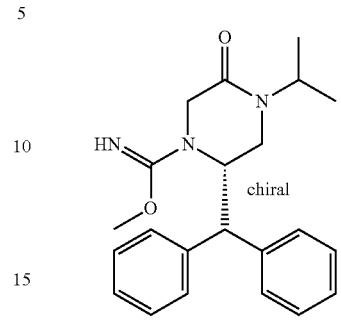

To a solution of (2S)-2-benzhydryl-4-isopropyl-5-oxo-piperazine-1-carbonitrile (from example 1g, 832 mg, 2.5 mmol) in methanol (75 ml) was added a aqueous NaOH solution (20%, 1 ml) and the reaction mixture was stirred at 80° C. for 1 h. The solution was evaporated, the residue partitioned between dichloromethane (50 ml) and water (50 ml), the organic layer was dried and evaporated to give the crude title compound (880 mg) as a white solid.
MS (ESI, m/z): 366.3 [(M+H)$^+$].

b) (4S)-4-Benzhydryl-9-hydroxy-2-isopropyl-6-methoxy-3,4-dihydropyrazino[1,2-c]pyrimidine-1,8-dione (1a-4)

To a stirred solution of methyl (2S)-2-benzhydryl-4-isopropyl-5-oxo-piperazine-1-carboximidate (880 mg, 2.5 mmol) in tetrahydrofuran (20 ml) were subsequently added at −50° C. lithium hexamethyldisilazide (1 M, 12.5 ml, 12.5 mmol) and diethyl oxalate (1.8 g, 12.5 mmol) and stirring was continued at −50° C. for 1 h. The mixture was partitioned between aqueous HCl (1N, 50 ml) and ethyl acetate (3×50 ml), the organic layers were dried, evaporated and the residue was re-crystallized from methyl-tert-butyl ether (20 ml) to give example 4 (500 mg) as a white solid.
MS (ESI, m/z): 420.2 [(M+H)$^+$].

Example 5

Preparation of (1a-5)

(4S)-6-Amino-4-(10,11-dihydro-5H-dibenzo[a,d][7]annulen-5-yl)-9-hydroxy-2-(propan-2-yl)-3,4-dihydro-2H-pyrazino[1,2-c]pyrimidine-1,8-dione

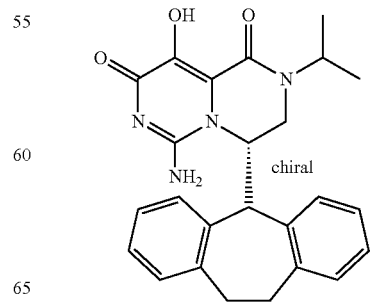

a) Ethyl (10,11-dihydro-5H-dibenzo[a,d][7]annulen-5-yl)[(diphenylmethylidene)amino]acetate (2-5)

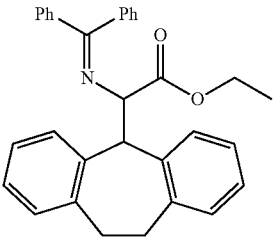 [SMILES: CCOC(=O)C(N=C(c1ccccc1)c1ccccc1)C1c2ccccc2CCc2ccccc21]

To a stirred solution of 10,11-dihydro-5H-dibenzo[a,d]cyclohepten-5-chloride (25.0 g, 110 mmol, preparation: Ilies, M. et al., Bioorganic & Medicinal Chemistry (2003), 11(10), 2227), ethyl 2-((diphenylmethylene)amino)acetate (26.7 g, 100 mmol) and (n-Bu)$_4$NBr (42.5 g, 132 mmol) in dichloromethane (500 ml) was added an aqueous NaOH solution (50%, 100 ml) and stirring was continued 0° C. for 4 h. The mixture was partitioned between water (500 ml) and dichloromethane (2×500 ml), the organic phase was separated and evaporated. The residue was partitioned between methyl-tert-butyl ether (500 ml) and water (500 ml) and the organic layers were dried and evaporated to give the crude title compound (50.0 g) as a colorless oil, which was directly used in the next step.

MS (ESI, m/z): 460.1 (M+H)$^+$.

b) Ethyl amino(10,11-dihydro-5H-dibenzo[a,d][7]annulen-5-yl)acetate-hydrogen chloride (3-5)

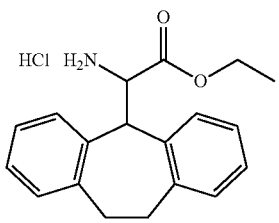 [SMILES: CCOC(=O)C(N)C1c2ccccc2CCc2ccccc21 ; Cl]

A solution of ethyl (10,11-dihydro-5H-dibenzo[a,d][7]annulen-5-yl)[(diphenylmethylidene)-amino]acetate (50.0 g, crude) in aqueous HCl (6N, 500 ml) was stirred at 100° C. for 2 h. The suspension was filtered and the residue washed with ethyl acetate (200 ml) to afford the crude title compound (19.0 g) as a white solid.

MS (ESI, m/z): 296.1 [(M+H)$^+$].

c) Ethyl [(tert-butoxycarbonyl)amino](10,11-dihydro-5H-dibenzo[a,d][7]annulen-5-yl)acetate (4-5)

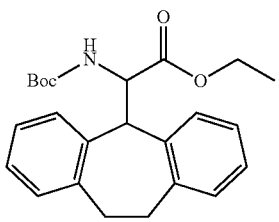 [SMILES: CCOC(=O)C(NC(=O)OC(C)(C)C)C1c2ccccc2CCc2ccccc21]

To a solution of ethyl amino(10,11-dihydro-5H-dibenzo[a,d][7]annulen-5-yl)acetate hydrogen chloride (19.0 g, 58 mmol) in methanol (250 ml) were subsequently added at 5° C. triethylamine (20.0 ml, 145 mmol) and Boc$_2$O (15.0 g, 69 mmol) and stirring was continued at 5° C. for 16 h. The suspension was filtered and the residue washed with methanol (20 ml) to afford the title compound (19.8 g) as a white solid.

MS (ESI, m/z): 418.2 [(M+Na)$^+$].

d) tert-Butyl [1-(10,11-dihydro-5H-dibenzo[a,d][7]annulen-5-yl)-2-hydroxyethyl]carbamate (5-5)

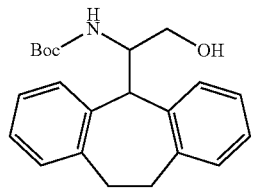 [SMILES: CC(C)(C)OC(=O)NC(CO)C1c2ccccc2CCc2ccccc21]

To a stirred solution of LiAlH$_4$ (1.8 g, 48 mmol) in tetrahydrofuran (200 ml) was added at 0° C. a solution of ethyl [(tert-butoxycarbonyl)amino](10,11-dihydro-5H-dibenzo[a,d][7]annulen-5-yl)acetate (19.0 g, 48 mmol) in tetrahydrofuran (300 ml) and stirring was continued at 0° C. for 1 h. To the mixture were added water (2 ml), aqueous NaOH (15%, 2 ml) and water (6 ml) and thereafter Na$_2$SO$_4$ (40 g) and stirring was continued for 0.5 h. The suspension was filtered and the filtrate was evaporated to give the crude title compound (19.0 g) as a colorless oil.

MS (ESI, m/z): 354.1 [(M+H)$^+$].

e) tert-Butyl [1-(10,11-dihydro-5H-dibenzo[a,d][7]annulen-5-yl)-2-oxoethyl]carbamate (6-5)

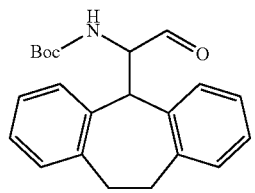 [SMILES: CC(C)(C)OC(=O)NC(C=O)C1c2ccccc2CCc2ccccc21]

To a stirred mixture of tert-butyl [1-(10,11-dihydro-5H-dibenzo[a,d][7]annulen-5-yl)-2-hydroxyethyl]carbamate (19.0 g, 54 mmol), NaBr (540 mg, 5.4 mmol), NaHCO$_3$ (453 mg, 5.4 mmol) and 2,2,6,6-tetramethyl-1-piperidinyloxyl radical (156 mg, 1.0 mmol) in dichloromethane (250 ml) and water (250 ml) was added NaClO (60.0 g, 81 mmol) at 0° C. and stirring was continued at 0° C. for 15 min. The mixture was partitioned between water (500 ml) and dichloromethane (2×500 ml), the organic layers were dried and evaporated to give the crude title compound (20.0 g) as a colorless oil.

MS (ESI, m/z): 374.1 [(M+Na)$^+$].

f) tert-Butyl {1-(10,11-dihydro-5H-dibenzo[a,d][7]annulen-5-yl)-2-[(propan-2-yl)amino]ethyl}-carbamate (8-5)

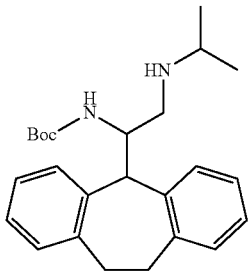 [SMILES: CC(C)NCC(NC(=O)OC(C)(C)C)C1c2ccccc2CCc2ccccc21]

To a stirred solution of tert-butyl [1-(10,11-dihydro-5H-dibenzo[a,d][7]annulen-5-yl)-2-oxoethyl]carbamate (10.0 g, 28.5 mmol) and i-PrNH$_2$ (3.36 g, 57 mmol) in methanol (150 ml) was added at 0° C. AcOH (1.7 g, 28.5 mmol) and stirring was continued at 0° C. for 2 h. NaBH(OAc)$_3$ (12.4 g, 57 mmol) was added and stirring was continued at 5° C. for 14 h. The mixture was evaporated and the residue partitioned between water (200 ml) and dichloromethane (2×300), the organic layers were dried, evaporated and the residue was triturated with ethyl acetate (30 ml) to give the crude title compound (5.16 g) as a white solid.

MS (ESI, m/z): 395.3 [(M+H)$^+$].

g) tert-Butyl {2-[(chloroacetyl)(propan-2-yl)amino]-1-(10,11-dihydro-5H-dibenzo[a,d][7]annulen-5-yl)ethyl}carbamate (11-5)

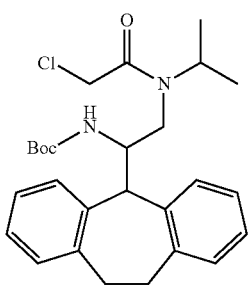 [SMILES: CC(C)N(CC(NC(=O)OC(C)(C)C)C1c2ccccc2CCc2ccccc21)C(=O)CCl]

To a solution of tert-butyl {1-(10,11-dihydro-5H-dibenzo[a,d][7]annulen-5-yl)-2-[(propan-2-yl)amino]ethyl}carbamate (5.16 g, 13 mmol) and triethylamine (2.8 g, 26 mmol) in dichloromethane (50 ml) was added at 5° C. 2-chloroacetyl chloride (1.78 g, 15.6 mmol) and stirring was continued at 5° C. for 16 h. The mixture was partitioned between aqueous HCl (1N, 300 ml) and the organic layer was washed with brine (200 ml). After drying the organic layer and evaporating the solvents, the crude title compound (5.0 g) was obtained as a white solid.

MS (ESI, m/z): 493.3 [(M+Na)$^+$].

h) tert-Butyl (2S)-2-(10,11-dihydro-5H-dibenzo[a,d][7]annulen-5-yl)-5-oxo-4-(propan-2-yl)-piperazine-1-carboxylate (12-5)

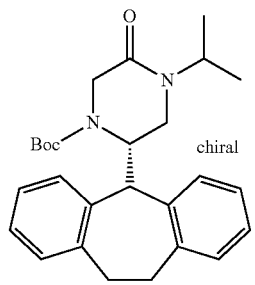 [SMILES: CC(C)N1C[C@H](C2c3ccccc3CCc3ccccc32)N(C(=O)OC(C)(C)C)CC1=O]

tert-Butyl {2-[(chloroacetyl)(propan-2-yl)amino]-1-(10,11-dihydro-5H-dibenzo[a,d][7]annulen-5-yl)ethyl}carbamate (5.0 g, 10.7 mmol) was converted according to the procedure described for example 1e to give the crude product, which was purified by flash chromatography (silica gel, n-heptane/ethyl acetate, 3:1) to give the pure racemic title compound (4.5 g) as a colorless oil. The racemic material was resolved by supercritical fluid chromatography (AS, 250×30 mm, 10 μM particle size, EtOH 20%, 0.1% NH$_3$ in water, 100 bar 80% CO$_2$, 35° C.) to give the (2S)-enantiomer (2.07 g) as the slower eluting enantiomer.

MS (ESI, m/z): 457.2 [(M+Na)$^+$].

i) (5S)-5-(10,11-Dihydro-5H-dibenzo[a,d][7]annulen-5-yl)-1-(propan-2-yl)piperazin-2-one-hydrogen chloride (13-5)

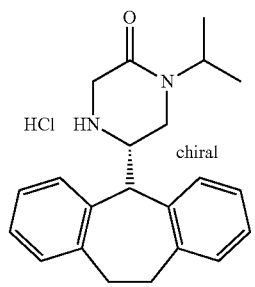 [SMILES: CC(C)N1C[C@H](C2c3ccccc3CCc3ccccc32)NCC1=O ; Cl]

tert-Butyl (2S)-2-(10,11-dihydro-5H-dibenzo[a,d][7]annulen-5-yl)-5-oxo-4-(propan-2-yl)piperazine-1-carboxylate (2.07 g, 4.7 mmol) was converted according to the procedure described for example 1f to give the title compound (1.41 g) as a white solid.

MS (ESI, m/z): 335.2 [(M+H)$^+$].

k) (2S)-2-(10,11-Dihydro-5H-dibenzo[a,d][7]annulen-5-yl)-5-oxo-4-(propan-2-yl)piperazine-1-carbonitrile (14-5)

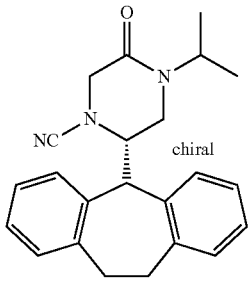 [SMILES: CC(C)N1C[C@H](C2c3ccccc3CCc3ccccc32)N(C#N)CC1=O]

(5S)-5-(10,11-Dihydro-5H-dibenzo[a,d][7]annulen-5-yl)-1-(propan-2-yl)piperazin-2-one-hydrochloride (1.4 g, 3.7 mmol) was converted according to the procedure described for example 1g to give the title compound (1.2 g) as a white solid.

MS (ESI, m/z): 360.2 [(M+H)$^+$].

l) (2S)-2-(10,11-Dihydro-5H-dibenzo[a,d][7]annulen-5-yl)-5-oxo-4-(propan-2-yl)piperazine-1-carboximidamide (17-5)

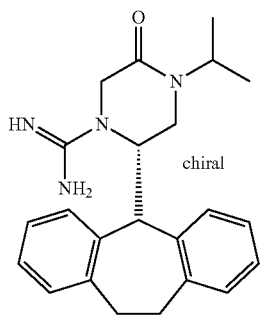 [SMILES: CC(C)N1C[C@H](C2c3ccccc3CCc3ccccc32)N(C(=N)N)CC1=O]

(2S)-2-(10,11-Dihydro-5H-dibenzo[a,d][7]annulen-5-yl)-5-oxo-4-(propan-2-yl)piperazine-1-carbonitrile (360 mg, 1.0 mmol) was converted according to the procedure described for example 3a to give the title compound (130 mg) as a white solid.

MS (ESI, m/z): 377.3 [(M+H)$^+$].

m) (4S)-6-Amino-4-(10,11-dihydro-5H-dibenzo[a,d][7]annulen-5-yl)-9-hydroxy-2-(propan-2-yl)-3,4-dihydro-2H-pyrazino[1,2-c]pyrimidine-1,8-dione (1a-5)

(2S)-2-(10,11-Dihydro-5H-dibenzo[a,d][7]annulen-5-yl)-5-oxo-4-(propan-2-yl)piperazine-1-carboximidamide (130 mg, 0.36 mmol) was converted according to the procedure described for example 3b to give crude example 5. After HPLC purification, the compound was further purified by preparative tin layer chromatography (dichloromethane/methanol, 10:1) to give the pure example 5 (13 mg) as a white solid.

MS (ESI, m/z):431.1 [(M+H)$^+$].

Example 6

Preparation of (1a-6)

(4S)-4-Benzhydryl-6,9-dihydroxy-2-isopropyl-3,4-dihydropyrazino[1,2-c]pyrimidine-1,8-dione

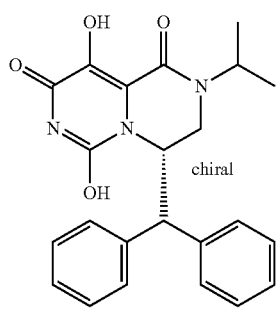 [SMILES: CC(C)N1C[C@H](C(c2ccccc2)c2ccccc2)n2c(O)nc(=O)c(O)c2C1=O]

To a solution of (4S)-4-benzhydryl-9-hydroxy-2-isopropyl-6-methoxy-3,4-dihydropyrazino[1,2-c]pyrimidine-1,8-dione (from example 4, 418 mg, 1.1 mmol) in HCl in methanol (4N, 30 ml) was added water (10 ml) and stirring was continued at 15° C. for 16 h. The mixture was evaporated and the residue triturated with methyl-tert-butyl ether (10 ml) to give the title compound (229 mg) as a white solid.

MS (ESI, m/z): 406.2 [(M+H)$^+$].

Example 7

Preparation of (1a-7)

(4S)-4-Benzhydryl-6-ethoxy-9-hydroxy-2-isopropyl-3,4-dihydropyrazino[1,2-c]-pyrimidine-1,8-dione

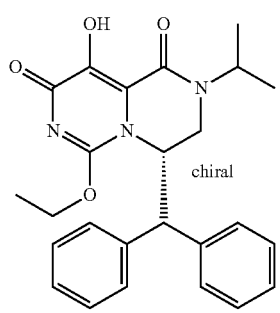 [SMILES: CCOc1nc(=O)c(O)c2n1[C@@H](C(c1ccccc1)c1ccccc1)CN(C(C)C)C2=O]

a) Ethyl (2S)-2-benzhydryl-4-isopropyl-5-oxo-piperazine-1-carboximidate (17-7)

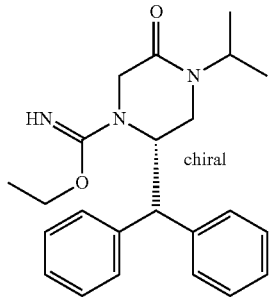 [SMILES: CCOC(=N)N1CC(=O)N(C(C)C)C[C@@H]1C(c1ccccc1)c1ccccc1]

To a solution of (2S)-2-benzhydryl-4-isopropyl-5-oxo-piperazine-1-carbonitrile (from example 1g, 500 mg, 1.5 mmol) in ethanol (10 ml) was added aqueous NaOH solution (20%, 0.6 ml) and the reaction mixture was stirred at 10° C. for 1 h. The solution was evaporated and the residue partitioned between dichloromethane (50 ml) and water (50 ml). The organic layer was dried and evaporated to give the crude title compound (550 mg) as a colorless oil.

MS (ESI, m/z): 380.2 [(M+H)$^+$].

b) (4S)-4-Benzhydryl-6-ethoxy-9-hydroxy-2-isopropyl-3,4-dihydropyrazino[1,2-c]-pyrimidine-1,8-dione (1a-7)

Ethyl (2S)-2-benzhydryl-4-isopropyl-5-oxo-piperazine-1-carboximidate (550 mg, 1.5 mmol) was converted according to the procedure described for example 4b to give crude example 7, which was purified by preparative HPLC (RP-18, acetonitrile/water containing 0.23% formic acid) to afford pure example 7 (32 mg) as a white solid.

MS (ESI, m/z): 434.3 [(M+H)$^+$].

Example 8

Preparation of (1a-8)

(4S)-4-(10,11-Dihydro-5H-dibenzo[a,d][7]annulen-5-yl)-9-hydroxy-6-methoxy-2-(propan-2-yl)-3,4-dihydro-2H-pyrazino[1,2-c]pyrimidine-1,8-dione

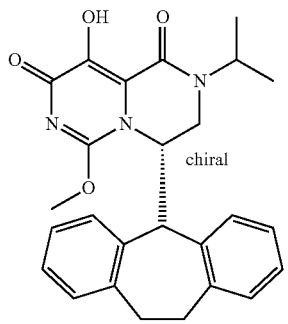 [SMILES: COc1nc(=O)c(O)c2n1[C@@H](C1c3ccccc3CCc3ccccc31)CN(C(C)C)C2=O]

a) Methyl (2S)-2-(10,11-dihydro-5H-dibenzo[a,d][7]annulen-5-yl)-5-oxo-4-(propan-2-yl)piperazine-1-carboximidate (17-8)

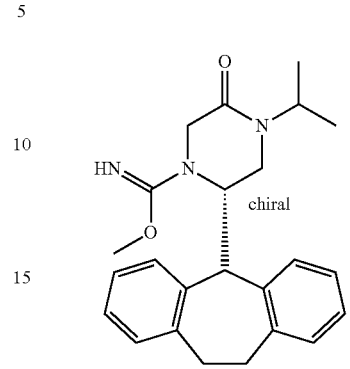

(2S)-2-(10,11-Dihydro-5H-dibenzo[a,d][7]annulen-5-yl)-5-oxo-4-(propan-2-yl)piperazine-1-carbonitrile from example 5k was converted according to the procedure described for example 4a to give the crude title compound.

MS (ESI, m/z): 392.1 [(M+H)$^+$].

b) (4S)-4-(10,11-Dihydro-5H-dibenzo[a,d][7]annulen-5-yl)-9-hydroxy-6-methoxy-2-(propan-2-yl)-3,4-dihydro-2H-pyrazino[1,2-c]pyrimidine-1,8-dione (1a-8)

Methyl (2S)-2-(10,11-dihydro-5H-dibenzo[a,d][7]annulen-5-yl)-5-oxo-4-(propan-2-yl)piperazine-1-carboximidate was converted according to the procedure described for example 4b to give crude example 8, which was purified by preparative HPLC (RP-18, acetonitrile/water containing 0.23% formic acid) to afford pure example 8 as a pale red solid.

MS (ESI, m/z): 446.1 [(M+H)$^+$].

Example 9

Preparation of (1a-9)

(4S)-4-(10,11-Dihydro-5H-dibenzo[a,d][7]annulen-5-yl)-9-hydroxy-6-methoxy-2-methyl-3,4-dihydro-2H-pyrazino[1,2-c]pyrimidine-1,8-dione

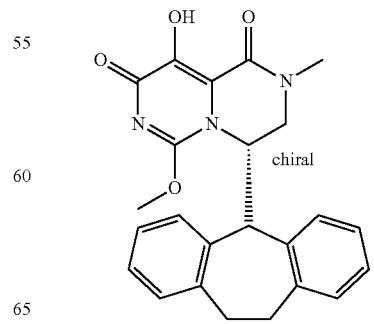

a) 2-((tert-Butoxycarbonyl)amino)-2-(10,11-dihydro-5H-dibenzo[a,d][7]annulen-5-yl)ethyl methanesulfonate

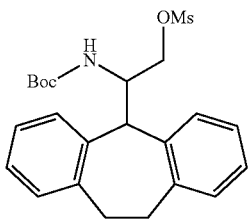 [SMILES: CC(C)(C)OC(=O)NC(COS(C)(=O)=O)C1c2ccccc2CCc2ccccc21]

To a solution of tert-butyl [1-(10,11-dihydro-5H-dibenzo[a,d][7]annulen-5-yl)-2-hydroxyethyl]carbamate (5.0 g, 10 mmol, from example 5d) and triethylamine (2.9 ml, 21 mmol) in tetrahydrofuran (50 ml) was added at 0° C. mesyl-Cl (1.93 g, 17 mmol) and stirring was continued at 20° C. for 1 h. The mixture was evaporated and the residue partitioned between ethyl acetate (100 ml) and diluted aqueous hydrochloric acid. The organic layer was washed with saturated aqueous NaHCO$_3$ solution (50 ml), dried and evaporated to afford the crude title compound (5.8 g) as a white solid.

MS (ESI, m/z): 454.2 [(M+Na)$^+$].

b) tert-Butyl [1-(10,11-dihydro-5H-dibenzo[a,d][7]annulen-5-yl)-2-(methylamino)ethyl]-carbamate (8-9)

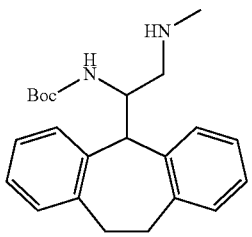 [SMILES: CNCC(NC(=O)OC(C)(C)C)C1c2ccccc2CCc2ccccc21]

A solution of 2-((tert-butoxycarbonyl)amino)-2-(10,11-dihydro-5H-dibenzo[a,d][7]annulen-5-yl)ethyl methanesulfonate 22 (1.0 g, 11 mmol) and MeNH$_2$/ethanol (10 ml, 30%) was heated in a sealed vial (35 ml) in a microwave oven (Biotage Smith Synthesizer) to 90° C. for 2 h. The solution was evaporated to afford the crude title compound (0.86 g) as a colorless oil.

MS (ESI, m/z): 367.2 [(M+H)+].

c) tert-Butyl {2-[(chloroacetyl)(methyl)amino]-1-(10,11-dihydro-5H-dibenzo[a,d][7]annulen-5-yl)ethyl}carbamate (11-9)

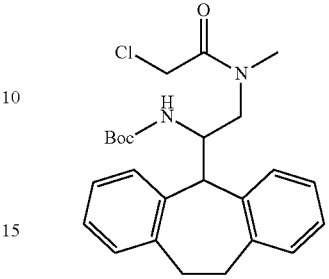

tert-Butyl [1-(10,11-dihydro-5H-dibenzo[a,d][7]annulen-5-yl)-2-(methylamino)ethyl]carbamate was converted according to the procedure described for example 5g to give the crude title compound, which was purified flash chromatography (silica gel, n-heptane/ethyl acetate, 2:1) to afford the title compound as a white solid.

MS (ESI, m/z): 443.2 [(M+H)+].

d) tert-Butyl (2S)-2-(10,11-dihydro-5H-dibenzo[a,d][7]annulen-5-yl)-4-methyl-5-oxopiperazine-1-carboxylate (12-9)

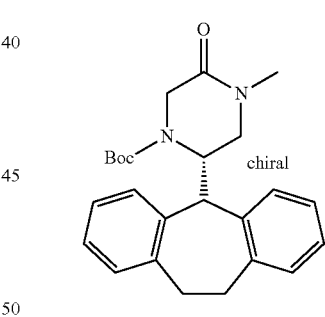

tert-Butyl {2-[(chloroacetyl)(methyl)amino]-1-(10,11-dihydro-5H-dibenzo[a,d][7]annulen-5-yl)ethyl}carbamate was converted according to the procedure described for example 5h to give the racemic title compound, which was resolved by supercritical fluid chromatography (AS, 250×30 mm, 10 μM particle size, EtOH 30%, 0.1% NH$_3$ in water, 100 bar 70% CO$_2$, 35° C.) to give the (2S)-enantiomer as the faster eluting enantiomer.

MS (ESI, m/z): 429.2 [(M+Na)$^+$].

e) (5S)-5-(10,11-Dihydro-5H-dibenzo[a,d][7]annulen-5-yl)-1-methylpiperazin-2-one-hydrogen chloride (13-9)

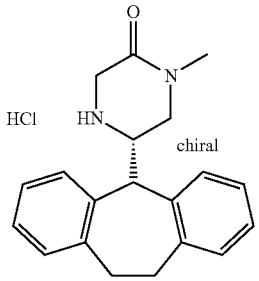 [SMILES: CN1C[C@H](C2c3ccccc3CCc3ccccc32)NCC1=O ; Cl]

tert-Butyl (2S)-2-(10,11-dihydro-5H-dibenzo[a,d][7]annulen-5-yl)-4-methyl-5-oxopiperazine-1-carboxylate was converted according to the procedure described for example 1f to give the title compound as a white solid.
MS (ESI, m/z): 307.2 [(M+H)$^+$].

f) (2S)-2-(10,11-Dihydro-5H-dibenzo[a,d][7]annulen-5-yl)-4-methyl-5-oxopiperazine-1-carbonitrile (14-9)

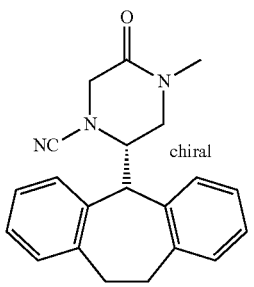 [SMILES: CN1C[C@H](C2c3ccccc3CCc3ccccc32)N(C#N)CC1=O]

(5S)-5-(10,11-Dihydro-5H-dibenzo[a,d][7]annulen-5-yl)-1-methylpiperazin-2-one-hydrogen chloride was converted according to the procedure described for example 1g to give the crude title compound as a yellow oil.
MS (ESI, m/z): 332.3 [(M+H)$^+$].

g) Methyl (2S)-2-(10,11-dihydro-5H-dibenzo[a,d][7]annulen-5-yl)-4-methyl-5-oxopiperazine-1-carboximidate (17-9)

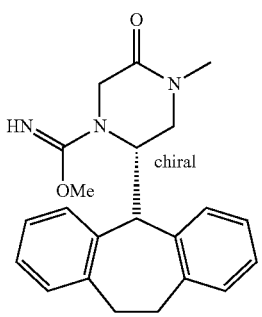 [SMILES: COC(=N)N1CC(=O)N(C)C[C@@H]1C1c2ccccc2CCc2ccccc21]

(2S)-2-(10,11-Dihydro-5H-dibenzo[a,d][7]annulen-5-yl)-4-methyl-5-oxopiperazine-1-carbonitrile was converted according to the procedure described for example 4a to give the crude title compound.
MS (ESI, m/z): 364.2 [(M+H)+].

h) (4S)-4-(10,11-Dihydro-5H-dibenzo[a,d][7]annulen-5-yl)-9-hydroxy-6-methoxy-2-methyl-3,4-dihydro-2H-pyrazino[1,2-c]pyrimidine-1,8-dione (1a-9)

Methyl (2S)-2-(10,11-dihydro-5H-dibenzo[a,d][7]annulen-5-yl)-4-methyl-5-oxopiperazine-1-carboximidate was converted according to the procedure described for example 4b to give crude example 9, which was purified by preparative HPLC (RP-18, acetonitrile/water containing 0.23% formic acid) to give example 9 as a pale red solid.
MS (ESI, m/z): 418.1 [(M+H)$^+$].

Example 10

Preparation of (1a-10)

(4S)-4-(10,11-Dihydro-5H-dibenzo[a,d][7]annulen-5-yl)-6,9-dihydroxy-2-(propan-2-yl)-3,4-dihydro-2H-pyrazino[1,2-c]pyrimidine-1,8-dione

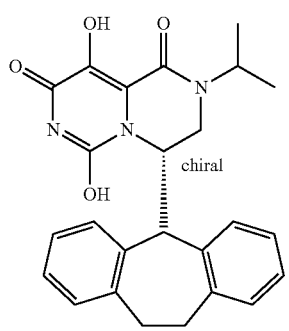 [SMILES: CC(C)N1C[C@H](C2c3ccccc3CCc3ccccc32)n2c(O)nc(=O)c(O)c2C1=O]

(4S)-4-(10,11-Dihydro-5H-dibenzo[a,d][7]annulen-5-yl)-9-hydroxy-6-methoxy-2-(propan-2-yl)-3,4-dihydro-2H-pyrazino[1,2-c]pyrimidine-1,8-dione (example 8) was hydrolyzed according to the procedure described for example 6. The crude title compound was purified by preparative HPLC (RP-18, acetonitrile/water containing 0.23% formic acid) to give example 10 as a white solid.
MS (ESI, m/z): 432.1 [(M+H)$^+$].

Example 11

Preparation of (1a-11)

(4S)-4-(10,11-Dihydro-5H-dibenzo[a,d][7]annulen-5-yl)-6,9-dihydroxy-2-methyl-3,4-dihydro-2H-pyrazino[1,2-c]pyrimidine-1,8-dione

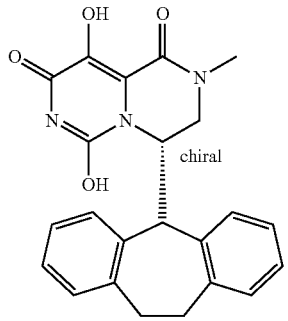 [SMILES: CN1C[C@H](C2c3ccccc3CCc3ccccc32)n2c(O)nc(=O)c(O)c2C1=O]

(4S)-4-(10,11-Dihydro-5H-dibenzo[a,d][7]annulen-5-yl)-9-hydroxy-6-methoxy-2-methyl-3,4-dihydro-2H-pyrazino[1,2-c]pyrimidine-1,8-dione (example 9) was hydrolyzed according to the procedure described for example 6. The crude title compound was purified by preparative HPLC (RP-18, acetonitrile/water containing 0.23% formic acid) to give example 11 as a white solid.

MS (ESI, m/z): 404.1 [(M+H)$^+$].

Example 12

Preparation of (1a-12)

(4S)-4-(10,11-Dihydro-5H-dibenzo[a,d][7]annulen-5-yl)-6-ethoxy-9-hydroxy-2-(propan-2-yl)-3,4-dihydro-2H-pyrazino[1,2-c]pyrimidine-1,8-dione

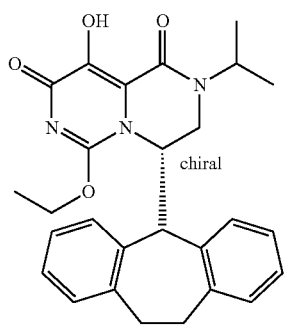 [SMILES: CCOc1nc(=O)c(O)c2n1[C@@H](C1c3ccccc3CCc3ccccc31)CN(C(C)C)C2=O]

a) Ethyl (2S)-2-(10,11-dihydro-5H-dibenzo[a,d][7]annulen-5-yl)-5-oxo-4-(propan-2-yl)-piperazine-1-carboximidate (17-12)

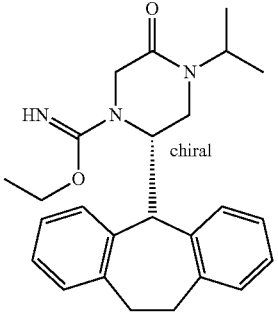 [SMILES: CCOC(=N)N1CC(=O)N(C(C)C)C[C@@H]1C1c2ccccc2CCc2ccccc21]

(2S)-2-(10,11-Dihydro-5H-dibenzo[a,d][7]annulen-5-yl)-5-oxo-4-(propan-2-yl)piperazine-1-carbonitrile from example 5k was converted in analogy to the procedure described for example 8 but using ethanol in step a to give the title compound.

MS (ESI, m/z): 406.2 [(M+H)$^+$].

b) (4S)-4-(10,11-Dihydro-5H-dibenzo[a,d][7]annulen-5-yl)-6-ethoxy-9-hydroxy-2-(propan-2-yl)-3,4-dihydro-2H-pyrazino[1,2-c]pyrimidine-1,8-dione (1a-12)

Ethyl (2S)-2-(10,11-dihydro-5H-dibenzo[a,d][7]annulen-5-yl)-5-oxo-4-(propan-2-yl)piperazine-1-carboximidate was converted according to the procedure described for example 8b to give example 12 as a white solid.

MS (ESI, m/z): 460.2 [(M+H)$^+$].

Example 13

Preparation of (1a-13)

(4S)-4-Benzhydryl-6-benzyloxy-9-hydroxy-2-isopropyl-3,4-dihydropyrazino[1,2-c]pyrimidine-1,8-dione

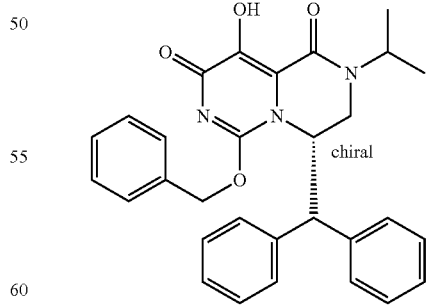

(2S)-2-Benzhydryl-4-isopropyl-5-oxo-piperazine-1-carbonitrile (from example 1g) was converted in analogy to the procedure described for example 4 but using benzyl alcohol in step a to give the title compound.

MS (ESI, m/z): 496.3 [(M+H)$^+$].

Example 14 to 17

Preparation of (1a-14) and separation of its isomers 4-(6,11-dihydrobenzo[c][1]benzothiepin-11-yl)-9-hydroxy-2-isopropyl-6-methoxy-3,4-dihydropyrazino[1,2-c]pyrimidine-1,8-dione

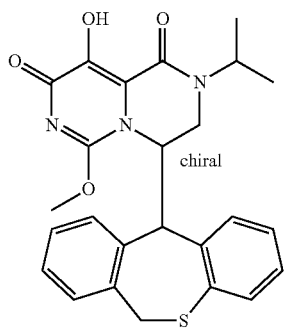 [SMILES: COc1nc(=O)c(O)c2n1C(C1c3ccccc3CSc3ccccc31)CN(C(C)C)C2=O]

a) 2-(6,11-Dihydrobenzo[c][1]benzothiepin-1-yl)-4-isopropyl-5-oxo-piperazine-1-carbonitrile (14-14)

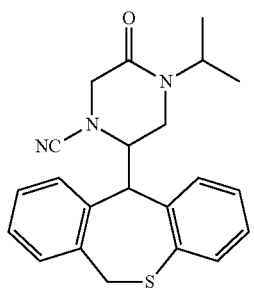 [SMILES: CC(C)N1CC(C2c3ccccc3CSc3ccccc32)N(C#N)CC1=O]

The title compound was prepared according to the procedure described for example 5a-k but using rac-11-chloro-6,11-dihydrobenzo[c][1]benzothiepine in step 5a.

MS (ESI, m/z): 378.2 [(M+H)$^+$].

b) Methyl 2-(6,11-dihydrobenzo[c][1]benzothiepin-11-yl)-4-isopropyl-5-oxo-piperazine-1-carboximidate (17-14)

2-(6,11-Dihydrobenzo[c][1]benzothiepin-11-yl)-4-isopropyl-5-oxo-piperazine-1-carbonitrile was converted according to the procedure described for example 4a to give the title compound.

MS (ESI, m/z): 410.3 [(M+H)$^+$].

c) 4-(6,11-dihydrobenzo[c][1]benzothiepin-11-yl)-9-hydroxy-2-isopropyl-6-methoxy-3,4-dihydropyrazino[1,2-c]pyrimidine-1,8-dione (1a-14)

Methyl 2-(6,11-dihydrobenzo[c][1]benzothiepin-11-yl)-4-isopropyl-5-oxo-piperazine-1-carboximidate was converted according to the procedure described for example 4b to give a mixture of isomers of examples 14 to 17. The mixture of four isomers (1.5 g) was separated by preparative HPLC (phenomenex synergie, C18, 150×30 mm, 4 μm particle size, water containing 0.2% formic acid/acetonitrile) to give a faster (310 mg) and slower eluting (205 mg) fraction.

The faster eluting HPLC-fraction was resolved by supercritical fluid chromatography (AD, 250×30 mm, 5 μm particle size, ethanol 35%, 155 bar 65% CO$_2$, 1% ammonia in water) to give example 14 as the faster eluting fraction (94 mg). MS (ESI, m/z): 464.2 [(M+H)$^+$]. The slower eluting fraction contained example 15 (85 mg). MS (ESI, m/z): 464.2 [(M+H)$^+$].

The slower eluting HPLC-fraction was resolved by supercritical fluid chromatography (AD, 250×30 mm, 5 μm particle size, ethanol 35%, 155 bar 65% CO$_2$, 1% ammonia in water) to give example 16 as the faster eluting fraction (54 mg). MS (ESI, m/z): 464.2 [(M+H)$^+$]. The slower eluting fraction contained example 17 (32 mg). MS (ESI, m/z): 464.2 [(M+H)$^+$].

Based on X-ray analysis, the isomers were identified as follows:

Example 14:
(4S)-4-[(11S)-6,11-dihydrobenzo[c][1]benzothiepin-11-yl]-9-hydroxy-2-isopropyl-6-methoxy-3,4-dihydropyrazino[1,2-c]pyrimidine-1,8-dione

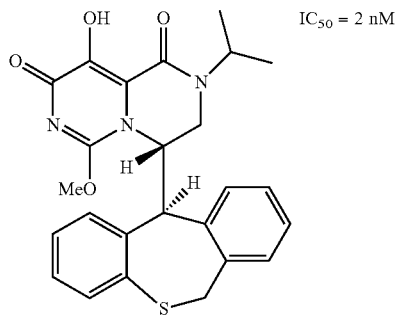

IC$_{50}$ = 2 nM

Example 15: (enantiomer to example 14)
(4R)-4-[(11R)-6,11-dihydrobenzo[c][1]benzothiepin-11-yl]-9-hydroxy-2-isopropyl-6-methoxy-3,4-dihydropyrazino[1,2-c]pyrimidine-1,8-dione

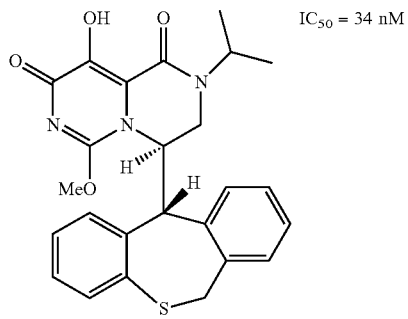

IC$_{50}$ = 34 nM

Example 16:
(4S)-4-[(11R)-6,11-dihydrobenzo[c][1]benzothiepin-11-yl]-9-hydroxy-2-isopropyl-6-methoxy-3,4-dihydropyrazino[1,2-c]pyrimidine-1,8-dione

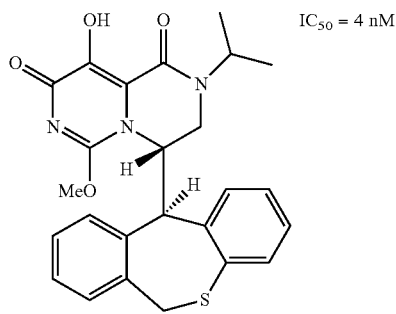

IC$_{50}$ = 4 nM

Example 17: (enantiomer of example 16)
(4R)-4-[(11S)-6,11-dihydrobenzo[c][1]benzothiepin-11-yl]-9-hydroxy-2-isopropyl-6-methoxy-3,4-dihydropyrazino[1,2-c]pyrimidine-1,8-dione

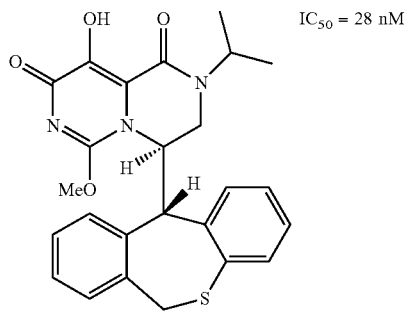

IC$_{50}$ = 28 nM

Example 18

Preparation of (1a-15)

(4S)-4-Benzhydryl-6-butoxy-9-hydroxy-2-isopropyl-3,4-dihydropyrazino[1,2-c]pyrimidine-1,8-dione

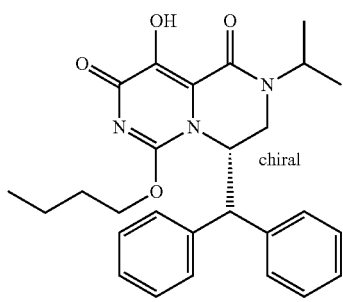 [SMILES: CCCCOc1nc(=O)c(O)c2n1[C@@H](C(c1ccccc1)c1ccccc1)CN(C(C)C)C2=O]

(2S)-2-Benzhydryl-4-isopropyl-5-oxo-piperazine-1-carbonitrile (from example 1g) was converted in analogy to the procedure described for example 4 but using n-butanol in step a to give the title compound.

MS (ESI, m/z): 462.4 [(M+H)$^+$].

Example 19

Preparation of (1a-16)

N-[(4S)-4-Benzhydryl-9-hydroxy-2-isopropyl-1,8-dioxo-3,4-dihydropyrazino[1,2-c]pyrimidin-6-yl]acetamide

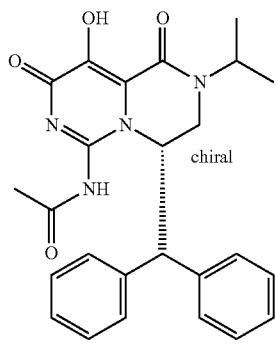 [SMILES: CC(=O)Nc1nc(=O)c(O)c2n1[C@@H](C(c1ccccc1)c1ccccc1)CN(C(C)C)C2=O]

a) N-[(2S)-2-Benzhydryl-4-isopropyl-5-oxo-piperazine-1-carboximidoyl]acetamide (17-16)

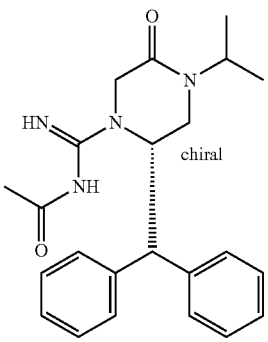 [SMILES: CC(=O)NC(=N)N1CC(=O)N(C(C)C)C[C@@H]1C(c1ccccc1)c1ccccc1]

To a solution of (2S)-2-benzhydryl-4-isopropyl-5-oxo-piperazine-1-carboxamidine (135 mg, 0.4 mmol) from example 3a and triethylamine (76 mg, 0.8 mmol) in dichloromethane (5 ml) was added at 0° C. acetyl chloride (30 mg, 0.4 mmol) and stirring was continued at 0° C. for 30 min. The solution was evaporated to give the title compound as a colorless oil.

MS (ESI, m/z): 393.3 [(M+H)$^+$].

b) N-[(4S)-4-Benzhydryl-9-hydroxy-2-isopropyl-1,8-dioxo-3,4-dihydropyrazino[1,2-c]pyrimidin-6-yl]acetamide (1a-16)

N-[(2S)-2-Benzhydryl-4-isopropyl-5-oxo-piperazine-1-carboximidoyl]acetamide was converted according to the procedure described for example 1i to give example 19 as a white solid.

MS (ESI, m/z): 447.3 [(M+H)$^+$].

Example 20

Preparation of (1a-17)

N-[(4S)-4-benzhydryl-9-hydroxy-2-isopropyl-1,8-dioxo-3,4-dihydropyrazino[1,2-c]-pyrimidin-6-yl]methanesulfonamide

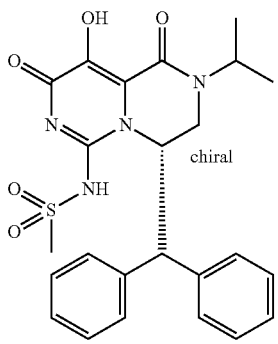 [SMILES: CC(C)N1C[C@H](C(c2ccccc2)c2ccccc2)n2c(NS(C)(=O)=O)nc(=O)c(O)c2C1=O]

a) (2S)-2-Benzhydryl-4-isopropyl-N-methylsulfonyl-5-oxo-piperazine-1-carboxamidine (17-17)

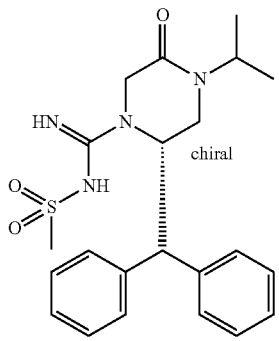 [SMILES: CC(C)N1C[C@H](C(c2ccccc2)c2ccccc2)N(C(=N)NS(C)(=O)=O)CC1=O]

To a solution of (2S)-2-benzhydryl-4-isopropyl-5-oxo-piperazine-1-carboxamidine from example 3a and triethylamine (120 mg, 1.2 mmol) in dichloromethane (5 ml) was added methansulfonyl chloride (220 mg, 1.8 mmol) and stirring was continued at 30° C. for 16 h. The mixture was washed with saturated aqueous NaHCO$_3$ solution and brine, the organic layer was dried, evaporated and the residue purified by preparative HPLC (RP-18, MeCN/H$_2$O containing 0.23% of HCOOH) to give the title compound (60 mg) as a colorless oil.

MS (ESI, m/z): 429.2 [(M+H)$^+$].

b) N-[(4S)-4-benzhydryl-9-hydroxy-2-isopropyl-1,8-dioxo-3,4-dihydropyrazino[1,2-c]-pyrimidin-6-yl]methanesulfonamide (1a-17)

(2S)-2-Benzhydryl-4-isopropyl-N-methylsulfonyl-5-oxo-piperazine-1-carboxamidine was converted according to the procedure described for example 1i to give example 20 as a white solid MS (ESI, m/z): 483.2 [(M+H)$^+$].

Example 21 to 24

Preparation of (1a-18) and separation of its isomers 4-(6,11-Dihydrobenzo[c][1]benzothiepin-11-yl)-9-hydroxy-6-methoxy-2-[(1R)-2,2,2-trifluoro-1-methyl-ethyl]-3,4-dihydropyrazino[1,2-c]pyrimidine-1,8-dione

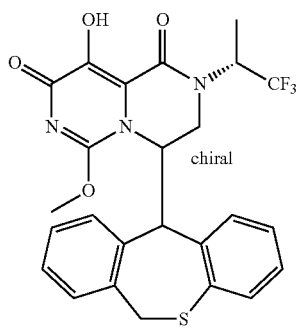 [SMILES: COc1nc(=O)c(O)c2n1C(C1c3ccccc3CSc3ccccc31)CN([C@H](C)C(F)(F)F)C2=O]

The title compound was prepared according to the procedure described for examples 14 to 17 but using (2R)-1,1,1-trifluoropropan-2-amine in step 5f. The mixture of four isomers was separated by preparative HPLC (phenomenex synergie, C18, 150×30 mm, 4 μm particle size, water containing 0.2% formic acid/acetonitrile) to give a faster (190 mg) and slower eluting (205 mg) fraction.

The faster eluting HPLC-fraction was resolved by supercritical fluid chromatography (AS, 250×30 mm, 10 μm particle size, methanol 60%, 150 bar 40% CO$_2$, 1% ammonia in water) to give example 21 as the faster eluting fraction (49 mg). MS (ESI, m/z): 518.2 [(M+H)$^+$]. The slower eluting fraction contained example 22 (46 mg). MS (ESI, m/z): 518.1 [(M+H)$^+$].

The slower eluting HPLC-fraction was resolved by supercritical fluid chromatography (AS, 250×30 mm, 10 μm particle size, methanol 60%, 150 bar 40% CO$_2$, 1% ammonia in water) to give example 23 as the faster eluting fraction (31 mg). MS (ESI, m/z): 518.2 [(M+H)$^+$]. The slower eluting fraction contained example 24 (103 mg). MS (ESI, m/z): 518.2 [(M+H)$^+$].

Example 25 to 28

Preparation of (1a-19) and separation of its isomers 4-(6,11-Dihydrobenzo[c][1]benzothiepin-11-yl)-9-hydroxy-6-methoxy-2-methyl-3,4-dihydropyrazino[1,2-c]pyrimidine-1,8-dione

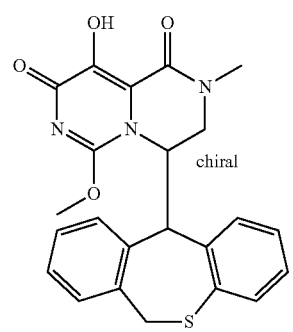 [SMILES: COc1nc(=O)c(O)c2n1C(C1c3ccccc3CSc3ccccc31)CN(C)C2=O]

The title compound was prepared according to the procedure described for examples 14 to 17 but using methylamine in step 5f. The mixture of four isomers (1.8 g) was separated by preparative HPLC (phenomenex synergie, C18, 150×30 mm, 4 μm particle size, water containing 0.2% formic acid/acetonitrile) to give a faster (400 mg) and slower eluting (160 mg) fraction.

The faster eluting HPLC-fraction was resolved by supercritical fluid chromatography (AS, 250×30 mm, 10 μm particle size, methanol 60%, 150 bar 40% CO$_2$, 1% ammonia in water) to give example 25 as the faster eluting fraction (103 mg). MS (ESI, m/z): 436.1 [(M+H)$^+$]. The slower eluting fraction contained example 26 (110 mg). MS (ESI, m/z): 436.1 [(M+H)$^+$].

The slower eluting HPLC-fraction was resolved by supercritical fluid chromatography (AS, 250×30 mm, 10 μm particle size, methanol 60%, 150 bar 40% CO$_2$, 1% ammonia in water) to give example 27 as the faster eluting fraction (15 mg). MS (ESI, m/z): 436.2 [(M+H)$^+$]. The slower eluting fraction contained example 28 (23 mg). MS (ESI, m/z): 436.2 [(M+H)$^+$].

Scheme 2

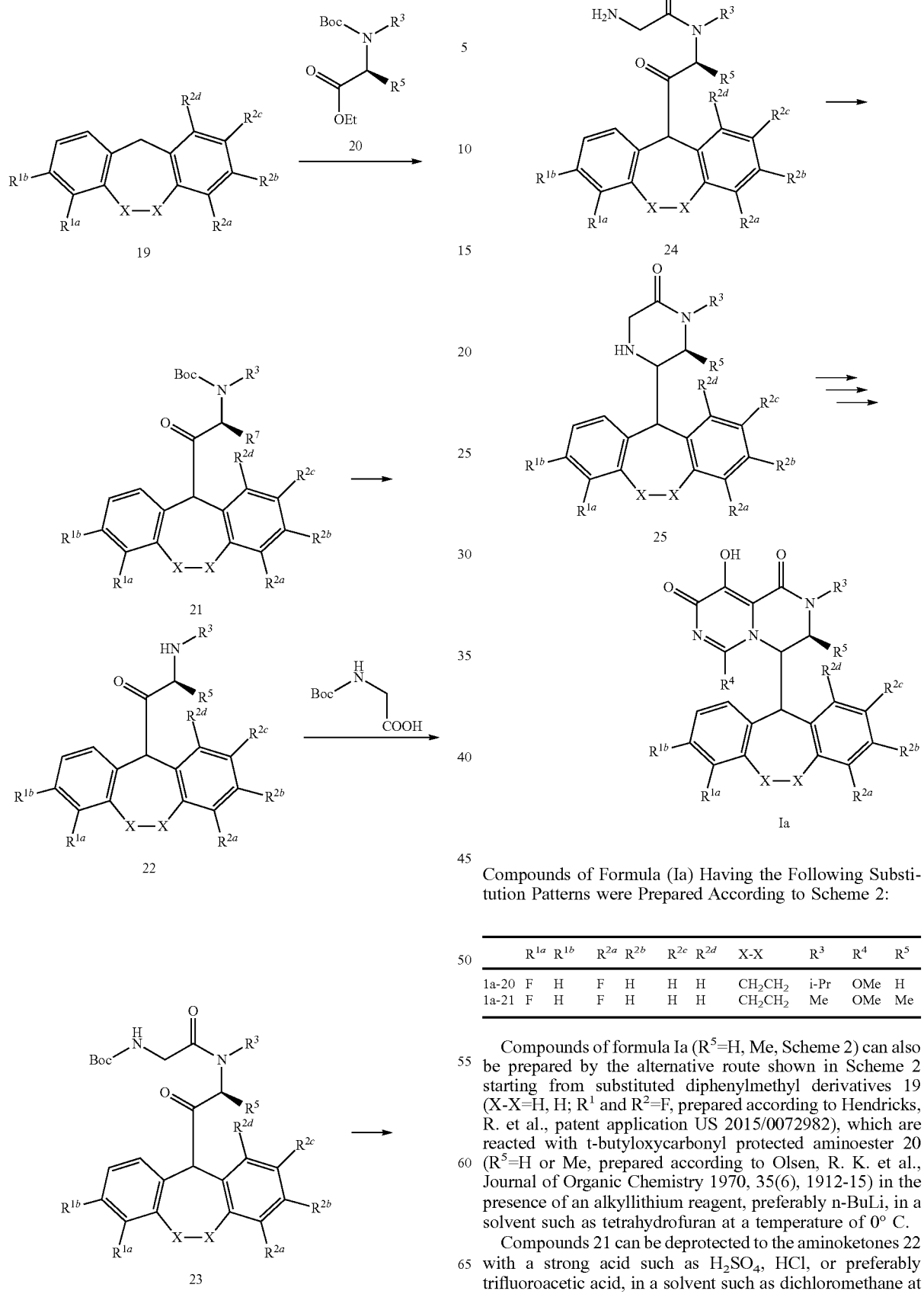

Compounds of Formula (Ia) Having the Following Substitution Patterns were Prepared According to Scheme 2:

| | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| 1a-20 | F | H | F | H | H | H | $CH_2CH_2$ | i-Pr | OMe | H |
| 1a-21 | F | H | F | H | H | H | $CH_2CH_2$ | Me | OMe | Me |

Compounds of formula Ia ($R^5$=H, Me, Scheme 2) can also be prepared by the alternative route shown in Scheme 2 starting from substituted diphenylmethyl derivatives 19 (X-X=H, H; $R^1$ and $R^2$=F, prepared according to Hendricks, R. et al., patent application US 2015/0072982), which are reacted with t-butyloxycarbonyl protected aminoester 20 ($R^5$=H or Me, prepared according to Olsen, R. K. et al., Journal of Organic Chemistry 1970, 35(6), 1912-15) in the presence of an alkyllithium reagent, preferably n-BuLi, in a solvent such as tetrahydrofuran at a temperature of 0° C.

Compounds 21 can be deprotected to the aminoketones 22 with a strong acid such as $H_2SO_4$, HCl, or preferably trifluoroacetic acid, in a solvent such as dichloromethane at 22° C.

Coupling of the aminoketones 22 with t-butyloxycarbonyl-glycine to the amides 23 can be accomplished with an activating agent such as HATU (i.e. [O-(7-azabenzotriazol-1-yl)-N,N,N',N'-tetramethyluronium-hexafluorphosphate]) and a base such as diisopropylethylamine in a solvent such as tetrahydrofuran or preferably dimethylformamide.

Compounds 23 can be deprotected to the amino amides 24 with a strong acid such as $H_2SO_4$, HCl or preferably trifluoroacetic acid in a solvent such as dichloromethane at 0° C.

Reductive amination of the amino amides 24 to afford the piperazinones 25 may be effected with a borohydride reagent, e.g. sodium cyanoborohydride, in the presence of an acid, e.g. acetic acid, in an alcohol as the solvent, preferably methanol, at 0 to 22° C.

Conversion of the piperazinones 25 to compounds of formula Ia can be accomplished in the same manner as described for the conversion of the piperazinones 13 to Ia (Scheme 1).

Example 29

Preparation of (1a-20)

4-(1,9-Difluoro-10,11-dihydro-5H-dibenzo[a,d][7]annulen-5-yl)-9-hydroxy-6-methoxy-2-(propan-2-yl)-3,4-dihydro-2H-pyrazino[1,2-c]pyrimidine-1,8-dione

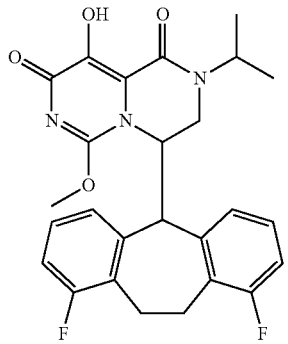 [SMILES: COc1nc(=O)c(O)c2n1C(C1c3cccc(F)c3CCc3c(F)cccc31)CN(C(C)C)C2=O]

a) tert-Butyl (2-(1,9-difluoro-10,11-dihydro-5H-dibenzo[a,d][7]annulen-5-yl)-2-oxoethyl)-(isopropyl)carbamate (21-20)

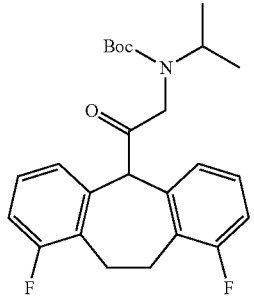 [SMILES: CC(C)N(CC(=O)C1c2cccc(F)c2CCc2c(F)cccc21)C(=O)OC(C)(C)C]

To a solution of 1,9-difluoro-10,11-dihydro-5H-dibenzo[a,d][7]annulene (892 mg, 3.9 mmol, preparation; Hendricks, R. et al., patent application US 2015/0072982) in tetrahydrofuran (50 ml) was added at 0° C. n-BuLi (1.6 M in hexane, 4.5 ml) and stirring was continued at 0° C. for 30 min. A solution of ethyl 2-((tert-butoxycarbonyl)(isopropyl)amino)acetate (840 mg, 3.4 mmol) in tetrahydrofuran (5 ml) was added and stirring was continued for 10 min. The mixture was partitioned between saturated aqueous $NH_4Cl$ and ethyl acetate. The organic layer was dried, evaporated and the residue purified by flash chromatography (silica gel, 0-50% ethyl acetate in n-heptane) to afford the title compound (503 mg) as a red solid.

MS (ESI, m/z): 330.0 [(M-Boc+H)$^+$].

b) 1-(1,9-Difluoro-10,11-dihydro-5H-dibenzo[a,d][7]annulen-5-yl)-2-(isopropylamino)ethanone 2,2,2-trifluoroacetate (22-20)

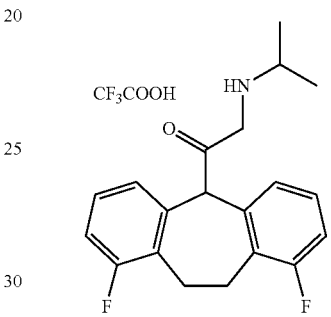

A solution of tert-butyl (2-(1,9-difluoro-10,11-dihydro-5H-dibenzo[a,d][7]annulen-5-yl)-2-oxoethyl)(isopropyl)carbamate (502 mg, 1.2 mmol) and trifluoroacetic acid (7.4 g, 65 mmol) in dichloromethane (5 ml) was stirred at 22° C. for 1.5 h. The solution was evaporated and the residue (518 mg) was used in the next step without purification.

MS (ESI, m/z): 330.0 [(M+H)$^+$].

c) tert-Butyl (2-((2-(1,9-difluoro-10,11-dihydro-5H-dibenzo[a,d][7]annulen-5-yl)-2-oxoethyl)-(isopropyl)amino)-2-oxoethyl)carbamate (23-20)

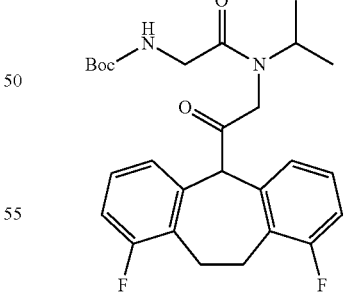

To a solution of 1-(1,9-difluoro-10,11-dihydro-5H-dibenzo[a,d][7]annulen-5-yl)-2-(isopropylamino)ethanone 2,2,2-trifluoroacetate (518 mg, 1.2 mmol) in dimethylformamide (3.5 ml) were subsequently added at 22° C. 2-((tert-butoxycarbonyl)amino)acetic acid (430 mg, 2.45 mmol), diisopropylethylamine (755 mg, 5.84 mmol) and HATU (i.e. [O-(7-azabenzotriazol-1-yl)-N,N,N',N'-tetramethyluronium-hexafluorphosphate], 977 mg, 2.6 mmol) and stirring was continued for 1.5 h. The mixture was evaporated under high vacuum and the residue partitioned between aqueous saturated NaHCO₃ and ethyl acetate. The organic layer was dried, evaporated and the residue (568 mg) was used in the next step without purification.

MS (ESI, m/z): 387.2 [(M-Boc+H)⁺].

d) 2-Amino-N-(2-(1,9-difluoro-10,11-dihydro-5H-dibenzo[a,d][7]annulen-5-yl)-2-oxoethyl)-N-isopropylacetamide 2,2,2-trifluoroacetate (24-20)

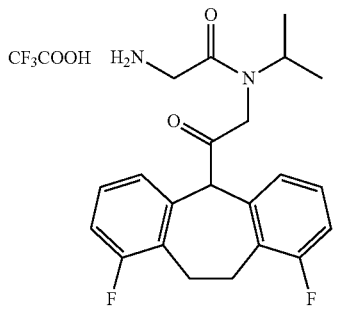 [SMILES: "CF3COOH" ; CC(C)N(CC(=O)C1c2cccc(F)c2CCc2c(F)cccc21)C(=O)CN]

To a solution of tert-butyl (2-((2-(1,9-difluoro-10,11-dihydro-5H-dibenzo[a,d][7]annulen-5-yl)-2-oxoethyl)(isopropyl)amino)-2-oxoethyl)carbamate (568 mg, 1.2 mmol) in dichloromethane (6 ml) was added at 0° C. trifluoroacetic acid (4.5 ml, 58 mmol) and stirring was continued at 0° C. for 15 min. The mixture was evaporated and the residue dried under high vacuum for 15 min. The residue (584 mg) was used in the next step without purification.

MS (ESI, m/z): 387.3 [(M+H)⁺].

e) 5-(1,9-Difluoro-10,11-dihydro-5H-dibenzo[a,d][7]annulen-5-yl)-1-isopropylpiperazin-2-one (25-20)

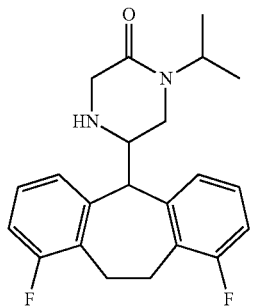 [SMILES: CC(C)N1CC(C2c3cccc(F)c3CCc3c(F)cccc32)NCC1=O]

To a solution of 2-amino-N-(2-(1,9-difluoro-10,11-dihydro-5H-dibenzo[a,d][7]annulen-5-yl)-2-oxoethyl)-N-isopropylacetamide 2,2,2-trifluoroacetate (584 mg, 1.2 mmol) in methanol (12 ml) were subsequently added at 22° C. sodium cyanoborohydride (88 mg, 1.4 mmol) and acetic acid (70 mg, 1.2 mmol) and stirring was continued for 2.5 h. The mixture was partitioned between aqueous saturated NaHCO₃ solution and ethyl acetate. The organic layer was dried, evaporated and the residue (432 mg) was used in the next step without purification.

MS (ESI, m/z): 371.3 [(M+H)⁺].

f) 2-(1,9-Difluoro-10,11-dihydro-5H-dibenzo[a,d][7]annulen-5-yl)-4-isopropyl-5-oxopiperazine-1-carbonitrile (14-20)

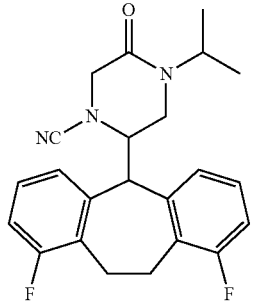 [SMILES: CC(C)N1CC(C2c3cccc(F)c3CCc3c(F)cccc32)N(C#N)CC1=O]

To a solution of 5-(1,9-difluoro-10,11-dihydro-5H-dibenzo[a,d][7]annulen-5-yl)-1-isopropylpiperazin-2-one (432 mg, 1.2 mmol) in dichloromethane (10 ml) were subsequently added at 22° C. diisopropylethylamine (301 mg, 2.3 mmol) and cyanogen bromide (5 M in CH₃CN, 350 µl, 1.75 mmol) and stirring was continued for 1.5 h. A further portion of cyanogen bromide (5 M in CH₃CN, 117 µl, 0.58 mmol) was added and stirring was continued for 45 min. The mixture was partitioned between brine and dichloromethane, the organic layer was dried, evaporated and the residue purified by flash chromatography (silica gel, 0-100% ethyl acetate in n-heptane) to give the title compound (192 mg) as an orange foam.

MS (ESI, m/z): 396.3 [(M+H)⁺].

g) Methyl 2-(1,9-difluoro-10,11-dihydro-5H-dibenzo[a,d][7]annulen-5-yl)-4-isopropyl-5-oxopiperazine-1-carbimidate (17-20)

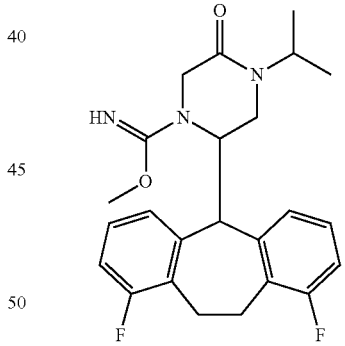

A solution of 2-(1,9-difluoro-10,11-dihydro-5H-dibenzo[a,d][7]annulen-5-yl)-4-isopropyl-5-oxopiperazine-1-carbonitrile (25 mg, 0.063 mmol) and aqueous NaOH (5 M, 40 µl, 0.2 mmol) in methanol (1 ml) was heated to 70° C. for 30 min. The mixture was evaporated and the residue (27 mg) used in the next step without purification.

MS (ESI, m/z): 428.3 [(M+H)⁺].

h) 4-(1,9-Difluoro-10,11-dihydro-5H-dibenzo[a,d][7]annulen-5-yl)-9-hydroxy-6-methoxy-2-(propan-2-yl)-3,4-dihydro-2H-pyrazino[1,2-c]pyrimidine-1,8-dione (1a-20)

Methyl 2-(1,9-difluoro-10,11-dihydro-5H-dibenzo[a,d][7]annulen-5-yl)-4-isopropyl-5-oxopiperazine-1-carbimidate (27 mg) was converted according to the procedure described for example 4b to give the crude example 29, which was purified by preparative HPLC (RP-18, CH₃CN/water containing 0.1% formic acid, gradient) to give pure example 29 (7 mg) as a brown solid.

MS (ESI, m/z): 482.3 [(M+H)⁺].

Example 30

Preparation of (1a-21)

(3S,4S)-4-(1,9-Difluoro-10,11-dihydro-5H-dibenzo[a,d][7]annulen-5-yl)-9-hydroxy-6-methoxy-2,3-dimethyl-3,4-dihydro-2H-pyrazino[1,2-c]pyrimidine-1,8-dione

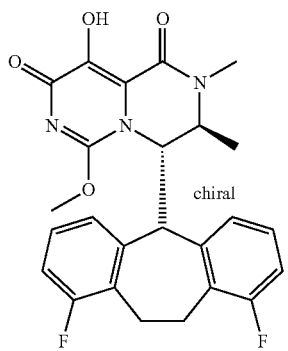 [SMILES: COc1nc(=O)c(O)c2n1[C@@H](C1c3cccc(F)c3CCc3c(F)cccc31)[C@H](C)N(C)C2=O]

a) (S)-tert-Butyl (1-(1,9-difluoro-10,11-dihydro-5H-dibenzo[a,d][7]annulen-5-yl)-1-oxopropan-2-yl)(methyl)carbamate (21-21)

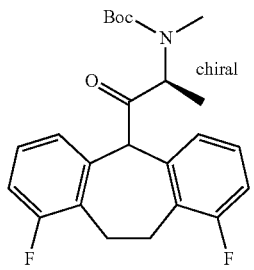 [SMILES: C[C@@H](C(=O)C1c2cccc(F)c2CCc2c(F)cccc21)N(C)C(=O)OC(C)(C)C]

1,9-Difluoro-10,11-dihydro-5H-dibenzo[a,d][7]annulene and (S)-methyl 2-((tert-butoxycarbonyl)(methyl)amino)propanoate (preparation: Olsen, R. K. et al., Journal of Organic Chemistry (1970), 35(6), 1912-15) were reacted according to the procedure described for example 29a to give the title compound as a light yellow oil.

MS (ESI, m/z): 316.2 [(M-Boc)].

b) (S)-1-(1,9-Difluoro-10,11-dihydro-5H-dibenzo[a,d][7]annulen-5-yl)-2-(methylamino)propan-1-one 2,2,2-trifluoroacetate (22-21)

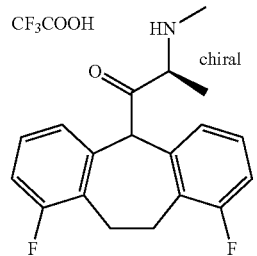 [SMILES: "CF3COOH" ; CN[C@@H](C)C(=O)C1c2cccc(F)c2CCc2c(F)cccc21]

(S)-tert-Butyl (1-(1,9-difluoro-10,11-dihydro-5H-dibenzo[a,d][7]annulen-5-yl)-1-oxopropan-2-yl)(methyl)carbamate was converted according to the procedure described for example 29b to give the title compound as a light brown oil.
MS (ESI, m/z): 316.2 [(M+H)+].

c) (S)-tert-Butyl (2-((1-(1,9-difluoro-10,11-dihydro-5H-dibenzo[a,d][7]annulen-5-yl)-1-oxopropan-2-yl)(methyl)amino)-2-oxoethyl)carbamate (23-21)

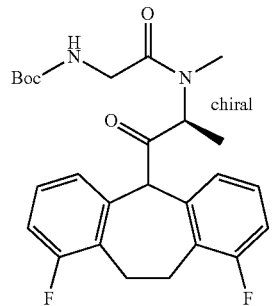 [SMILES: C[C@@H](C(=O)C1c2cccc(F)c2CCc2c(F)cccc21)N(C)C(=O)CNC(=O)OC(C)(C)C]

(S)-1-(1,9-Difluoro-10,11-dihydro-5H-dibenzo[a,d][7]annulen-5-yl)-2-(methylamino)propan-1-one 2,2,2-trifluoroacetate was converted according to the procedure described for example 29c to give the title compound as a colorless oil.
MS (ESI, m/z): 473.2 [(M+H)⁺].

d) (S)-2-Amino-N-(1-(1,9-difluoro-10,11-dihydro-5H-dibenzo[a,d][7]annulen-5-yl)-1-oxopropan-2-yl)-N-methylacetamide 2,2,2-trifluoroacetate (24-21)

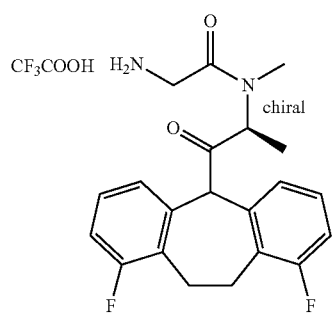 [SMILES: "CF3COOH" ; C[C@@H](C(=O)C1c2cccc(F)c2CCc2c(F)cccc21)N(C)C(=O)CN]

(S)-tert-Butyl (2-((1-(1,9-difluoro-10,11-dihydro-5H-dibenzo[a,d][7]annulen-5-yl)-1-oxopropan-2-yl)(methyl)amino)-2-oxoethyl)carbamate was converted according to the procedure described for example 29d to give the title compound as a colorless oil.

MS (ESI, m/z): 373.2 [(M+H)$^+$].

e) (5S,6S)-5-(1,9-Difluoro-10,11-dihydro-5H-dibenzo[a,d][7]annulen-5-yl)-1,6-dimethylpiperazin-2-one (25-21)

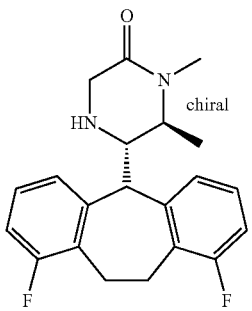 [SMILES: C[C@H]1[C@H](C2c3cccc(F)c3CCc3c(F)cccc32)NCC(=O)N1C]

(S)-2-Amino-N-(1-(1,9-difluoro-10,11-dihydro-5H-dibenzo[a,d][7]annulen-5-yl)-1-oxopropan-2-yl)-N-methylacetamide 2,2,2-trifluoroacetate was converted according to the procedure described for example 29e to give the title compound as a colorless oil.

MS (ESI, m/z): 357.3 [(M+H)$^+$].

f) (2S,3S)-2-(1,9-Difluoro-10,11-dihydro-5H-dibenzo[a,d][7]annulen-5-yl)-3,4-dimethyl-5-oxopiperazine-1-carbonitrile (14-21)

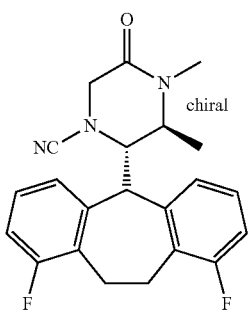 [SMILES: C[C@H]1[C@H](C2c3cccc(F)c3CCc3c(F)cccc32)N(C#N)CC(=O)N1C]

(5S,6S)-5-(1,9-Difluoro-10,11-dihydro-5H-dibenzo[a,d][7]annulen-5-yl)-1,6-dimethylpiperazin-2-one was converted according to the procedure described for example 29f to give the title compound as a light yellow oil.

MS (ESI, m/z): 382.2 [(M+H)+].

g) (2S,3S)-Methyl 2-(1,9-difluoro-10,11-dihydro-5H-dibenzo[a,d][7]annulen-5-yl)-3,4-dimethyl-5-oxopiperazine-1-carbimidate (17-21)

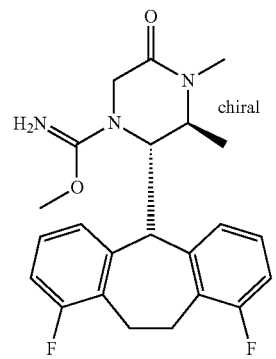 [SMILES: COC(=N)N1CC(=O)N(C)[C@@H](C)[C@@H]1C1c2cccc(F)c2CCc2c(F)cccc21]

(2S,3S)-2-(1,9-Difluoro-10,11-dihydro-5H-dibenzo[a,d][7]annulen-5-yl)-3,4-dimethyl-5-oxopiperazine-1-carbonitrile was converted according to the procedure described for example 29 g to give the title compound as a light yellow foam.

MS (ESI, m/z): 414.3 [(M+H)$^+$].

h) (3S,4S)-4-(1,9-Difluoro-10,11-dihydro-5H-dibenzo[a,d][7]annulen-5-yl)-9-hydroxy-6-methoxy-2,3-dimethyl-3,4-dihydro-2H-pyrazino[1,2-c]pyrimidine-1,8-dione (1a-21)

(2S,3S)-Methyl 2-(1,9-difluoro-10,11-dihydro-5H-dibenzo[a,d][7]annulen-5-yl)-3,4-dimethyl-5-oxopiperazine-1-carbimidate was converted according to the procedure described for example 29 h to give example 30 as a white solid.

MS (ESI, m/z): 468.3 [(M+H)$^+$].

Scheme 3

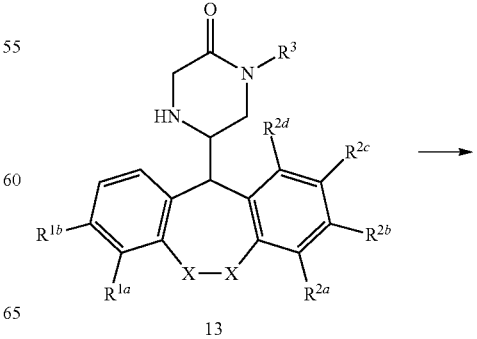

13

-continued

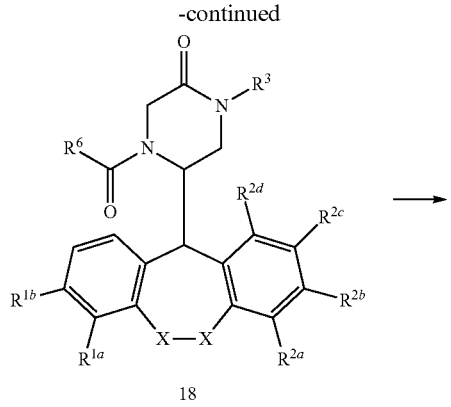

Compounds of Formula (Ib) Having the Following Substitution Patterns were Prepared According to Scheme 3:

|      | $R^{1a}$ | $R^{1b}$ | $R^{2a}$ | $R^{2b}$ | $R^{2c}$ | $R^{2d}$ | X-X | $R^3$ | $R^5$ | $R^7$ |
|------|---|---|---|---|---|---|-----|-------|-------|--------|
| Ib-1 | H | H | H | H | H | H | —   | i-Pr  | H     | Me     |
| Ib-2 | H | H | H | H | H | H | —   | i-Pr  | H     | CH$_2$Ph |

Compounds of formula 18 (R$^6$=NHMe, NHBn) can be prepared by the reaction of the piperazinones 13 with an N-alkylcarbamoyl chloride, specifically with N-methylcarbamoyl chloride or N-benzylcarbamoyl chloride and a base, preferably NaHCO$_3$, in a solvent mixture such as ethyl acetate with water at 0 to 20° C., preferably at 0° C.

Compounds of formula Ib (R$^7$=Me, Bn) are prepared by the reaction of the amides 18 (R$^6$=NHMe, NHBn) and an alkyl oxalate, preferably diethyl oxalate, and a base, preferably lithium hexamethyldisilazide, in an ether as the solvent, preferably tetrahydrofuran, at −78 to −20° C., preferably at −60 to −20° C.

Example 31

Preparation of (1b-1)

(4S)-4-Benzhydryl-9-hydroxy-2-isopropyl-7-methyl-3,4-dihydropyrazino[1,2-c]pyrimidine-1,6,8-trione

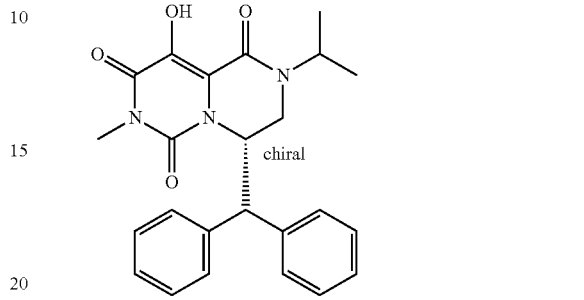

a) (2S)-2-Benzhydryl-4-isopropyl-N-methyl-5-oxo-piperazine-1-carboxamide (18-1)

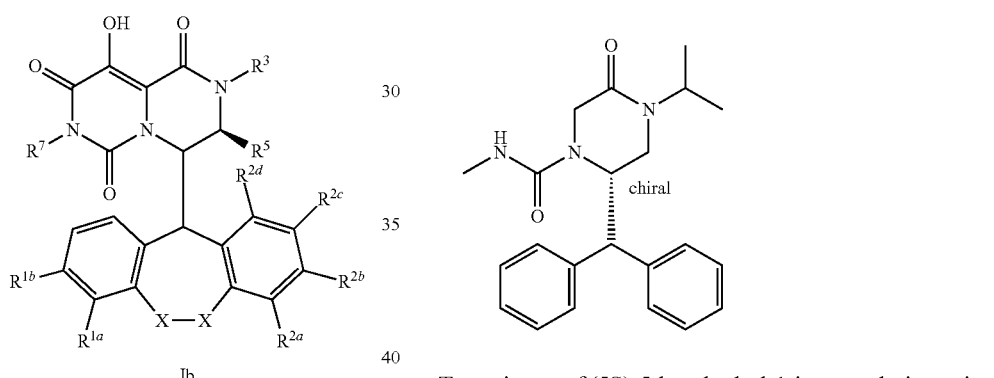

To a mixture of (5S)-5-benzhydryl-1-isopropyl-piperazin-2-one-hydrochloride (from example 1f, 344 mg, 1.0 mmol) and NaHCO$_3$ (252 mg, 3.0 mmol) in ethyl acetate (5 ml) and water (5 ml) was added at 0° C. N-methylcarbamoyl chloride (160 mg, 2.0 mmol) and stirring was continued at 0° C. for 1 h. The layers were separated, the organic layer was washed with brine (20 ml), dried and evaporated to give the crude title compound (400 mg).

MS (ESI, m/z): 366.2 [(M+H)$^+$].

b) (4S)-4-Benzhydryl-9-hydroxy-2-isopropyl-7-methyl-3,4-dihydropyrazino[1,2-c]pyrimidine-1,6,8-trione (1b-1)

To a solution of (S)-2-benzhydryl-4-isopropyl-N-methyl-5-oxo-piperazine-1-carboxamide (400 mg, 1.0 mmol) in tetrahydrofuran (10 ml) were subsequently added at −60° C. lithium hexamethyldisilazide (7.0 ml, 7.0 mmol) and diethyl oxalate (730 mg, 5.0 mmol) and stirring was continued at −60° C. for 1 h. The mixture was evaporated and the residue partitioned between ethyl acetate (20 ml) and aqueous HCl (1N, 20 ml). The organic layer was washed with brine (20 ml), dried and evaporated. The residue was purified by preparative HPLC (RP-18, acetonitrile/water containing 0.23% formic acid) to afford example 31 (35 mg) as a white solid.

MS (ESI, m/z): 420.2 [(M+H)$^+$].

Example 32
Preparation of (1b-2)
(4S)-4-Benzhydryl-7-benzyl-9-hydroxy-2-isopropyl-3,4-dihydropyrazino[1,2-c]pyrimidine-1,6,8-trione
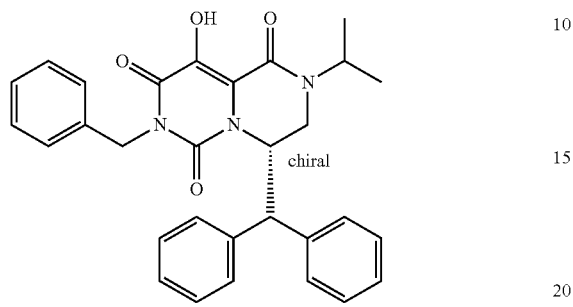
(5S)-5-benzhydryl-1-isopropyl-piperazin-2-one (from example 1f) was converted in analogy to the procedure described for example 31 but using N-benzylcarbamoyl chloride in step a to give the title compound.
MS (ESI, m/z): 496.3 [(M+H)$^+$].

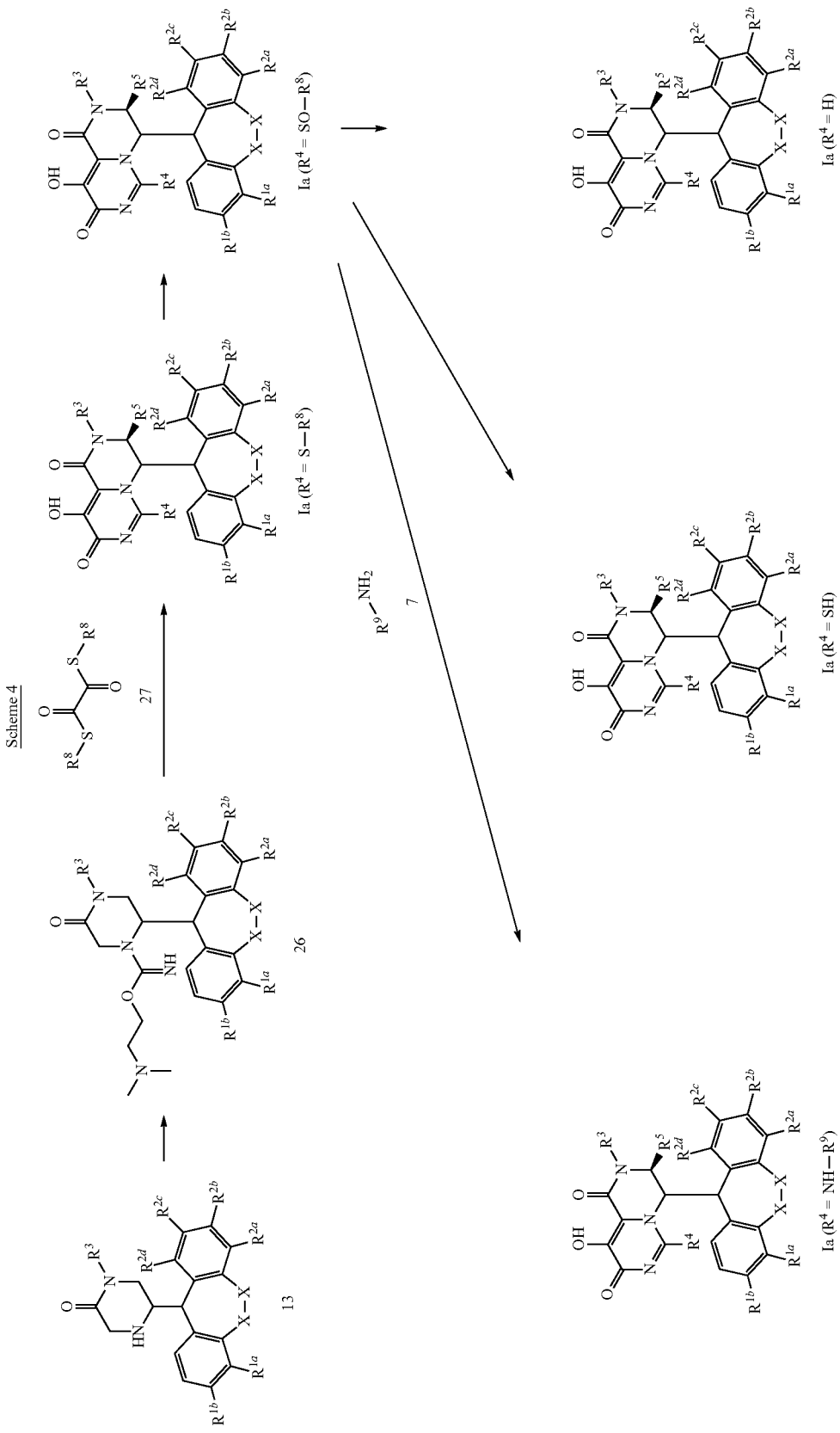

Compounds of Formula (Ia) Having the Following Substitution Patterns were Prepared According to Scheme 4 if not Stated Otherwise:

| | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| 1a-22 | H | H | H | H | H | H | $CH_2CH_2$ | i-Pr | $NHSO_2Me$ | H |
| 1a-23 | H | H | H | H | H | H | — | i-Pr | SMe | H |
| 1a-24 | H | H | H | H | H | H | — | i-Pr | SEt | H |
| 1a-25 | F | H | F | H | H | H | $CH_2CH_2$ | i-Pr | OH | H |
| 1a-26 | H | H | H | H | H | H | — | i-Pr | SOMe | H |
| 1a-27 | H | H | H | H | H | H | — | i-Pr | H | H |
| 1a-28 | H | H | H | H | H | H | — | i-Pr | SH | H |
| 1a-29 | H | H | H | H | H | H | $CH_2CH_2$ | i-Pr | H | H |
| 1a-30 | H | H | H | H | H | H | $CH_2CH_2$ | i-Pr | SMe | H |
| 1a-31 | H | H | H | H | H | H | $CH_2CH_2$ | i-Pr | SOMe | H |
| 1a-32 | H | H | H | H | H | H | — | i-Pr | SOEt | H |
| 1a-33 | H | H | H | H | H | H | — | i-Pr | $NHCH_2CF_3$ | H |
| 1a-34 | H | H | H | H | H | H | $CH_2CH_2$ | i-Pr | $NHCH_2CF_3$ | H |
| 1a-35 | H | H | H | H | H | H | — | i-Pr | NHiPr | H |
| 1a-36 | H | H | H | H | H | H | $CH_2CH_2$ | i-Pr | NHiPr | H |
| 1a-37 | H | H | H | H | H | H | — | i-Pr | $NHCH(CH_3)CF_3$ | H |

According to this pathway, compounds of formula Ia ($R^4$=S—$R^8$, $R^8$ being lower alkyl) can be prepared by reaction of piperazinones 13 with 2-(dimethylamino)ethanol and a base, e.g. sodium hydroxide in a solvent such as water at elevated temperature, preferably at 100° C. to give the intermediate isourea derivatives 26.

Isoureas 26 can be reacted with an S1,S2-dialkyl ethanebis(thioate) and a base, preferably lithium hexamethyldisilazide in a solvent such as ethers, preferably tetrahydrofuran at low temperature, preferably at −50° C. to 0° C. to give compounds of formula Ia ($R^4$=S—$R^8$, $R^8$ being lower alkyl).

Compounds of formula Ia ($R^4$=SO—$R^8$, $R^8$ being lower alkyl) might be prepared from compounds of formula Ia ($R^4$=S—$R^8$, $R^8$ being lower alkyl) and a perbenzoic acid, e.g. m-chloroperbenzoic acid in a solvent such as dichloromethane at room temperature and running the reaction for a few hours.

Compounds of formula Ia ($R^4$=H) can be prepared from compounds of formula Ia ($R^4$=SO—$R^8$, $R^8$ being lower alkyl) and an alkylmagnesium halogenide, preferable methylmagnesium bromide in a solvent such as ethers, preferably tetrahydrofuran at low temperature, e.g. at −60° C.

Compounds of formula Ia ($R^4$=SH) can be prepared from compounds of formula Ia ($R^4$=SO—$R^8$, $R^8$ being lower alkyl) and sodium hydrosulfide in a solvent such as a formamide, preferably dimethylformamide at elevated temperature, e.g. at 110° C.

Compounds of formula Ia ($R^4$=NH—$R^9$, $R^9$ being lower alkyl or lower fluoroalkyl) can be prepared from compounds of formula Ia ($R^4$=SO—$R^8$, $R^8$ being lower alkyl) and an alkyl amine or fluoroalkyl amine and a base, preferably lithium hexamethyldisilazide in a solvent such as tetrahydrofuran at 0-110° C.

Example 33

Preparation of (1a-22): (Prepared according to Scheme 1)

N-[(4S)-4-(6,11-dihydro-5H-dibenzo[1,2-a:2',1'-d][7]annulen-11-yl)-9-hydroxy-2-isopropyl-1,8-dioxo-3,4-dihydropyrazino[1,2-c]pyrimidin-6-yl]methanesulfonamide

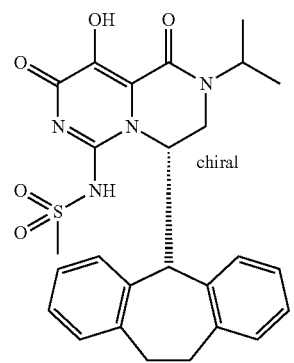 [SMILES: CC(C)N1C[C@H](C2c3ccccc3CCc3ccccc32)n2c(NS(C)(=O)=O)nc(=O)c(O)c2C1=O]

(2S)-2-(10,11-Dihydro-5H-dibenzo[a,d][7]annulen-5-yl)-5-oxo-4-(propan-2-yl)piperazine-1-carboximidamide (from example 51) was converted according to the procedure described for example 20 to give the title compound as a white solid.

MS (ESI, m/z): 509.1 [(M+H)⁺].

Example 34

Preparation of (1a-23)

(4S)-4-Benzhydryl-9-hydroxy-2-isopropyl-6-methyl-sulfanyl-3,4-dihydropyrazino[1,2-c]pyrimidine-1,8-dione

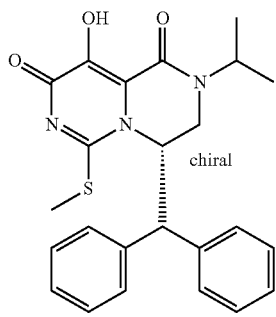 [SMILES: CSc1nc(=O)c(O)c2n1[C@@H](C(c1ccccc1)c1ccccc1)CN(C(C)C)C2=O]

a) 2-(Dimethylamino)ethyl (2S)-2-benzhydryl-4-isopropyl-5-oxo-piperazine-1-carboximidate

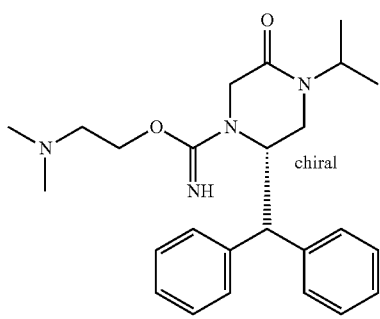 [SMILES: CC(C)N1C[C@H](C(c2ccccc2)c2ccccc2)N(C(=N)OCCN(C)C)CC1=O]

To a solution of (2S)-2-benzhydryl-4-isopropyl-5-oxo-piperazine-1-carbonitrile (500 mg, from example 1g) in dimethylformamide (5 ml) was added 2-(dimethylamino) ethanol (268 mg) and a aqueous solution of NaOH (20%, 0.6 ml) and stirring was continued at reflux temperature for 1 h. The solution was partitioned between brine and ethyl acetate, the organic layer was dried and evaporated to give the crude title compound (580 mg) as a light yellow oil.

MS (ESI, m/z): 423.3 [(M+H)$^+$].

b) To a solution of 2-(dimethylamino)ethyl (2S)-2-benzhydryl-4-isopropyl-5-oxo-piperazine-1-carboximidate (1.5 g) in tetrahydrofuran (30 ml) were subsequently added at −50° C. lithium hexamethyldisilazide (1 M, 30 ml) and S1,S2-dimethyl ethanebis(thioate) (900 mg, preparation: Marzorati, L. et al., Journal of Sulfur Chemistry (2014), 35(3), 248-260) and stirring was continued at −50° C. for 0.5 h and at 0° C. for 0.5 h. The mixture was partitioned between aqueous HCl (0.5 N, 100 ml) and ethyl acetate (2×100 ml), the organic layers were dried, evaporated and the residue purified by preparative HPLC (phenomenex synergie, C18, 150×30 mm, 4 µm particle size, water containing 0.2% formic acid/acetonitrile) to give example 34 (260 mg) as a white solid.

MS (ESI, m/z): 436.2 [(M+H)$^+$].

Example 35

Preparation of (1a-24)

(4S)-4-Benzhydryl-6-ethylsulfanyl-9-hydroxy-2-isopropyl-3,4-dihydropyrazino[1,2-c]pyrimidine-1,8-dione

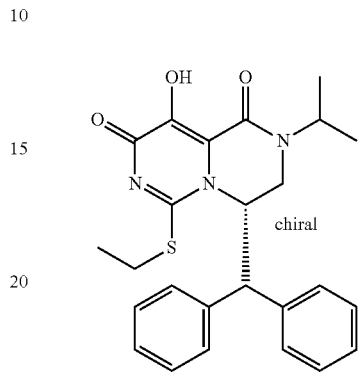

2-(Dimethylamino)ethyl (2S)-2-benzhydryl-4-isopropyl-5-oxo-piperazine-1-carboximidate (from example 34a) was converted according to the procedure described for example 34b but using S-ethyl 3-methylsulfanyl-2-oxo-propanethioate (prepared according to Aichenegg, P. C. et al., U.S. Pat. No. 3,428,665) to give the title compound as a yellow liquid.

MS (ESI, m/z): 450.3 [(M+H)$^+$].

Example 36

Preparation of (1a-25): (Prepared according to Scheme 1)

4-(4,7-Difluoro-6,11-dihydro-5H-dibenzo[1,3-b:3',1'-e][7]annulen-11-yl)-6,9-dihydroxy-2-isopropyl-3,4-dihydropyrazino[1,2-c]pyrimidine-1,8-dione

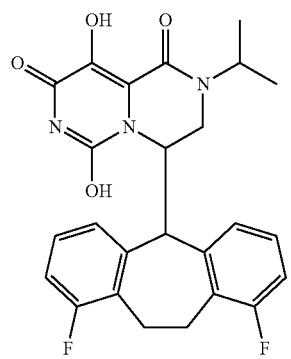 [SMILES: CC(C)N1CC(C2c3cccc(F)c3CCc3c(F)cccc32)n2c(O)nc(=O)c(O)c2C1=O]

4-(1,9-Difluoro-10,11-dihydro-5H-dibenzo[a,d][7]annulen-5-yl)-9-hydroxy-6-methoxy-2-(propan-2-yl)-3,4-dihydro-2H-pyrazino[1,2-c]pyrimidine-1,8-dione from example 29 was hydrolyzed according to example 6 to give the title compound as a white solid.

MS (ESI, m/z): 468.2 [(M+H)$^+$].

Example 37

Preparation of (1a-26)

(4S)-4-Benzhydryl-9-hydroxy-2-isopropyl-6-methyl-sulfinyl-3,4-dihydropyrazino[1,2-c]pyrimidine-1,8-dione

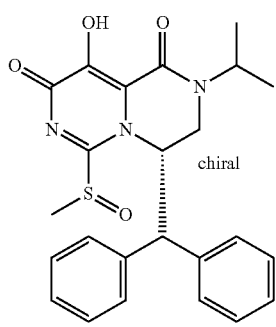 [SMILES: CC(C)N1C[C@H](C(c2ccccc2)c2ccccc2)n2c(S(C)=O)nc(=O)c(O)c2C1=O]

To a solution of (4S)-4-benzhydryl-9-hydroxy-2-isopropyl-6-methylsulfanyl-3,4-dihydropyrazino[1,2-c]pyrimidine-1,8-dione (from example 34, 260 mg) in dichloromethane (30 ml) was added at 0° C. m-chloroperbenzoic acid (516 mg)) and stirring was continued at 25° C. for 1 h. The mixture was washed with brine, the organic layer dried, evaporated and the residue purified by preparative HPLC (phenomenex synergie, C18, 150×30 mm, 4 μm particle size, water containing 0.2% formic acid/acetonitrile) to give example 37 (170 mg) as a white solid.
MS (ESI, m/z): 452.1 [(M+H)+].

Example 38

Preparation of (1a-27)

(4S)-4-Benzhydryl-9-hydroxy-2-isopropyl-3,4-dihydropyrazino[1,2-c]pyrimidine-1,8-dione

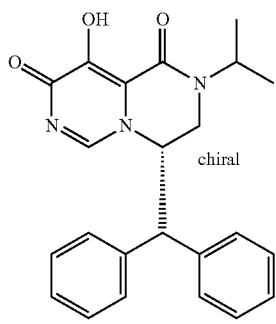 [SMILES: CC(C)N1C[C@H](C(c2ccccc2)c2ccccc2)n2cnc(=O)c(O)c2C1=O]

To a solution of (4S)-4-benzhydryl-9-hydroxy-2-isopropyl-6-methylsulfinyl-3,4-dihydropyrazino[1,2-c]pyrimidine-1,8-dione (30 mg, from example 37) in tetrahydrofuran (2 ml) was added at −60° C. MeMgBr (3 M in THF, 0.07 ml) and stirring was continued at −60° C. for 0.5 h. The mixture was partitioned between aqueous hydrochloric acid (1N) and ethyl acetate, the organic layer was dried, evaporated and the residue purified by preparative HPLC (phenomenex synergie, C18, 150×30 mm, 4 μm particle size, water containing 0.2% formic acid/acetonitrile) to give example 38 (3 mg) as a white solid.
MS (ESI, m/z): 390.3 [(M+H)+].

Example 39

Preparation of (1a-28)

(4S)-4-benzhydryl-9-hydroxy-2-isopropyl-6-sulfanyl-3,4-dihydropyrazino[1,2-c]pyrimidine-1,8-dione

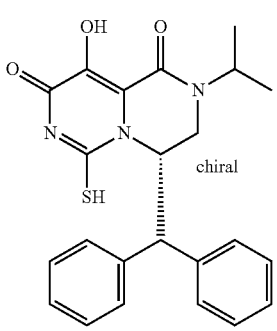 [SMILES: CC(C)N1C[C@H](C(c2ccccc2)c2ccccc2)n2c(S)nc(=O)c(O)c2C1=O]

In a sealed vial (12 ml) a mixture of (4S)-4-benzhydryl-9-hydroxy-2-isopropyl-6-methylsulfinyl-3,4-dihydropyrazino[1,2-c]pyrimidine-1,8-dione (from example 37) and NaSH (78 mg) in dimethylformamide (3 ml) was heated in a microwave oven (Biotage Smith Synthesizer) to 110° C. for 2 h. The mixture was partitioned between brine and ethyl acetate, the organic layer was dried, evaporated and the residue purified by preparative HPLC (phenomenex synergie, C18, 150×30 mm, 4 μm particle size, water containing 0.2% formic acid/acetonitrile) to give example 39 (7 mg) as a yellow solid.
MS (ESI, m/z): 422.1 [(M+H)+].

Example 40

Preparation of (1a-29)

(4S)-4-(6,11-Dihydro-5H-dibenzo[2,1-b:1',2'-e][7]annulen-11-yl)-9-hydroxy-2-isopropyl-3,4-dihydropyrazino[1,2-c]pyrimidine-1,8-dione

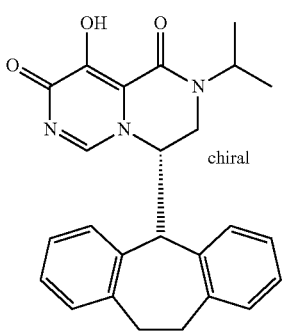 [SMILES: CC(C)N1C[C@H](C2c3ccccc3CCc3ccccc32)n2cnc(=O)c(O)c2C1=O]

The title compound was prepared in analogy to example 38 to give the compound as a white solid.
MS (ESI, m/z): 416.3 [(M+H)+].

Example 41

Preparation of (1a-30)

(4S)-4-(6,11-Dihydro-5H-dibenzo[2,1-b:1',2'-e][7]annulen-11-yl)-9-hydroxy-2-isopropyl-6-methylsulfanyl-3,4-dihydropyrazino[1,2-c]pyrimidine-1,8-dione

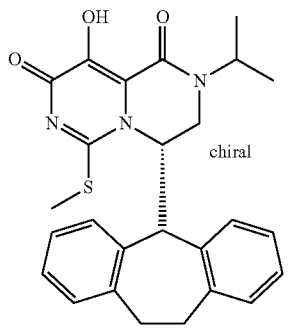 [SMILES: CSc1nc(=O)c(O)c2n1[C@@H](C1c3ccccc3CCc3ccccc31)CN(C(C)C)C2=O]

The title compound was prepared in analogy to example 34 to give the compound as a white solid.
MS (ESI, m/z): 462.2 [(M+H)⁺].

Example 42

Preparation of (1a-31)

(4S)-4-(6,11-Dihydro-5H-dibenzo[2,1-b:1',2'-e][7]annulen-11-yl)-9-hydroxy-2-isopropyl-6-methylsulfinyl-3,4-dihydropyrazino[1,2-c]pyrimidine-1,8-dione

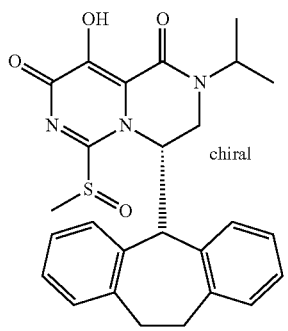 [SMILES: CC(C)N1C[C@H](C2c3ccccc3CCc3ccccc32)n2c(S(C)=O)nc(=O)c(O)c2C1=O]

The title compound was prepared in analogy to example 37 to give the compound as a white solid.
MS (ESI, m/z): 478.2 [(M+H)⁺].

Example 43

Preparation of (1a-32)

(4S)-4-Benzhydryl-6-ethylsulfinyl-9-hydroxy-2-isopropyl-3,4-dihydropyrazino[1,2-c]pyrimidine-1,8-dione

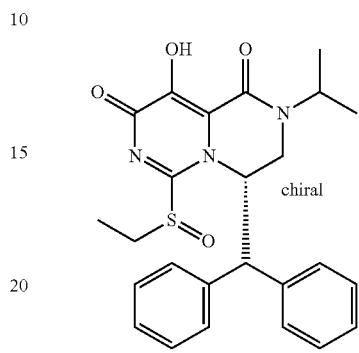

(4S)-4-Benzhydryl-6-ethylsulfanyl-9-hydroxy-2-isopropyl-3,4-dihydropyrazino[1,2-c]pyrimidine-1,8-dione (from example 35) was converted according to the procedure described for example 37 to give the title compound as a yellow liquid.
MS (ESI, m/z): 466.1 [(M+H)⁺].

Example 44

Preparation of (1a-33)

(4S)-4-Benzhydryl-9-hydroxy-2-isopropyl-6-(2,2,2-trifluoroethylamino)-3,4-dihydropyrazino[1,2-c]pyrimidine-1,8-dione

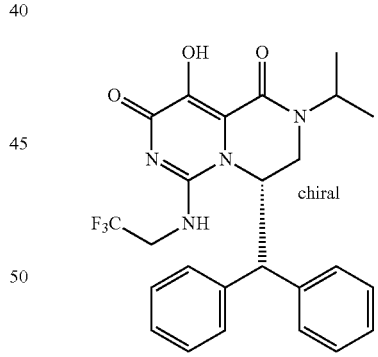

To a solution of (4S)-4-benzhydryl-9-hydroxy-2-isopropyl-6-methylsulfinyl-3,4-dihydropyrazino[1,2-c]pyrimidine-1,8-dione (from example 37, 50 mg) and trifluoroethylamine (0.2 ml) in tetrahydrofuran (20 ml) was added at 0° C. lithium hexamethyldisilazide (1 M, 0.3 ml) and stirring was continued at 0° C. for 1 h. The mixture was partitioned between aqueous hydrochloric acid (1 N) and ethyl acetate, the organic layer was dried, evaporated and the residue purified by preparative HPLC (phenomenex synergie, C18, 150×30 mm, 4 μm particle size, water containing 0.2% formic acid/acetonitrile) to give the title compound (27 mg) as a white solid.
MS (ESI, m/z): 487.2 [(M+H)⁺].

Example 45

Preparation of (1a-34)

(4S)-4-(6,11-Dihydro-5H-dibenzo[2,1-b:1',2'-e][7]annulen-11-yl)-9-hydroxy-2-isopropyl-6-(2,2,2-trifluoroethylamino)-3,4-dihydropyrazino[1,2-c]pyrimidine-1,8-dione

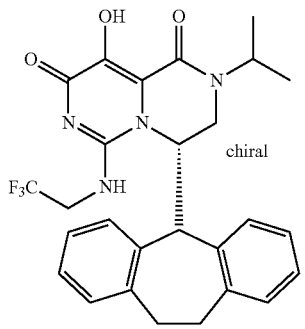 [SMILES: CC(C)N1C[C@H](C2c3ccccc3CCc3ccccc32)n2c(NCC(F)(F)F)nc(=O)c(O)c2C1=O]

(4S)-4-(6,11-Dihydro-5H-dibenzo[2,1-b:1',2'-e][7]annulen-11-yl)-9-hydroxy-2-isopropyl-6-methylsulfinyl-3,4-dihydropyrazino[1,2-c]pyrimidine-1,8-dione (from example 42) was converted according to the procedure described for example 44 to give the title compound as a white solid.
MS (ESI, m/z): 513.1 [(M+H)$^+$].

Example 46

Preparation of (1a-35)

(4S)-4-Benzhydryl-9-hydroxy-2-isopropyl-6-(isopropylamino)-3,4-dihydropyrazino[1,2-c]pyrimidine-1,8-dione

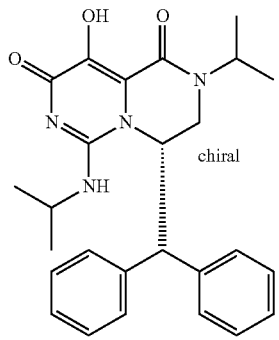 [SMILES: CC(C)Nc1nc(=O)c(O)c2n1[C@@H](C(c1ccccc1)c1ccccc1)CN(C(C)C)C2=O]

In a sealed vial (10 ml), a solution of (4S)-4-benzhydryl-9-hydroxy-2-isopropyl-6-methylsulfinyl-3,4-dihydropyrazino[1,2-c]pyrimidine-1,8-dione (from example 37, 25 mg) and isopropylamine was heated in a microwave oven to 110° C. for 2 h. The mixture was evaporated and the residue purified by preparative HPLC (phenomenex synergie, C18, 150×30 mm, 4 µm particle size, water containing 0.2% formic acid/acetonitrile) to give the title compound (11 mg) as a white solid.
MS (ESI, m/z): 447.3 [(M+H)$^+$].

Example 47

Preparation of (1a-36)

(4S)-4-(6,11-Dihydro-5H-dibenzo[2,1-b:1',2'-e][7]annulen-11-yl)-9-hydroxy-2-isopropyl-6-(isopropylamino)-3,4-dihydropyrazino[1,2-c]pyrimidine-1,8-dione

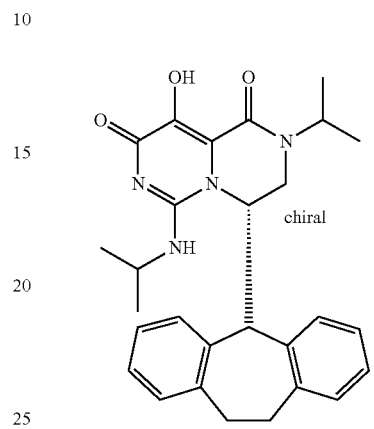

(4S)-4-(6,11-Dihydro-5H-dibenzo[2,1-b:1',2'-e][7]annulen-11-yl)-9-hydroxy-2-isopropyl-6-methylsulfinyl-3,4-dihydropyrazino[1,2-c]pyrimidine-1,8-dione (from example 42) was converted according to the procedure described for example 46 to give the title compound as a white solid.
MS (ESI, m/z): 473.3 [(M+H)$^+$].

Example 48

Preparation of (1a-37)

(4S)-4-Benzhydryl-9-hydroxy-2-isopropyl-6-[(2,2,2-trifluoro-1-methyl-ethyl)amino]-3,4-dihydropyrazino[1,2-c]pyrimidine-1,8-dione

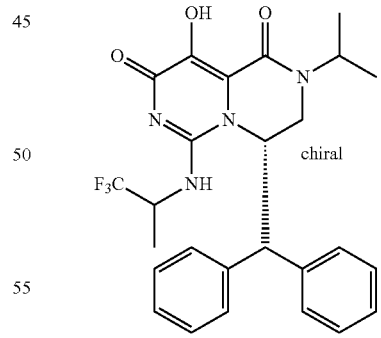

(4S)-4-Benzhydryl-9-hydroxy-2-isopropyl-6-methylsulfinyl-3,4-dihydropyrazino[1,2-c]pyrimidine-1,8-dione (from example 37) was converted according to the procedure described for example 44 but using trifluroisopropylamine hydrochloride to give the title compound as a yellow solid.
MS (ESI, m/z): 501.3 [(M+H)$^+$].

Compounds of Formula (Ia) Having the Following Substitution Patterns were Prepared According to Scheme 5:

Scheme 5

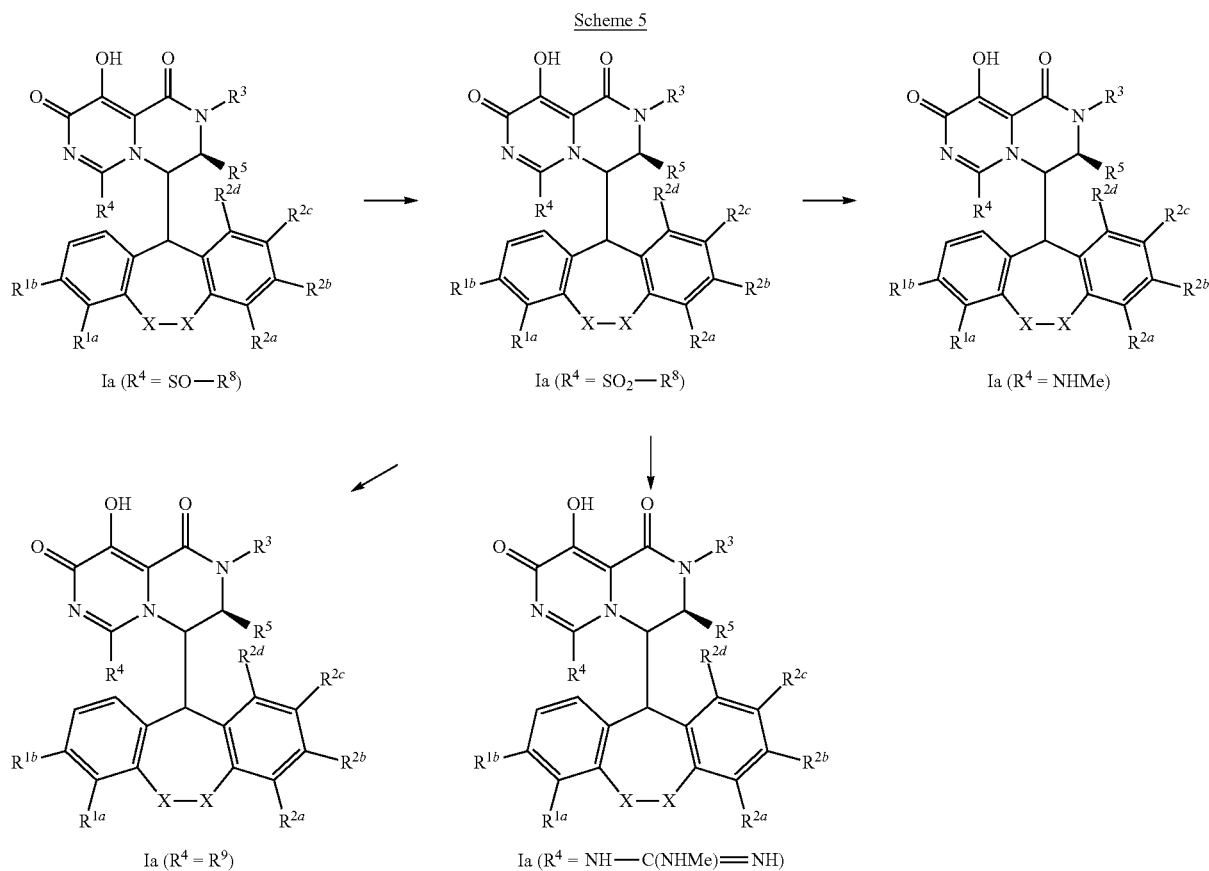

|  | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| 1a-38 | H | H | H | H | H | H | — | i-Pr | SO₂Me | H |
| 1a-39 | H | H | H | H | H | H | — | i-Pr | SO₂Et | H |
| 1a-40 | H | H | H | H | H | H | — | i-Pr | Me | H |
| 1a-41 | H | H | H | H | H | H | — | i-Pr | Et | H |
| 1a-42 | H | H | H | H | H | H | — | i-Pr | Ph | H |
| 1a-43 | H | H | H | H | H | H | — | i-Pr | Imidazol-1-yl | H |
| 1a-44 | H | H | H | H | H | H | — | i-Pr | 1,2,4-Triazol-4-yl | H |
| 1a-45 | H | H | H | H | H | H | CH=CH₂ | i-Pr | Imidazol-1-yl | H |
| 1a-46 | H | H | H | H | H | H | CH₂CH₂ | i-Pr | 1,2,4-Triazol-4-yl | H |
| 1a-47 | H | H | H | H | H | H | CH₂CH₂ | i-Pr | CH=CH₂ | H |
| 1a-48 | H | H | H | H | H | H | CH₂CH₂ | i-Pr | CH₂OH | H |
| 1a-49 | H | H | H | H | H | H | — | i-Pr | NHMe | H |
| 1a-50 | H | H | H | H | H | H | — | i-Pr | NHC(NMe)=NH | H |

According to this pathway, compounds of formula Ia ($R^4$=SO₂—$R^8$) can be prepared from compounds of formula Ia ($R^4$=SO—$R^8$, $R^8$ being lower alkyl) and a perbenzoic acid, e.g. m-chloroperbenzoic acid in a solvent such as dichloromethane at room temperature and running the reaction for 1-3 days.

Compounds of formula Ia ($R^4$=$R^9$, $R^9$ being alkyl, alkenyl or aryl) can be prepared from compounds of formula Ia ($R^4$=SO—$R^8$, $R^8$ being lower alkyl) and an alkyl, alkenyl or aryl magnesium bromide in a solvent such as ethers, preferably diethyl ether, at 0° C.

Compounds of formula Ia ($R^4$=$R^9$, $R^9$ being heterocycles) can be prepared from compounds of formula Ia ($R^4$=SO—$R^8$, $R^8$ being lower alkyl) and a heterocycle, e.g. an imidazole or a triazole and a base, e.g. potassium carbonate in a solvent such as acetonitrile at elevated temperature e.g. at 70° C.

Compounds of formula Ia ($R^4$=$R^9$, $R^9$ being hydroxymethyl) can be prepared from compounds of formula Ia ($R^4$=SO—$R^8$, $R^8$ being lower alkyl) and an alkoxycarbonylmethyl magnesium halogenide in a solvent such as tetrahydrofuran at −65-20° C. The intermediate compound of formula Ia ($R^4$=$R^9$, $R^9$ being t-BuCOOCH₂) can be deprotected with a base, e.g. potassium carbonate in a solvent such an alcohol, preferably methanol at room temperature.

Compounds of formula Ia ($R^4$=NHMe) can be prepared from compounds of formula Ia ($R^4$=SO—$R^8$, $R^8$ being lower alkyl) and an amine, e.g. methylamine and a base such as diisopropylethylamine at elevated temperature, preferably in a microwave oven at 110° C.

Compounds of formula Ia (R$^4$=NHC(NMe)=NH) can be prepared from compounds of formula Ia (R$^4$=SO—R$^8$, R$^8$ being lower alkyl) and a guanidine, e.g. 1-methylguanidine hydrochloride and a base such as potassium carbonate in a solvent like dimethylformamide at 60° C.

Example 49

Preparation of (1a-38)

(4S)-4-Benzhydryl-9-hydroxy-2-isopropyl-6-methylsulfonyl-3,4-dihydropyrazino[1,2-c]pyrimidine-1,8-dione

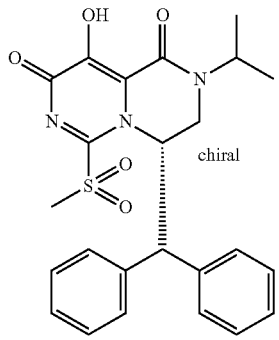 [SMILES: CC(C)N1C[C@H](C(c2ccccc2)c2ccccc2)n2c(S(C)(=O)=O)nc(=O)c(O)c2C1=O]

To a solution of ((4S)-4-benzhydryl-9-hydroxy-2-isopropyl-6-methylsulfinyl-3,4-dihydropyrazino[1,2-c]pyrimidine-1,8-dione (from example 37, 100 mg) in dichloromethane (5 ml) was added at 0° C. m-chloroperbenzoic acid (345 mg)) and stirring was continued at 25° C. for 16 h. The mixture was washed with brine, the organic layer dried, evaporated and the residue purified by preparative HPLC (phenomenex synergie, C18, 150×30 mm, 4 μm particle size, water containing 0.2% formic acid/acetonitrile) to give the title compound (40 mg) as a white solid.

MS (ESI, m/z): 468.2 [(M+H)$^+$].

Example 50

Preparation of (1a-39)

(4S)-4-Benzhydryl-6-ethylsulfonyl-9-hydroxy-2-isopropyl-3,4-dihydropyrazino[1,2-c]pyrimidine-1,8-dione

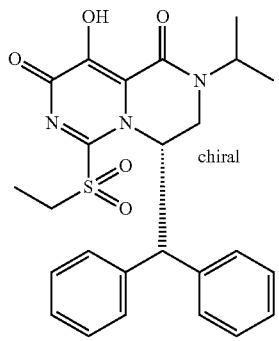 [SMILES: CCS(=O)(=O)c1nc(=O)c(O)c2n1[C@@H](C(c1ccccc1)c1ccccc1)CN(C(C)C)C2=O]

(4S)-4-Benzhydryl-6-ethylsulfinyl-9-hydroxy-2-isopropyl-3,4-dihydropyrazino[1,2-c]pyrimidine-1,8-dione (from example 43) was converted according to the procedure described for example 49 to give the title compound as a yellow liquid.

MS (ESI, m/z): 482.2 [(M+H)$^+$].

Example 51

Preparation of (1a-40)

(4S)-4-Benzhydryl-9-hydroxy-2-isopropyl-6-methyl-3,4-dihydropyrazino[1,2-c]pyrimidine-1,8-dione

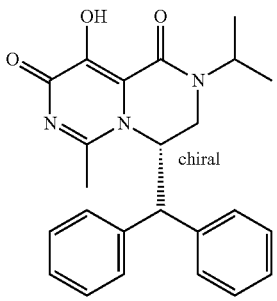 [SMILES: Cc1nc(=O)c(O)c2n1[C@@H](C(c1ccccc1)c1ccccc1)CN(C(C)C)C2=O]

To a solution of (4S)-4-benzhydryl-9-hydroxy-2-isopropyl-6-methylsulfonyl-3,4-dihydropyrazino[1,2-c]pyrimidine-1,8-dione (from example 49, 10 mg) in tetrahydrofuran (3 ml) was added at 0-5° C. a solution of MeMgBr in diethyl ether (3 M, 0.07 ml)) and stirring was continued at 0-5° C. for 1.5 h. The mixture was partitioned between saturated aqueous ammoniumchloride and ethyl acetate, the organic layer dried, evaporated and the residue purified by preparative HPLC (phenomenex synergie, C18, 150×30 mm, 4 μm particle size, water containing 0.2% formic acid/acetonitrile) to give the title compound (4 mg) as a yellow solid.

MS (ESI, m/z): 404.3 [(M+H)$^+$].

Example 52

Preparation of (1a-41)

(4S)-4-Benzhydryl-6-ethyl-9-hydroxy-2-isopropyl-3,4-dihydropyrazino[1,2-c]pyrimidine-1,8-dione

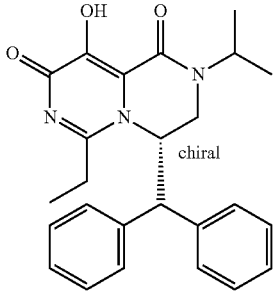 [SMILES: CCc1nc(=O)c(O)c2n1[C@@H](C(c1ccccc1)c1ccccc1)CN(C(C)C)C2=O]

(4S)-4-Benzhydryl-9-hydroxy-2-isopropyl-6-methylsulfonyl-3,4-dihydropyrazino[1,2-c]pyrimidine-1,8-dione (from example 49) was converted according to the procedure described for example 51 but using EtMgBr to give the title compound as a yellow solid.
MS (ESI, m/z): 418.2 [(M+H)+].

Example 53

Preparation of (1a-42)

(4S)-4-benzhydryl-9-hydroxy-2-isopropyl-6-phenyl-3,4-dihydropyrazino[1,2-c]pyrimidine-1,8-dione

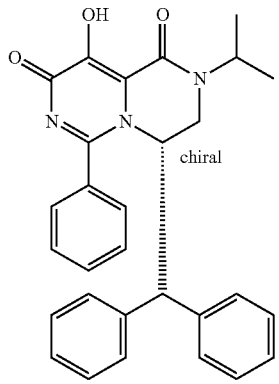 [SMILES: CC(C)N1C[C@H](C(c2ccccc2)c2ccccc2)n2c(-c3ccccc3)nc(=O)c(O)c2C1=O]

(4S)-4-Benzhydryl-9-hydroxy-2-isopropyl-6-methylsulfonyl-3,4-dihydropyrazino[1,2-c]pyrimidine-1,8-dione (from example 49) was converted according to the procedure described for example 51 but using PhMgBr to give the title compound as a pale white solid.
MS (ESI, m/z): 466.2 [(M+H)+].

Example 54

Preparation of (1a-43)

(4S)-4-Benzhydryl-9-hydroxy-6-imidazol-1-yl-2-isopropyl-3,4-dihydropyrazino[1,2-c]pyrimidine-1,8-dione

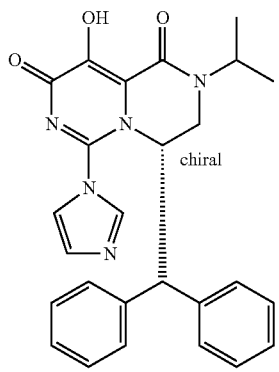 [SMILES: CC(C)N1C[C@H](C(c2ccccc2)c2ccccc2)n2c(-n3ccnc3)nc(=O)c(O)c2C1=O]

To a solution of (4S)-4-benzhydryl-9-hydroxy-2-isopropyl-6-methylsulfonyl-3,4-dihydropyrazino[1,2-c]pyrimidine-1,8-dione (from example 49, 30 mg) in acetonitrile (10 ml) was added at 22° C. potassium carbonate (88 mg)) and imidazole (22 mg) and stirring was continued at 70° C. for 2 h. The mixture was evaporated and the residue purified by preparative HPLC (phenomenex synergie, C18, 150×30 mm, 4 μm particle size, water containing 0.2% formic acid/acetonitrile) to give the title compound (6 mg) as a yellow solid.
MS (ESI, m/z): 456.3 [(M+H)+].

Example 55

Preparation of (1a-44)

(4S)-4-Benzhydryl-9-hydroxy-2-isopropyl-6-(1,2,4-triazol-4-yl)-3,4-dihydropyrazino[1,2-c]pyrimidine-1,8-dione

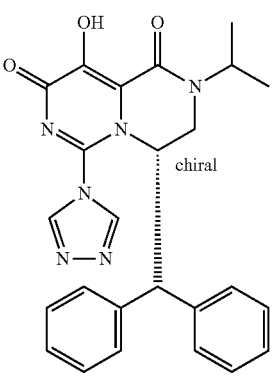 [SMILES: CC(C)N1C[C@H](C(c2ccccc2)c2ccccc2)n2c(-n3cnnc3)nc(=O)c(O)c2C1=O]

(4S)-4-Benzhydryl-9-hydroxy-2-isopropyl-6-methylsulfonyl-3,4-dihydropyrazino[1,2-c]pyrimidine-1,8-dione (from example 49) was converted according to the procedure described for example 54 but using 4H-1,2,4-triazole to give the title compound as a yellow solid.
MS (ESI, m/z): 457.3 [(M+H)+].

Example 56

Preparation of (1a-45)

(4S)-4-(6,11-Dihydro-5H-dibenzo[2,1-b:1',2'-e][7]annulen-11-yl)-9-hydroxy-6-imidazol-1-yl-2-isopropyl-3,4-dihydropyrazino[1,2-c]pyrimidine-1,8-dione

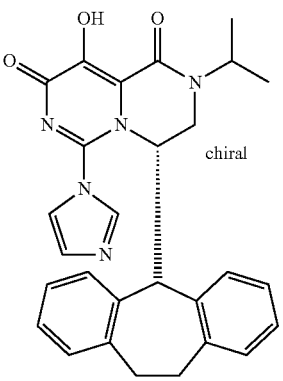 [SMILES: CC(C)N1C[C@H](C2c3ccccc3CCc3ccccc32)n2c(-n3ccnc3)nc(=O)c(O)c2C1=O]

(4S)-4-(6,11-Dihydro-5H-dibenzo[2,1-b:1',2'-e][7]annulen-11-yl)-9-hydroxy-2-isopropyl-6-methylsulfonyl-3,4-dihydropyrazino[1,2-c]pyrimidine-1,8-dione (prepared in analogy to example 49) was converted according to the procedure described for example 54 to give the title compound as a white solid.
MS (ESI, m/z): 482.2 [(M+H)+].

Example 57

Preparation of (1a-46)

((4S)-4-(6,11-Dihydro-5H-dibenzo[2,1-b:1',2'-e][7]annulen-11-yl)-9-hydroxy-2-isopropyl-6-(1,2,4-triazol-4-yl)-3,4-dihydropyrazino[1,2-c]pyrimidine-1,8-dione

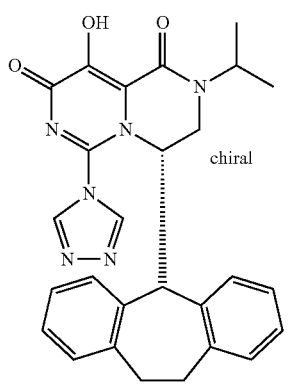 [SMILES: CC(C)N1C[C@H](C2c3ccccc3CCc3ccccc32)n2c(-n3cnnc3)nc(=O)c(O)c2C1=O]

(4S)-4-(6,11-Dihydro-5H-dibenzo[2,1-b:1',2'-e][7]annulen-11-yl)-9-hydroxy-2-isopropyl-6-methylsulfonyl-3,4-dihydropyrazino[1,2-c]pyrimidine-1,8-dione (prepared in analogy to example 49) was converted according to the procedure described for example 54 but using 4H-1,2,4-triazole to give the title compound as a white solid.
MS (ESI, m/z): 483.2 [(M+H)+].

Example 58

Preparation of (1a-47)

4-(6,11-Dihydro-5H-dibenzo[2,1-b:1',2'-e][7]annulen-11-yl)-9-hydroxy-2-isopropyl-6-vinyl-3,4-dihydropyrazino[1,2-c]pyrimidine-1,8-dione

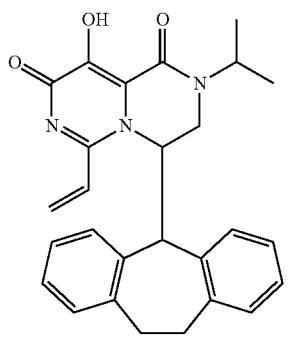 [SMILES: C=Cc1nc(=O)c(O)c2n1C(C1c3ccccc3CCc3ccccc31)CN(C(C)C)C2=O]

4-(6,11-Dihydro-5H-dibenzo[2,1-b:1',2'-e][7]annulen-1-yl)-9-hydroxy-2-isopropyl-6-methylsulfonyl-3,4-dihydropyrazino[1,2-c]pyrimidine-1,8-dione (prepared in analogy to example 49) was converted according to the procedure described for example 51 but using CH$_2$=CHMgBr to give the title compound as a yellow solid.
MS (ESI, m/z): 442.2 [(M+H)+].

Example 59

Preparation of (1a-48)

4-(6,11-Dihydro-5H-dibenzo[2,1-b:1',2'-e][7]annulen-11-yl)-9-hydroxy-6-(hydroxymethyl)-2-isopropyl-3,4-dihydropyrazino[1,2-c]pyrimidine-1,8-dione

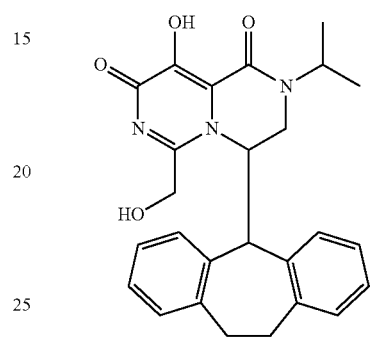

a) [4-(6,11-Dihydro-5H-dibenzo[2,1-b:1',2'-e][7]annulen-11-yl)-9-hydroxy-2-isopropyl-1,8-dioxo-3,4-dihydropyrazino[1,2-c]pyrimidin-6-yl]methyl 2,2-dimethylpropanoate

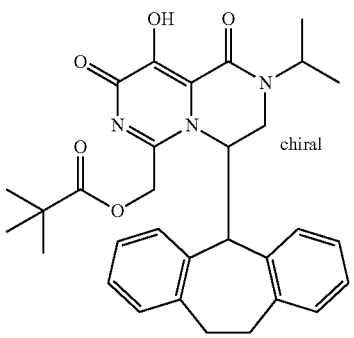 [SMILES: CC(C)N1CC(C2c3ccccc3CCc3ccccc32)n2c(COC(=O)C(C)(C)C)nc(=O)c(O)c2C1=O]

To a solution of iodomethyl pivalate (242 mg) in anhydrous tetrahydrofuran (5 ml) was added slowly at −65° C. a solution of i-PrMgCl in tetrahydrofuran (2 M, 0.6 ml) and stirring was continued at −65° C. for 1 h. A solution of 4-(6,11-dihydro-5H-dibenzo[2,1-b:1',2'-e][7]annulen-11-yl)-9-hydroxy-2-isopropyl-6-methylsulfonyl-3,4-dihydropyrazino[1,2-c]pyrimidine-1,8-dione (prepared in analogy to example 49, 49 mg) in tetrahydrofuran (2.5 ml) was added slowly to the Grignard solution while maintaining the internal temperature at −65° C. The mixture was warmed to 20° C. and stirring was continued for 1.5 h. The mixture was partitioned between saturated aqueous ammoniumchloride and ethyl acetate, the organic layer dried, evaporated and the residue purified by preparative HPLC (phenomenex synergie, C18, 150×30 mm, 4 am particle size, water containing 0.2% formic acid/acetonitrile) to give the title compound (20 mg) as a yellow solid.
MS (ESI, m/z): 530.3 [(M+H)+].

b) To a solution of [4-(6,11-dihydro-5H-dibenzo[2,1-b:1', 2'-e][7]annulen-11-yl)-9-hydroxy-2-isopropyl-1,8-dioxo-3, 4-dihydropyrazino[1,2-c]pyrimidin-6-yl]methyl 2,2-dimethylpropanoate (45 mg) in methanol (10 ml) was added potassium carbonate (35 mg) and stirring was continued at 22° C. for 2 h. The mixture was partitioned between aqueous hydrochloric acid (1 M) and ethyl acetate, the organic layer dried, evaporated and the residue purified by preparative HPLC (phenomenex synergie, C18, 150×30 mm, 4 μm particle size, water containing 0.2% formic acid/acetonitrile) to give example 59 (11 mg) as a light yellow solid.

MS (ESI, m/z): 446.2 [(M+H)$^+$].

Example 60

Preparation of (1a-49)

(4S)-4-Benzhydryl-9-hydroxy-2-isopropyl-6-(methylamino)-3,4-dihydropyrazino[1,2-c]pyrimidine-1,8-dione

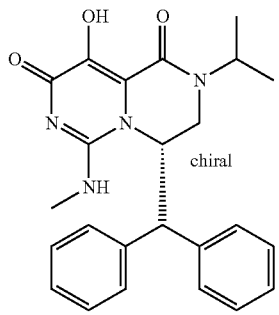 [SMILES: CNc1nc(=O)c(O)c2n1[C@@H](C(c1ccccc1)c1ccccc1)CN(C(C)C)C2=O]

To a solution of ((4S)-4-benzhydryl-9-hydroxy-2-isopropyl-6-methylsulfinyl-3,4-dihydropyrazino[1,2-c]pyrimidine-1,8-dione (from example 49, 47 mg) in dimethylformamide (5 ml) was added subsequently diisopropylethylamine (129 mg) and methylamine hydrochloride (34 mg) and stirring was continued in a microwave oven at 110° C. for 2 h. The mixture was evaporated and the residue purified by preparative HPLC (phenomenex synergie, C18, 150×30 mm, 4 μm particle size, water containing 0.2% formic acid/acetonitrile) to give the title compound (20 mg) as a yellow solid.

MS (ESI, m/z): 419.3 [(M+H)$^+$].

Example 61

Preparation of (1a-50)

1-[(4S)-4-Benzhydryl-9-hydroxy-2-isopropyl-1,8-dioxo-3,4-dihydropyrazino[1,2-c]pyrimidin-6-yl]-3-methyl-guanidine

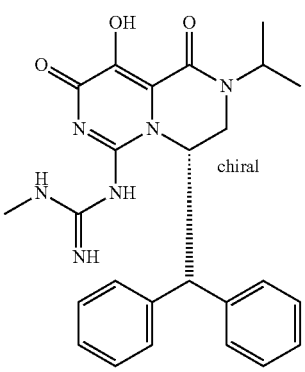 [SMILES: CNC(=N)Nc1nc(=O)c(O)c2n1[C@@H](C(c1ccccc1)c1ccccc1)CN(C(C)C)C2=O]

To a solution of (4S)-4-benzhydryl-9-hydroxy-2-isopropyl-6-methylsulfonyl-3,4-dihydropyrazino[1,2-c]pyrimidine-1,8-dione (25 mg, from example 49) and 1-methyl-guanidine hydrochloride 61 (54.5 mg) in dimethylformamide (2 ml) was added potassium carbonate (35 mg) and stirring was continued at 60° C. for 15 h. The mixture was partitioned between water and ethyl acetate, the organic layer was dried, evaporated and the residue purified by preparative HPLC (phenomenex synergie, C18, 150×30 mm, 4 μm particle size, water containing 0.2% formic acid/acetonitrile) to give the title compound (7 mg) as a white solid.

MS (ESI, m/z): 461.3 [(M+H)$^+$].

Compounds of Formula (Ia) Having the Following Substitution Patterns were Prepared According to Scheme 6:

Scheme 6

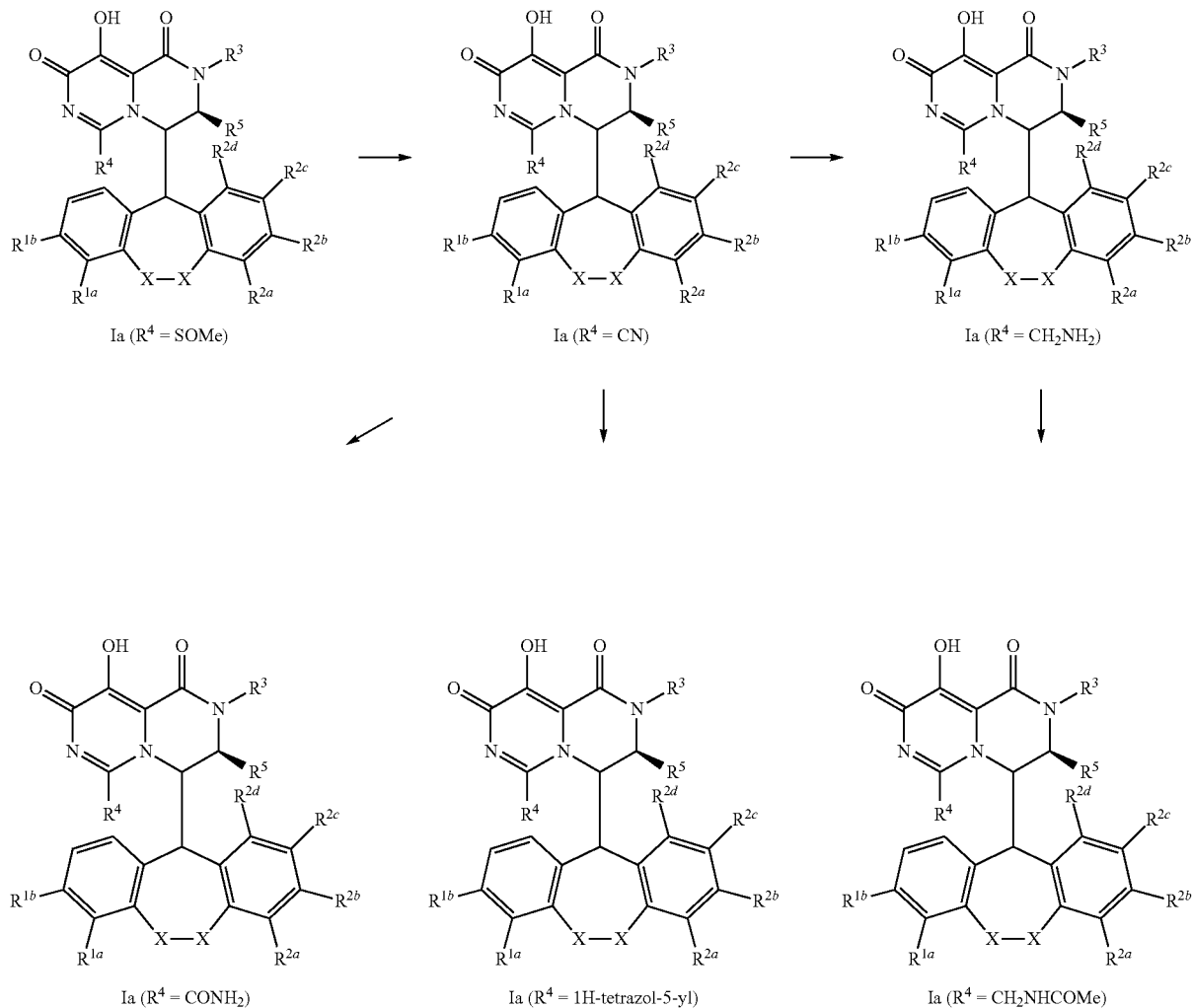

Ia (R⁴ = SOMe)    Ia (R⁴ = CN)    Ia (R⁴ = CH₂NH₂)

Ia (R⁴ = CONH₂)    Ia (R⁴ = 1H-tetrazol-5-yl)    Ia (R⁴ = CH₂NHCOMe)

|        | $R^{1a}$ | $R^{1b}$ | $R^{2a}$ | $R^{2b}$ | $R^{2c}$ | $R^{2d}$ | X-X | $R^3$ | $R^4$ | $R^5$ |
|--------|---|---|---|---|---|---|-----|-------|------------------|---|
| Ia-51  | H | H | H | H | H | H | —   | i-Pr  | CN               | H |
| Ia-52  | H | H | H | H | H | H | —   | i-Pr  | CONH₂            | H |
| Ia-53  | H | H | H | H | H | H | —   | i-Pr  | 1H-Tetrazol-5-yl | H |
| Ia-54  | H | H | H | H | H | H | —   | i-Pr  | CH₂NH₂           | H |
| Ia-55  | H | H | H | H | H | H | —   | i-Pr  | CH₂NHCOMe        | H |

Compounds of formula Ia (R⁴=CN) can be prepared by the reaction of compounds of formula Ia (R⁴=SOMe) with tetrabutylammonium cyanide in a solvent such as dichloromethane at room temperature.

Compounds of formula Ia (R⁴=CONH₂) can be prepared by the reaction of compounds of formula Ia (R⁴=CN) with a base such as e.g. sodium hydroxide in a solvent such as water or preferably a mixture of water and methanol at room temperature.

Compounds of formula Ia (R⁴=1 H-tetrazol-5-yl) can be prepared by the reaction of compounds of formula Ia (R⁴=CN) with trimethylsilyl azide and tetrabutylammonium fluoride in a solvent such as tetrahydrofuran at elevated temperature e.g. at 110° C. in a microwave oven.

Compounds of formula Ia (R⁴=CH₂NH₂) can be prepared by the hydrogenation of compounds of formula Ia (R⁴=CONH₂) at elevated pressure, e.g. at 50 Psi and a catalyst, e.g. platinoxide, in a solvent such as tetrahydrofuran at elevated temperature, e.g. at 50° C.

Compounds of formula Ia (R⁴=CH₂NHCOMe) can be prepared by the hydrogenation of compounds of formula Ia (R⁴=CN) at elevated pressure, e.g. at 50 Psi and a catalyst, e.g. platinoxide in the presence of e.g. acetic anhydride in a solvent such as tetrahydrofuran at elevated temperature, e.g. at 50° C.

Example 62

Preparation of (1a-51)

(4S)-4-Benzhydryl-9-hydroxy-2-isopropyl-1,8-dioxo-3,4-dihydropyrazino[1,2-c]pyrimidine-6-carbonitrile

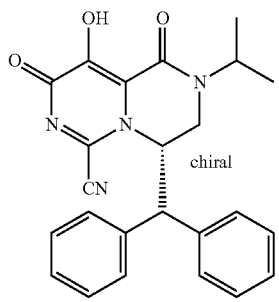 [SMILES: CC(C)N1C[C@H](C(c2ccccc2)c2ccccc2)n2c(C#N)nc(=O)c(O)c2C1=O]

To a solution of (4S)-4-benzhydryl-9-hydroxy-2-isopropyl-6-methylsulfinyl-3,4-dihydropyrazino[1,2-c]pyrimidine-1,8-dione (from example 34, 80 mg) in dichloromethane (3 ml) was added at 25° C. (n-Bu)$_4$NCN (242 mg) and stirring was continued at for 16 h. The solution was evaporated and the residue purified by preparative HPLC (phenomenex synergie, C18, 150×30 mm, 4 μm particle size, water containing 0.2% formic acid/acetonitrile) to give the title compound (40 mg) as a yellow solid.

MS (ESI, m/z): 415.1 [(M+H)$^+$].

Example 63

Preparation of (1a-52)

(4S)-4-Benzhydryl-9-hydroxy-2-isopropyl-1,8-dioxo-3,4-dihydropyrazino[1,2-c]pyrimidine-6-carboxamide

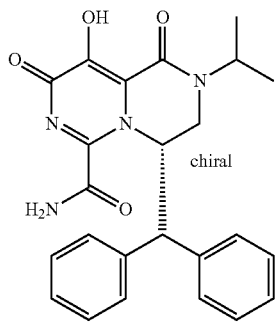 [SMILES: CC(C)N1C[C@H](C(c2ccccc2)c2ccccc2)n2c(C(N)=O)nc(=O)c(O)c2C1=O]

To a solution of (4S)-4-benzhydryl-9-hydroxy-2-isopropyl-1,8-dioxo-3,4-dihydropyrazino[1,2-c]pyrimidine-6-carbonitrile (30 mg, from example 62) in methanol (2 ml) was added at 25° C. an aqueous solution of NaOH (20%, 2 ml) and stirring was continued for 2 h. The mixture was partitioned between aqueous hydrochloric acid (1 M) and ethyl acetate, the organic layer was dried, evaporated and the residue purified by preparative HPLC (phenomenex synergie, C18, 150×30 mm, 4 μm particle size, water containing 0.2% formic acid/acetonitrile) to give the title compound (16 mg) as a white solid.

MS (ESI, m/z): 433.2 [(M+H)$^+$].

Example 64

Preparation of (1a-53)

(4S)-4-Benzhydryl-9-hydroxy-2-isopropyl-6-(1H-tetrazol-5-yl)-3,4-dihydropyrazino[1,2-c]pyrimidine-1,8-dione

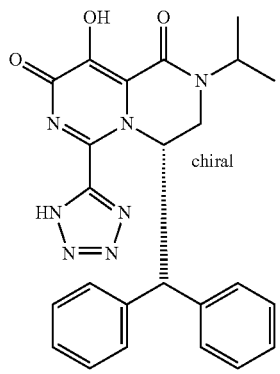 [SMILES: CC(C)N1C[C@H](C(c2ccccc2)c2ccccc2)n2c(-c3nnn[nH]3)nc(=O)c(O)c2C1=O]

A mixture of (4S)-4-benzhydryl-9-hydroxy-2-isopropyl-1,8-dioxo-3,4-dihydropyrazino[1,2-c]pyrimidine-6-carbonitrile (from example 62, 25 mg), Bu$_4$NF (47 mg) and TMSN$_3$ (21 mg) in tetrahydrofuran (2 ml) in a sealed tube was heated in a microwave oven to 110° C. for 20 min. The mixture was evaporated and the residue purified by preparative HPLC (phenomenex synergie, C18, 150×30 mm, 4 μm particle size, water containing 0.2% formic acid/acetonitrile) to give the title compound (8 mg) as a white solid.

MS (ESI, m/z): 458.2 [(M+H)$^+$].

Example 65

Preparation of (1a-54)

(4S)-6-(Aminomethyl)-4-benzhydryl-9-hydroxy-2-isopropyl-3,4-dihydropyrazino[1,2-c]pyrimidine-1,8-dione

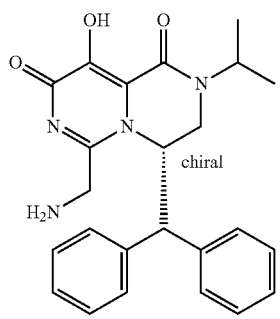 [SMILES: CC(C)N1C[C@H](C(c2ccccc2)c2ccccc2)n2c(CN)nc(=O)c(O)c2C1=O]

A suspension of (4S)-4-benzhydryl-9-hydroxy-2-isopropyl-1,8-dioxo-3,4-dihydropyrazino[1,2-c]pyrimidine-6-carboxamide (30 mg, from example 63) and PtO$_2$ (30 mg) in tetrahydrofuran (10 ml) was hydrogenated at 50° C. and 50 Psi for 20 h. The mixture was filtered, the filtrate evaporated and the residue purified by preparative HPLC (phenomenex

Example 66

Preparation of (1a-55)

N-[[(4S)-4-Benzhydryl-9-hydroxy-2-isopropyl-1,8-dioxo-3,4-dihydropyrazino[1,2-c]pyrimidin-6-yl]methyl]acetamide

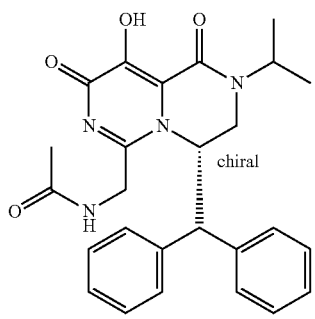 [SMILES: CC(=O)NCc1nc(=O)c(O)c2n1[C@@H](C(c1ccccc1)c1ccccc1)CN(C(C)C)C2=O]

To a solution of (4S)-4-benzhydryl-9-hydroxy-2-isopropyl-1,8-dioxo-3,4-dihydropyrazino[1,2-c]pyrimidine-6-carbonitrile (30 mg, from example 62) in tetrahydrofuran (10 ml) was added at 10° C. acetic anhydride (71 mg) and $PtO_2$ (30 mg) and the mixture was hydrogenated at 50° C. and 50 Psi for 20 h. The mixture was filtered, the filtrate evaporated and the residue purified by preparative HPLC (phenomenex synergie, C18, 150×30 mm, 4 am particle size, water containing 0.2% formic acid/acetonitrile) to give the title compound (8 mg) as a yellow solid.

MS (ESI, m/z): 461.2 [(M+H)$^+$].

Compounds of Formula (Ia) Having the Following Substitution Patterns were Prepared According to Scheme 1:

| | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| 1a-56 | H | H | H | H | H | H | — | i-Pr | NHCOOMe | H |
| 1a-57 | Cl | H | H | H | H | H | $CH_2$—S | CH(Me)CF$_3$ | OMe | H |
| 1a-58 | Cl | H | H | H | H | H | $CH_2$—S | i-Pr | OMe | H |
| 1a-59 | Cl | H | H | H | H | H | $CH_2$—S | Me | OMe | H |
| 1a-60 | H | H | H | H | F | H | $CH_2$—S | i-Pr | OMe | H |
| 1a-61 | H | H | H | H | F | H | $CH_2$—O | i-Pr | OMe | H |

Compounds of formula Ia (R$^4$=NHCOOMe) are prepared by the reaction of substituted amidines 17 (R$^4$=NH$_2$) with an alkyl chloroformate, e.g. methyl chloroformate and a base, preferably triethylamine in a solvent such as dichloromethane at 0 to 20° C., preferably 0° C. to give the intermediate acylguanidine derivative 17 (R$^4$=NHCOOMe), which was reacted with an alkyl oxalate, preferably diethyl oxalate, and a base, preferably lithium hexamethyldisilazide, in an ether as the solvent, preferably tetrahydrofuran, at −78 to −20° C., preferably at −60 to −20° C. to afford the compound of formula Ia (R$^4$=NHCOOMe).

Compounds of formula Ia (R$^3$=Me) are prepared by the reaction of alcohols 5 with mesyl chloride and a base, e.g. triethylamine in a solvent such as dichloromethane at 0-20° C. to give the intermediate mesylate, which can be substituted with an alkylamine, e.g. methylamine in a solvent such as dimethylformamide and an alcohol, preferably ethanol at elevated temperature, e.g. 50-70° C., to give compounds of formula Ia (R$^3$=Me).

Example 67

Preparation of (1a-56)

Methyl N-[(4S)-4-benzhydryl-9-hydroxy-2-isopropyl-1,8-dioxo-3,4-dihydropyrazino[1,2-c]pyrimidin-6-yl]carbamate

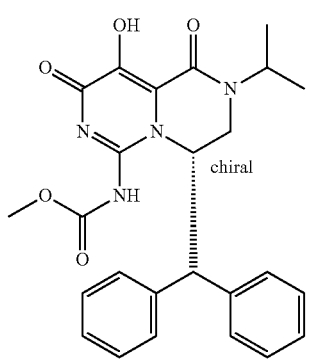 [SMILES: COC(=O)Nc1nc(=O)c(O)c2n1[C@@H](C(c1ccccc1)c1ccccc1)CN(C(C)C)C2=O]

To a solution of (2S)-2-benzhydryl-4-isopropyl-5-oxo-piperazine-1-carboxamidine (50 mg, from example 3a) and triethylamine (35 mg) in dichloromethane (2 ml) was added at 0° C. methyl chloroformate (27 mg) and stirring was continued at 0° C. for 2 h. The mixture was evaporated and the crude intermediate methyl N-[(2S)-2-benzhydryl-4-isopropyl-5-oxo-piperazine-1-carboximidoyl]carbamate (MS (ESI, m/z): 409.2 [(M+H)$^+$]) dissolved in tetrahydrofuran (2 ml). A solution of dimethyl oxalate (56 mg) in tetrahydrofuran (2 ml) was added at −60° C., which was followed by the addition of lithium hexamethyldisilazide (1 M, 1.4 ml) and stirring was continued at −60° C. for 2 h. The mixture was partitioned between aqueous hydrochloric acid (1 M) and ethyl acetate, the organic layer was dried, evaporated and the residue purified by preparative HPLC (phenomenex synergie, C18, 150×30 mm, 4 µm particle size, water containing 0.2% formic acid/acetonitrile) to give the title compound (7 mg) as a white solid.

MS (ESI, m/z): 463.2 [(M+H)$^+$].

Example 68 to 71

Preparation of (1a-57) and separation of its isomers:

4-(7-Chloro-6,11-dihydrobenzo[c][1]benzothiepin-11-yl)-9-hydroxy-6-methoxy-2-[(1R)-2,2,2-trifluoro-1-methyl-ethyl]-3,4-dihydropyrazino[1,2-c]pyrimidine-1,8-dione

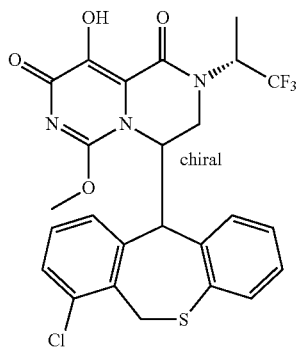 [SMILES: COc1nc(=O)c(O)c2n1C(C1c3ccccc3SCc3c(Cl)cccc31)CN([C@H](C)C(F)(F)F)C2=O]

a) Ethyl 3-chloro-2-(phenylsulfanylmethyl)benzoate

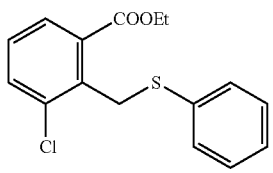 [SMILES: CCOC(=O)c1cccc(Cl)c1CSc1ccccc1]

To a solution of ethyl 2-(bromomethyl)-3-chlorobenzoate (1.92 g, preparation: Houbion, J. A., patent U.S. Pat. No. 4,397,790, (1983)) in acetone (15 ml) was added at 22° C. potassium carbonate (1.91 g) and benzenethiol (0.71 ml) and stirring was continued at 60° C. for 17 h. The mixture was partitioned between water and ethyl acetate, the organic layer was dried and evaporated to give the crude title compound (2.03 g) as a brown oil, which was used in the next step without purification.
MS (ESI, m/z): 307.2 [(M+H)+].

b) 3-Chloro-2-(phenylsulfanylmethyl)benzoic acid

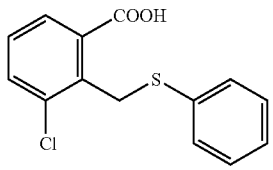 [SMILES: O=C(O)c1cccc(Cl)c1CSc1ccccc1]

To a solution of ethyl 3-chloro-2-(phenylsulfanylmethyl)benzoate (1.35 g) in ethanol (15 ml) was added at 0° C. an aqueous solution of sodium hydroxide (2 N, 8.8 ml) and stirring was continued at 25° C. for 20 h. The mixture was evaporated, the residue diluted with water (10 ml) and the pH was adjusted to 2-3 using aqueous hydrochloric acid (2 N). The suspension obtained was filtered, the residue washed with water and petrol ether and dried to give the title compound (0.94 g) as a yellow solid.

c) 7-Chloro-6H-benzo[c][1]benzothiepin-11-one

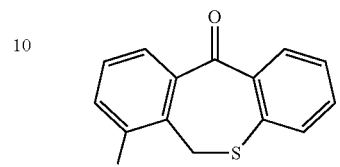

To polyphosphoric acid (2.40 g) was added at 90° C. 7-chloro-6H-benzo[c][1]benzothiepin-11-one (0.30 g) and stirring was continued at 120° C. for 2.5 h. in small portions and the color of reaction mixture turned to brownish red. The mixture was partitioned between water and ethyl acetate, the organic layer was dried, evaporated and the residue triturated with petrol ether to give the title compound (0.25 g) as a pale yellow solid.

d) 7-Chloro-6,11-dihydrobenzo[c][1]benzothiepin-11-ol

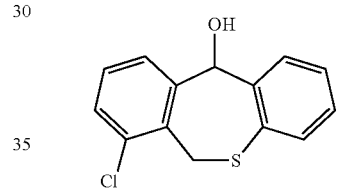

To a solution of 7-chloro-6H-benzo[c][1]benzothiepin-11-one 7 (0.72 g) in methanol (2.5 ml) and dichloromethane (2.5 ml) was added at 0° C. NaBH$_4$ (0.10 g) and stirring was continued at 0° C. for 25 min. The mixture was partitioned between aqueous saturated ammonium chloride and ethyl acetate, the organic layer was dried, evaporated and the residue triturated with petrol ether to give the title compound (0.69 g) as a solid.
$^1$H-NMR (400 MHz, CDCl$_3$) δ=7.52 (br. s, 1 H), 7.38 (t, J=7.4 Hz, 2 H), 7.25-7.08 (m, 4 H), 6.19 (s, 1 H), 4.84 (d, J=14.3 Hz, 1 H), 4.44 (d, J=14.3 Hz, 1 H), 2.69 (br. s, 1 H) ppm.

e) Ethyl 2-(benzhydrylideneamino)-2-(7-chloro-6,11-dihydrobenzo[c][1]benzothiepin-11-yl)acetate

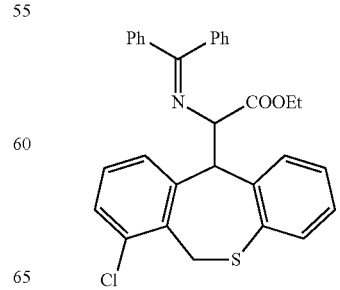

To a solution of 7-chloro-6,11-dihydrobenzo[c][1]benzothiepin-11-ol (0.45 g) in dichloromethane (7 ml) was added slowly at 0-5° C. SOCl$_2$ (0.63 ml), the mixture was slowly warmed to 25° C. and stirring was continued for 19 h. The mixture was evaporated and the residue containing crude 7,11-dichloro-6,11-dihydrobenzo[c][1]benzothiepine dissolved in dichloromethane (9 ml). Ethyl 2-((diphenylmethylene)amino)acetate (0.40 g) was added at 0-5° C., which was followed by the subsequent addition of (n-Bu)$_4$NBr (0.65 g) and an aqueous solution of sodium hydroxide (50%, 1.5 ml) and stirring was continued at 0-5° C. for 30 min and at 25° C. for 1.5 h. The mixture was partitioned between water and dichloromethane, the organic layer was dried and evaporated to give the crude title compound (0.86 g) as a brown solid, which was used in the next step without purification.

MS (ESI, m/z): 512.1 [(M+H)$^+$].

f) Ethyl 2-(benzhydrylideneamino)-2-(7-chloro-6,11-dihydrobenzo[c][1]benzothiepin-11-yl)acetate was converted to examples 68-71 in analogy to the preparation of examples 14 to 17 but using (2R)-1,1,1-trifluoropropan-2-amine in the reductive amination step.

The mixture of four isomers was separated by preparative HPLC (synergie, Max-RP C12, 100×30 mm, 5 μm particle size, water containing 0.05% hydrochloric acid/acetonitrile) to give a faster (250 mg) and slower eluting (300 mg) fraction.

The faster eluting HPLC-fraction was resolved by supercritical fluid chromatography (OD, 250×30 mm, 10 μm particle size, ethanol 45%, 155 MPa CO$_2$, 1% ammonia in water) to give example 68 as the faster eluting fraction (62 mg). MS (ESI, m/z): 552.2 [(M+H)$^+$]. The slower eluting fraction contained example 69 (57 mg). MS (ESI, m/z): 552.2 [(M+H)$^+$].

The slower eluting HPLC-fraction was resolved by supercritical fluid chromatography (OD, 250×30 mm, 10 μm particle size, ethanol 45%, 155 MPa CO$_2$, 1% ammonia in water) to give example 70 as the faster eluting fraction (66 mg). MS (ESI, m/z): 552.2 [(M+H)$^+$]. The slower eluting fraction contained example 71 (22 mg). MS (ESI, m/z): 552.2 [(M+H)+].

Example 72 to 75

Preparation of (1a-58) and separation of its isomers:

4-(7-Chloro-6,11-dihydrobenzo[c][1]benzothiepin-11-yl)-9-hydroxy-2-isopropyl-6-methoxy-3,4-dihydropyrazino[1,2-c]pyrimidine-1,8-dione

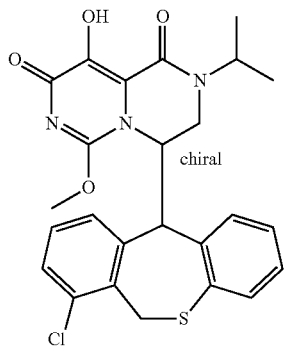 [SMILES: COc1nc(=O)c(O)c2n1C(C1c3ccccc3SCc3c(Cl)cccc31)CN(C(C)C)C2=O]

Examples 72-75 were prepared in analogy to examples 68-71 but using isopropylamine in the reductive amination step.

The mixture of four isomers (1.5 g crude) was separated by preparative HPLC (Phenomenex synergie, Max-RP, 250×80 mm, 10 μm particle size, water containing 0.2% formic acid/acetonitrile) to give a faster (280 mg) and slower eluting (220 mg) fraction.

The faster eluting HPLC-fraction was resolved by supercritical fluid chromatography (OD, 250×30 mm, 10 μm particle size, methanol 30%, 155 MPa CO$_2$, 1% ammonia in water) to give example 72 as the faster eluting fraction (46 mg). MS (ESI, m/z): 498.1 [(M+H)$^+$]. The slower eluting fraction contained example 73 (14 mg). MS (ESI, m/z): 498.1 [(M+H)$^+$].

The slower eluting HPLC-fraction was resolved by supercritical fluid chromatography (OD, 250×30 mm, 10 μm particle size, methanol 30%, 155 MPa CO$_2$, 1% ammonia in water) to give example 74 as the faster eluting fraction (40 mg). MS (ESI, m/z): 498.1 [(M+H)$^+$]. The slower eluting fraction contained example 75 (38 mg). MS (ESI, m/z): 498.1 [(M+H)$^+$].

Example 76 to 79

Preparation of (1a-59) and separation of its isomers:

4-(7-Chloro-6,11-dihydrobenzo[c][1]benzothiepin-11-yl)-9-hydroxy-6-methoxy-2-methyl-3,4-dihydropyrazino[1,2-c]pyrimidine-1,8-dione

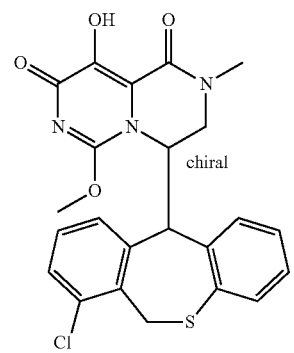 [SMILES: COc1nc(=O)c(O)c2n1C(C1c3ccccc3SCc3c(Cl)cccc31)CN(C)C2=O]

a) [2-(tert-butoxycarbonylamino)-2-(7-chloro-6,11-dihydrobenzo[c][1]benzothiepin-11-yl)ethyl]methanesulfonate

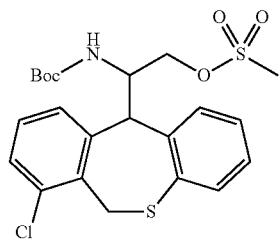 [SMILES: CC(C)(C)OC(=O)NC(COS(C)(=O)=O)C1c2ccccc2SCc2c(Cl)cccc21]

To a solution of tert-butyl N-[1-(7-chloro-6,11-dihydrobenzo[c][1]benzothiepin-11-yl)-2-hydroxy-ethyl]carbamate (10.0 g, prepared in analogy to example 5d) in dichloromethane (150 ml) was added subsequently at 5° C. triethylamine (6.8 ml) and mesylchloride (2.3 ml) and stirring was continued at 5° C. for 1 h. The mixture was washed with water, the organic layer was dried and evaporated to give the crude title compound (10.0 g) as a yellow solid, which was used in the next step without purification.

MS (ESI, m/z): 506.2 [(M+H)$^+$].

b) tert-Butyl N-[1-(7-chloro-6,11-dihydrobenzo[c][1]benzothiepin-11-yl)-2-(methylamino)ethyl]carbamate

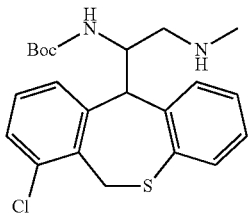 [SMILES: CNCC(NC(=O)OC(C)(C)C)C1c2ccccc2SCc2c(Cl)cccc21]

To a solution of [2-(tert-butoxycarbonylamino)-2-(7-chloro-6,11-dihydrobenzo[c][1]benzothiepin-11-yl)ethyl] methanesulfonate (10.0 g) dimethylformamide (100 ml) was added at 25° C. a solution of methylamine in ethanol (32% wt., 100 ml) and stirring was continued at 65° C. for 16 h. The mixture was evaporated, the residue partitioned between water and ethyl acetate, the organic layer was dried, evaporated and the residue purified by flash chromatography (silica gel, dichloromethane/methanol, 10:1) to give the title compound (5.5 g) as a light yellow solid.

MS (ESI, m/z):419.2 [(M+H)$^+$].

c) tert-Butyl N-[1-(7-chloro-6,11-dihydrobenzo[c][1]benzothiepin-1-yl)-2-(methylamino)ethyl]carbamate was converted in analogy to example 68-71 to give a crude mixture of four isomers, which was separated by preparative HPLC (Daiso, 250×50 mm, 10 μm particle size, water containing 0.2% formic acid/acetonitrile) to give a faster (335 mg) and slower eluting (140 mg) fraction.

The faster eluting HPLC-fraction was resolved by supercritical fluid chromatography (OJ, 250×50 mm, 10 μm particle size, ethanol 30%, 155 MPa CO$_2$, 1% ammonia in water) to give example 76 as the faster eluting fraction (80 mg). MS (ESI, m/z): 470.0 [(M+H)$^+$]. The slower eluting fraction contained example 77 (88 mg). MS (ESI, m/z): 470.0 [(M+H)$^+$].

The slower eluting HPLC-fraction was resolved by supercritical fluid chromatography (Oj, 250×50 mm, 10 μm particle size, ethanol 30%, 155 MPa CO$_2$, 1% ammonia in water) to give example 78 as the faster eluting fraction (15 mg). MS (ESI, m/z): 470.0 [(M+H)$^+$]. The slower eluting fraction contained example 79 (27 mg). MS (ESI, m/z): 470.0 [(M+H)$^+$].

Example 80 to 83

Preparation of (1a-60) and separation of its isomers:

4-(2-Fluoro-6,11-dihydrobenzo[c][1]benzothiepin-11-yl)-9-hydroxy-2-isopropyl-6-methoxy-3,4-dihydropyrazino[1,2-c]pyrimidine-1,8-dione

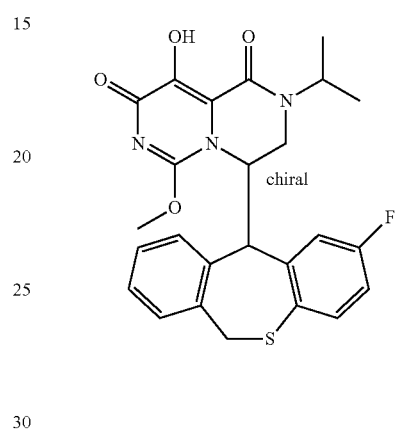

Examples 80-83 were prepared in analogy to examples 72-75 starting with 11-chloro-2-fluoro-6,11-dihydrobenzo[c][1]benzothiepine (preparation: Hulinska, H. et al., Collection of Czechoslovak Chemical Communications (1989), 54(5), 1388-402).

a) 5-(2-Fluoro-6,11-dihydrobenzo[c][1]benzothiepin-11-yl)-1-isopropyl-piperazin-2-one

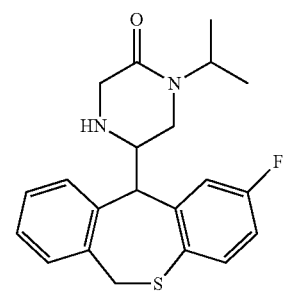 [SMILES: CC(C)N1CC(C2c3ccccc3CSc3ccc(F)cc32)NCC1=O]

The intermediate title compound as a mixture of four isomers was separated by chiral HPLC (Reprosil Chiral NR, n-heptane/ethanol, 85:15 containing 0.01 M NH$_4$OAc) to give a first eluting fraction A (71 mg), a second eluting fraction B (82 mg), a third eluting fraction C (75 mg) and a fourth eluting fraction D (108 mg).

MS (ESI, m/z) of all 4 fractions: 371.2 [(M+H)$^+$].

b) Fraction A-D were converted to example 80-83, respectively.

MS of examples 80-83 (ESI, m/z): 482.2 [(M+H)$^+$].

Example 84 to 87

Preparation of (1a-61) and separation of its isomers 4-(2-Fluoro-6,11-dihydrobenzo[c][1]benzoxepin-11-yl)-9-hydroxy-2-isopropyl-6-methoxy-3,4-dihydro-pyrazino[1,2-c]pyrimidine-1,8-dione

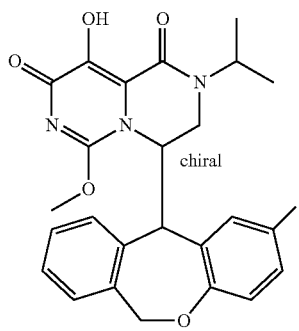

Examples 84-87 were prepared in analogy to examples 72-75 starting with 11-chloro-2-fluoro-6,11-dihydrobenzo[c][1]benzoxepine (preparation: Uno, H. et al., PCT patent application WO 87/07894).

a) 5-(2-Fluoro-6,11-dihydrobenzo[c][1]benzoxepin-11-yl)-1-isopropyl-piperazin-2-one

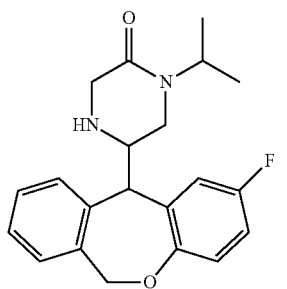

The intermediate title compound as a mixture of four isomers was separated by chiral HPLC (Reprosil Chiral NR, n-heptane/ethanol, 9:1 containing 0.01 M NH$_4$OAc) to give a first eluting fraction A (103 mg), a mixture of a second and third eluting fraction B/C and a fourth eluting fraction D (89 mg). The mixture B/C was again separated by chiral HPLC (Chiralpak AD, n-heptane/ethanol, 8:2 containing 0.01 M NH$_4$OAc) to give the pure second eluting fraction B (89 mg) and the pure third eluting fraction C (108 mg).

MS (ESI, m/z) of all 4 fractions: 355.2 [(M+H)$^+$].

b) Fraction A was converted to example 84, fraction B to example 87, fraction C to example 85 and fraction D to example 86.

MS of examples 84-87 (ESI, m/z): 466.3 [(M+H)$^+$].

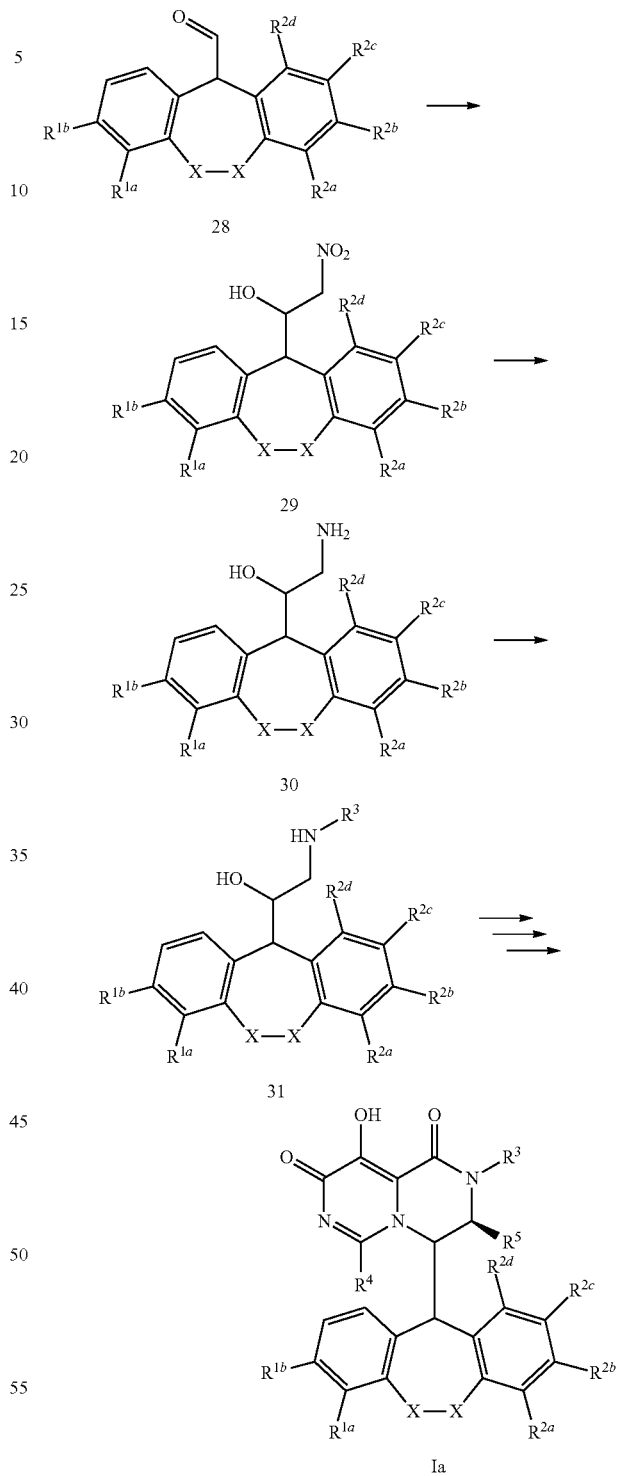

A Compound of Formula (Ia) Having the Following Substitution Pattern was Prepared According to Scheme 7:

| | R$^{1a}$ | R$^{1b}$ | R$^{2a}$ | R$^{2b}$ | R$^{2c}$ | R$^{2d}$ | X-X | R$^3$ | R$^4$ | R$^5$ |
|---|---|---|---|---|---|---|---|---|---|---|
| 1a-62 | H | H | H | H | H | Cl | — | iPr | OMe | H |

Compounds of formula Ia ($R^{2d}$=Cl) are prepared by the reaction of aldehydes 28 with nitromethane and a base, e.g. potassium carbonate at room temperature to give nitroalcohols 29.

The nitroalcohols 29 can be reduced with a borohydride, preferable sodium borohydride and nickel (II) chloride hexahydrate in an alcohol, preferably methanol at −5-0° C., to give the aminoalcohols 30.

Alkylation of the aminoalcohols 30 was accomplished with acetone and a borohydride, preferably sodium cyanoborohydride and zinc chloride in a solvent such as methanol at room temperature to furnish the alkylaminoalcohols 31.

Example 88 to 90

Preparation of (1a-62) and separation of its isomers:

4-[(2-Chlorophenyl)-phenyl-methyl]-9-hydroxy-2-isopropyl-6-methoxy-3,4-dihydropyrazino[1,2-c]pyrimidine-1,8-dione

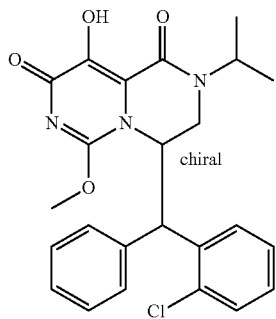 [SMILES: COc1nc(=O)c(O)c2n1C(C(c1ccccc1)c1ccccc1Cl)CN(C(C)C)C2=O]

a) 1-(2-Chlorophenyl)-3-nitro-1-phenyl-propan-2-ol

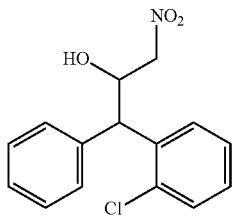

To a solution of 2-(2-chlorophenyl)-2-phenylacetaldehyde (1.00 g, preparation: Schunk, S. et al., PCT patent application WO 2010/108651) in nitromethane (5.4 ml) was added potassium carbonate (1.92 g) and stirring of the suspension was continued at 22° C. for 5 h. The mixture was partitioned between water and ethyl acetate, the organic layer was dried, evaporated and the residue purified by flash chromatography (silica gel, 0-30% ethyl acetate in n-heptane) to give the crude title compound (1.35 g) as a colorless oil, which was used in the next step without purification.

MS (ESI, m/z): 290.2 [(M+H)$^+$].

b) 3-Amino-1-(2-chlorophenyl)-1-phenyl-propan-2-ol

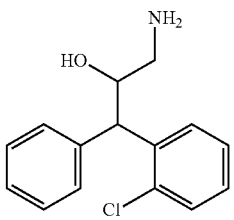 [SMILES: NCC(O)C(c1ccccc1)c1ccccc1Cl]

To a solution of 1-(2-chlorophenyl)-3-nitro-1-phenyl-propan-2-ol (414 mg) in methanol (3 ml) and nickel (II) chloride hexahydrate (337 mg) was added at −5° C. sodium borohydride (183 mg) over 10 min and stirring was continued at −5° C. for 1 h. The mixture was quenched by addition of a saturated solution of aqueous sodium hydrogencarbonate, the mixture was filtered through a glass fiber paper, the filtrate evaporated, the residue partitioned between water and ethyl acetate, the organic layer dried and evaporated to give the crude title compound (263 mg) as a light blue solid, which was used in the next step without purification.

MS (ESI, m/z): 262.2 [(M+H)$^+$].

c) 1-(2-Chlorophenyl)-3-(isopropylamino)-1-phenyl-propan-2-ol

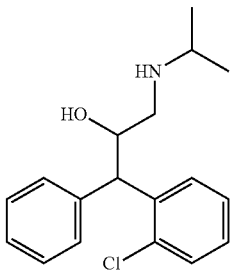 [SMILES: CC(C)NCC(O)C(c1ccccc1)c1ccccc1Cl]

To a suspension of 3-amino-1-(2-chlorophenyl)-1-phenyl-propan-2-ol (208 mg) and zinc chloride (33 mg) in methanol (1.3 ml) was added subsequently at 22° C. acetone (46 mg) and sodium cyanoborohydride (100 mg) and stirring was continued for 4.5 h. The mixture was partitioned between saturated aqueous sodium hydrogencarbonate and ethyl acetate, the organic layer was dried, evaporated and the residue purified by preparative HPLC (phenomenex synergie, C18, 150×30 mm, 4 μm particle size, water containing 0.2% formic acid/acetonitrile) to give the title compound (86 mg) as a colorless oil.

MS (ESI, m/z): 304.2 [(M+H)$^+$].

d) 5-[(2-Chlorophenyl)-phenyl-methyl]-1-isopropyl-piperazin-2-one

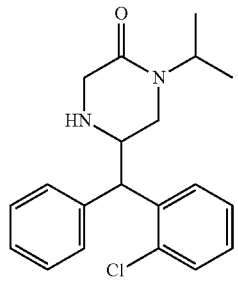 [SMILES: CC(C)N1CC(C(c2ccccc2)c2ccccc2Cl)NCC1=O]

1-(2-Chlorophenyl)-3-(isopropylamino)-1-phenyl-propan-2-ol was converted in analogy to examples 96-99 b-d to give the title compound as a mixture of four isomers (699 mg), which was separated by achiral HPLC (RP-18, acetonitrile/water containing 0.23% formic acid). The first eluting pair of diastereomers was separated by chiral HPLC (ChiralPack AD, n-heptane/ethanol, 4:1 containing 0.01 M NH$_4$OAc) to give a first eluting fraction A (59 mg) and a second eluting fraction B (57 mg). The second eluting pair of diastereomers was separated by chiral HPLC (ChiralPack AD, n-heptane/ethanol, 4:1 containing 0.01 M NH$_4$OAc) to give a first eluting fraction C (142 mg) and a second eluting fraction D (117 mg).

MS (ESI, m/z) of all 4 fractions: 343.3 [(M+H)$^+$].

e) Fraction A, B and D were converted in analogy to example 29f-h to example 88-90, respectively. Fraction C was lost during the conversion to the final product.

MS of examples 88-90 (ESI, m/z): 454.3 [(M+H)$^+$].

Compounds of Formula (Ia) Having the Following Substitution Patterns were Prepared According to Scheme 1:

Example 91

Preparation of (1a-63)

4-[Bis(4-chlorophenyl)methyl]-9-hydroxy-2-isopropyl-6-methoxy-3,4-dihydropyrazino[1,2-c]pyrimidine-1,8-dione

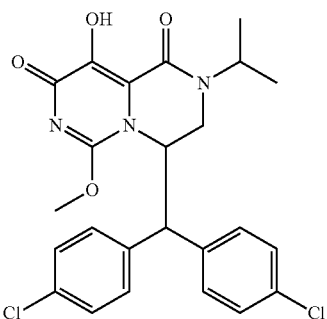 [SMILES: COc1nc(=O)c(O)c2n1C(C(c1ccc(Cl)cc1)c1ccc(Cl)cc1)CN(C(C)C)C2=O]

Example 91 was prepared in analogy to example 4 starting with 1-chloro-4-[chloro-(4-chlorophenyl)methyl]benzene (preparation: Song, K.-S. et al., Bioorganic & Medicinal Chemistry (2008), 16(7), 4035-4051).

MS (ESI, m/z):488.1 [(M+H)+].

| | R$^{1a}$ | R$^{1b}$ | R$^{2a}$ | R$^{2b}$ | R$^{2c}$ | R$^{2d}$ | X-X | R$^3$ | R$^4$ | R$^5$ |
|---|---|---|---|---|---|---|---|---|---|---|
| 1a-63 | H | Cl | H | Cl | H | H | — | i-Pr | OMe | H |
| 1a-64 | H | H | H | H | H | H | — | Et | OMe | H |
| 1a-65 | H | H | H | H | H | H | — | Me | OMe | H |
| 1a-66 | H | H | H | H | H | H | — | CH(Me)CF$_3$ | OMe | H |

Example 92

Preparation of (1a-64)

4-Benzhydryl-2-ethyl-9-hydroxy-6-methoxy-3,4-dihydropyrazino[1,2-c]pyrimidine-1,8-dione

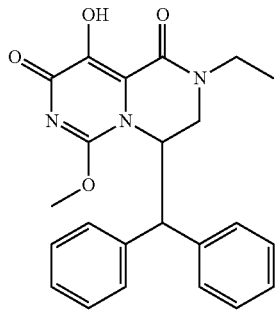 [SMILES: CCN1CC(C(c2ccccc2)c2ccccc2)n2c(OC)nc(=O)c(O)c2C1=O]

Example 92 was prepared in analogy to example 4.
MS (ESI, m/z): 406.3 [(M+H)$^+$].

Example 93

Preparation of (1a-65)

(4S)-4-Benzhydryl-9-hydroxy-6-methoxy-2-methyl-3,4-dihydropyrazino[1,2-c]pyrimidine-1,8-dione

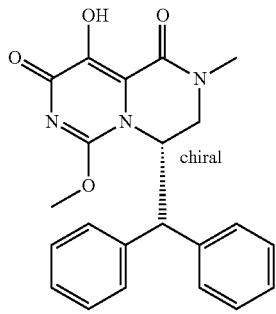 [SMILES: COc1nc(=O)c(O)c2n1[C@@H](C(c1ccccc1)c1ccccc1)CN(C)C2=O]

a) (S)-2-((tert-Butoxycarbonyl)amino)-3,3-diphenylpropyl methanesulfonate

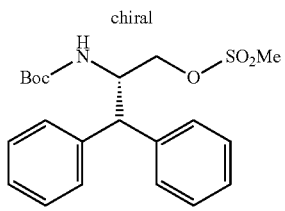 [SMILES: CC(C)(C)OC(=O)N[C@H](COS(C)(=O)=O)C(c1ccccc1)c1ccccc1]

To a solution of (S)-tert-butyl (3-hydroxy-1,1-diphenylpropan-2-yl)carbamate (1.64 g, preparation: Baker, R. et al., PCT patent application WO 93/21181) in dichloromethane (25 ml) was added subsequently at 0° C. triethylamine (1.01 g) and methanesulfonyl chloride (687 mg) and stirring was continued at 0° C. for 15 min. The mixture was partitioned between aqueous saturated NaHCO$_3$ and dichloromethane (3×100 ml), the organic layers were dried and evaporated to give the title compound (2.07 g) as a light yellow amorphous solid.
MS (ESI, m/z): 428.3 [(M+Na)+].

b) tert-Butyl N-[(1S)-1-(methylaminomethyl)-2,2-diphenyl-ethyl]carbamate

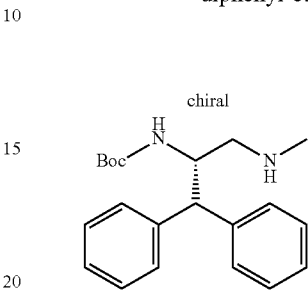

To solution of (S)-2-((tert-butoxycarbonyl)amino)-3,3-diphenylpropyl methanesulfonate (811 mg) in dimethylformamide (8 ml) was added at 22° C. methylamine (33% solution in ethanol, 8.2 ml) and stirring was continued in a sealed tube at 60° C. for 2 h. The mixture was evaporated at 60° C., the residue partitioned between brine and ethyl acetate, the organic layer evaporated and the residue purified by flash chromatography (Si—NH$_2$, methanol/dichloromethane 0 to 10%) to give the title compound (276 mg) as a white foam.
MS (ESI, m/z): 341.3 [(M+H)$^+$].

c) tert-Butyl N-[(1S)-1-(methylaminomethyl)-2,2-diphenyl-ethyl]carbamate was converted in analogy to example 1d-g and example 4a-b to give example 93 as a white solid.
MS (ESI, m/z): 392.2 [(M+H)$^+$].

Example 94

Preparation of (1a-66)

(4S)-4-Benzhydryl-9-hydroxy-6-methoxy-2-[(1R)-2,2,2-trifluoro-1-methyl-ethyl]-3,4-dihydropyrazino[1,2-c]pyrimidine-1,8-dione

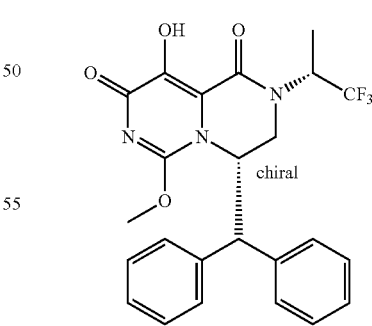

Example 94 was prepared from of (S)-tert-butyl (3-hydroxy-1,1-diphenylpropan-2-yl)carbamate (preparation: Baker, R. et al., PCT patent application WO 93/21181) in analogy to example 5d-5 k using (2R)-1,1,1-trifluoropropan-2-amine in step 5f and example 4a-4b.
MS (ESI, m/z): 474.3 [(M+H)$^+$].

Scheme 8
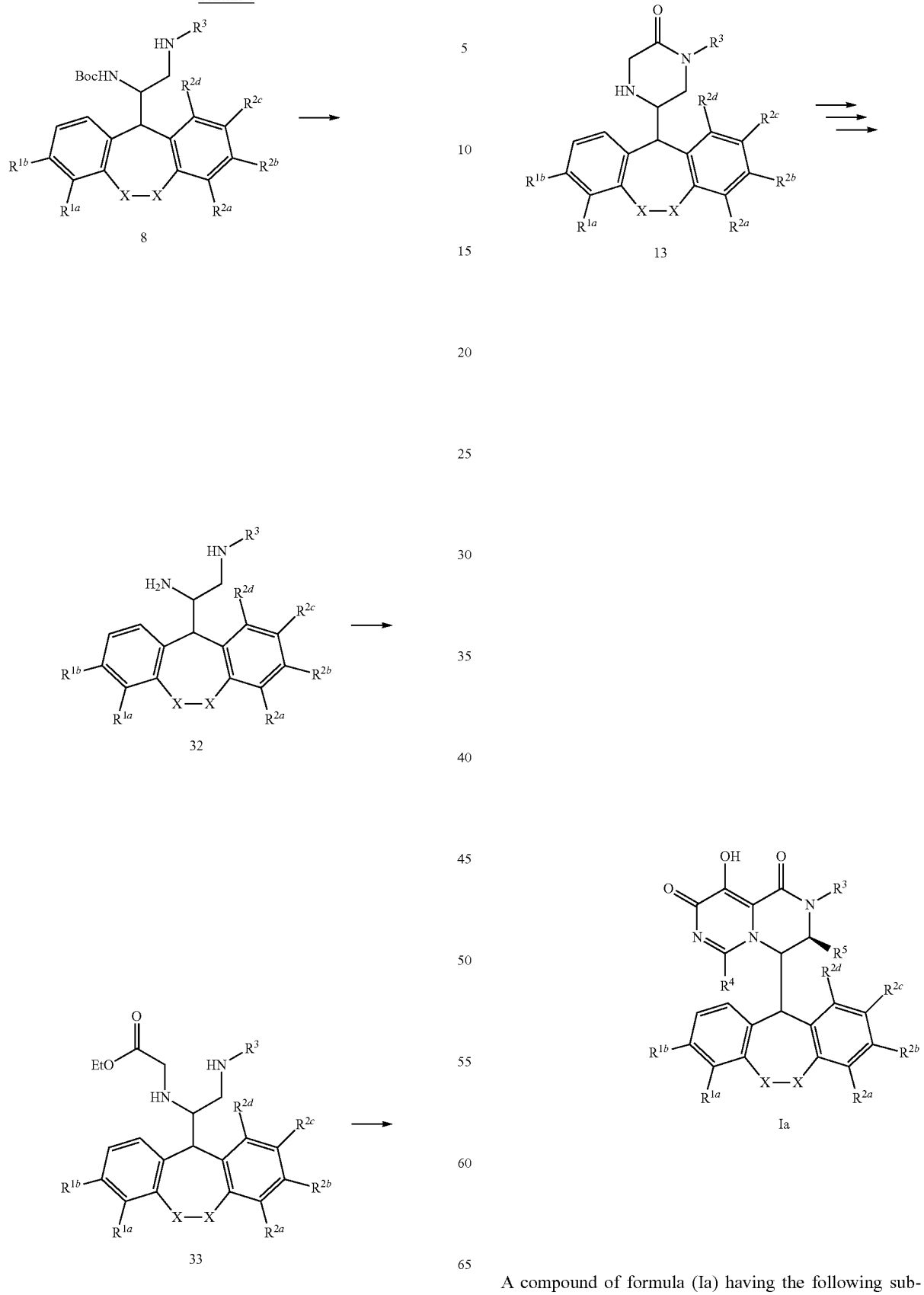
A compound of formula (Ia) having the following substitution pattern was prepared according to Scheme 8:

| | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| 1a-67 | H | H | H | H | H | H | — | 1-$CF_3$—cPr | OMe | H |

Compounds of formula Ia ($R^3$=1-$CF_3$-cPr) are prepared by the reaction of the diamine 32 with an alkyl 2-bromoacetate, e.g. ethyl 2-bromoacetate, lithium iodide and a base, e.g. triethylamine in a solvent such as tetrahydrofuran at 50° C., to give the esters 33.

Cyclization of the esters 33 was accomplished with and acid, preferably hydrochloric acid in water at elevated temperature, e.g. at 100° C. affording the piperaziones 13.

Example 95

Preparation of (1a-67)

4-Benzhydryl-9-hydroxy-6-methoxy-2-[1-(trifluoromethyl)cyclopropyl]-3,4-dihydropyrazino[1,2-c]pyrimidine-1,8-dione

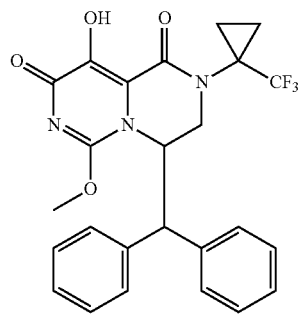 [SMILES: COc1nc(=O)c(O)c2n1C(C(c1ccccc1)c1ccccc1)CN(C1(C(F)(F)F)CC1)C2=O]

a) 3,3-Diphenyl-N1-[1-(trifluoromethyl)cyclopropyl]propane-1,2-diamine hydrochloride

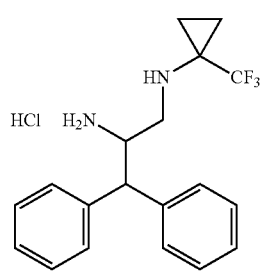 [SMILES: NC(CNC1(C(F)(F)F)CC1)C(c1ccccc1)c1ccccc1 ; Cl]

To a solution of tert-butyl N-[2,2-diphenyl-1-[[[1-(trifluoromethyl)cyclopropyl]amino]methyl]ethyl]carbamate (682 mg, prepared in analogy to the intermediate of example 94) in methanol (3 ml) was added at 22° C. hydrochloric acid in dioxane (4 M, 3.3 ml) and stirring was continued for 1.5 h. The mixture was evaporated and the residue containing the title compound (734 mg) used in the next step without purification.

MS (ESI, m/z): 335.2 [(M+H)$^+$].

b) Ethyl 2-[[2,2-diphenyl-1-[[[1-(trifluoromethyl)cyclopropyl]amino]methyl]ethyl]amino]acetate

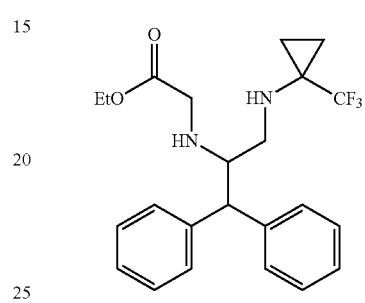

To a solution of 3,3-diphenyl-N1-[1-(trifluoromethyl)cyclopropyl]propane-1,2-diamine hydrochloride (728 mg) in tetrahydrofuran (31 ml) was subsequently added at 0° C. triethylamine (1.9 g), lithium iodide (84 mg) and ethyl 2-bromoacetate (1.84 g) and stirring was continued at 50° C. for 10 h. The mixture was partitioned between water and ethyl acetate, the organic layer was dried, evaporated and the residue purified by flash chromatography (silica gel, 5-80% ethyl acetate/n-heptane) to give the title compound (304 mg) as a 6:1 mixture of S and R enantiomers as a colorless oil.

MS (ESI, m/z):421.3 [(M+H)$^+$].

c) 5-Benzhydryl-1-[1-(trifluoromethyl)cyclopropyl]piperazin-2-one-hydrochloride

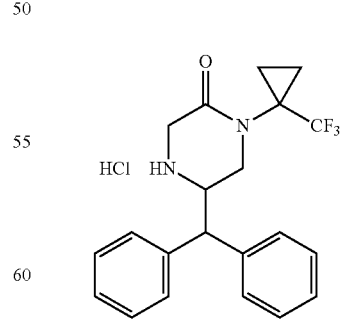

A mixture of ethyl 2-[[2,2-diphenyl-1-[[[1-(trifluoromethyl)cyclopropyl]amino]methyl]ethyl]-amino]acetate (290 mg) in aqueous hydrochloric acid (2 M, 3.5 ml) was heated to 100° C. for 30 min. The suspension was cooled to 0° C., treated carefully with solid potassium carbonate (1.24 g), the suspension was filtered, the residue washed with water and dried to give the title compound (283 mg) an off-white solid.

MS (ESI, m/z): 375.2 [(M+H)⁺].

d) 5-Benzhydryl-1-[1-(trifluoromethyl)cyclopropyl]piperazin-2-one-hydrochloride was converted to example 95 in analogy to example 4, obtained as a light yellow solid.

MS (ESI, m/z): 486.2 [(M+H)⁺].

Scheme 9

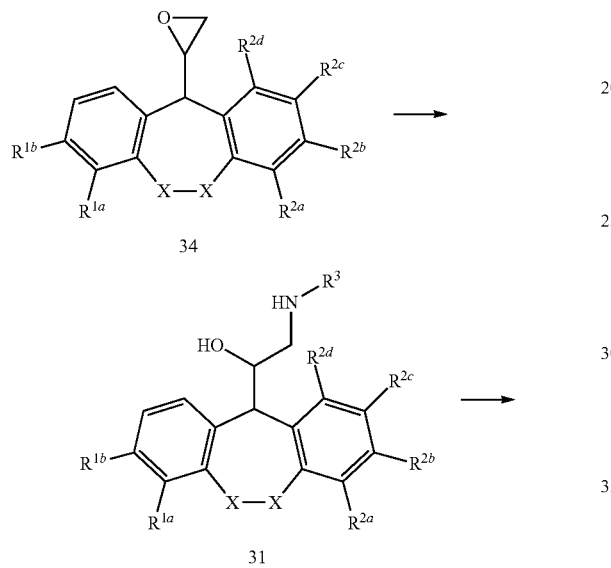

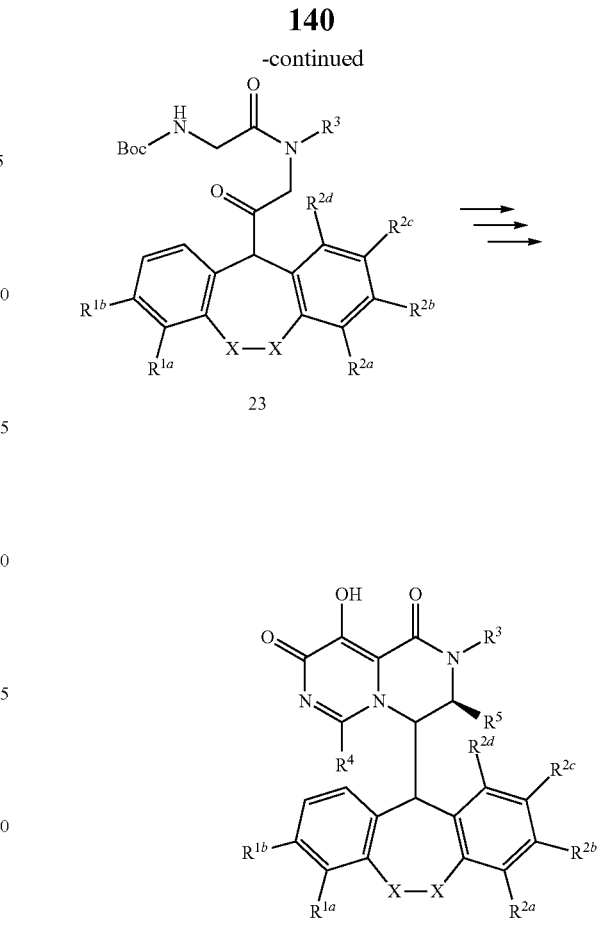

Compounds of Formula (Ia) Having the Following Substitution Pattern were Prepared According to Scheme 9:

| | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| Ia-68 | H | H | H | H | H | H | — | CH(Me)CH₂OMe | OMe | H |
| Ia-69 | H | H | H | H | H | H | — | CH₂CH₂OMe | OMe | H |
| Ia-70 | H | H | H | H | H | Br | — | Me | OMe | H |

Compounds of formula Ia (R³=alkylethers, Me) are prepared by the reaction of oxiranes 34 and aminoalkylethers or methylamine in a solvent such as alcohols, e.g. isopropanol at 70° C. to give the aminoalcohols 31.

Coupling of the aminoalcohols 31 with t-butyloxycarbonyl-glycine to the amides 35 can be accomplished with an activating agent such as HATU (i.e. [O-(7-azabenzotriazol-1-yl)-N,N,N',N'-tetramethyluronium-hexafluorphosphate]) and a base such as diisopropylethylamine in a solvent such as tetrahydrofuran or preferably dimethylformamide at room temperature.

Oxidation of the alcohol function in compounds 35 could be accomplished by Dess-Martin-periodinan (1,1,1-triacetoxy-1,1-dihydro-1,2-benziodoxol-3(1H)-one) oxidation in a solvent such as dichloromethane at 0-20° C. to give the ketones 23.

-continued

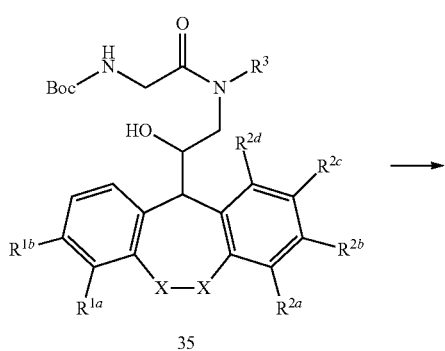

Example 96-99

Preparation of (1a-68)

4-benzhydryl-9-hydroxy-6-methoxy-2-(2-methoxy-1-methyl-ethyl)-3,4-dihydropyrazino[1,2-c]pyrimidine-1,8-dione

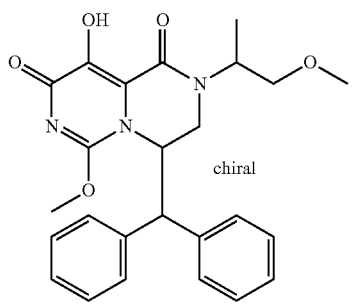 [SMILES: COCC(C)N1CC(C(c2ccccc2)c2ccccc2)n2c(OC)nc(=O)c(O)c2C1=O]

chiral a) 3-[(2-Methoxy-1-methyl-ethyl)amino]-1,1-diphenyl-propan-2-ol

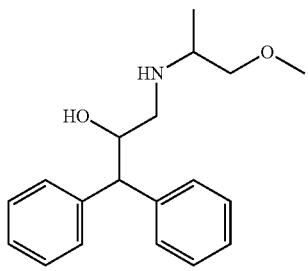 [SMILES: COCC(C)NCC(O)C(c1ccccc1)c1ccccc1]

To a solution of 2-benzhydryloxirane (100 mg, preparation: Clark, J. A. et al., Journal of Medicinal Chemistry (1979), 22(11), 1373-9) in isopropanol (2.0 ml) was added at 22° C. 2-amino-1-methoxypropane (212 mg) and stirring was continued at 70° C. for 6 h. The mixture was evaporated and the residue purified by flash chromatography (silica gel, 20-100% ethyl acetate/n-heptane) to give the title compound (86 mg) as a colorless oil.

MS (ESI, m/z): 300.2 [(M+H)$^+$].

b) tert-Butyl N-[2-[(2-hydroxy-3,3-diphenyl-propyl)-(2-methoxy-1-methyl-ethyl)amino]-2-oxo-ethyl]carbamate

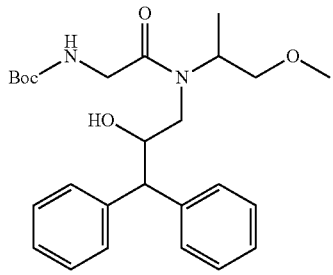 [SMILES: COCC(C)N(CC(O)C(c1ccccc1)c1ccccc1)C(=O)CNC(=O)OC(C)(C)C]

To a solution of Boc-glycine (1.76 g) in dimethylformamide (8 ml) was added 1-[bis(dimethylamino)methylene]-1H-1,2,3-triazolo[4,5-b]pyridinium 3-oxid hexafluorophosphate (2.1 g) and stirring was continued at 22° C. for 15 min. A solution of 3-[(2-methoxy-1-methyl-ethyl)amino]-1,1-diphenyl-propan-2-ol (1.50 g) in dimethylformamide (24 ml) was added, which was followed by the addition of N,N-diisopropylethylamine (1.94 g) and stirring was continued for 6 h. The mixture was evaporated and the residue partitioned between water and ethyl acetate, the organic layer was dried, evaporated and the residue purified by flash chromatography (silica gel, 50-100% ethyl acetate/n-heptane) to give the title compound (2.10 g) as a colorless oil.

MS (ESI, m/z): 457.4 [(M+H)$^+$].

c) tert-Butyl N-[2-[(2-methoxy-1-methyl-ethyl)-(2-oxo-3,3-diphenyl-propyl)amino]-2-oxo-ethyl]carbamate

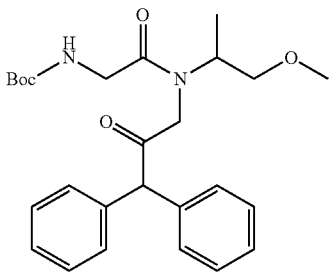 [SMILES: COCC(C)N(CC(=O)C(c1ccccc1)c1ccccc1)C(=O)CNC(=O)OC(C)(C)C]

To a solution of tert-butyl N-[2-[(2-hydroxy-3,3-diphenyl-propyl)-(2-methoxy-1-methyl-ethyl)amino]-2-oxo-ethyl]carbamate (2.0 g) in dichloromethane (100 ml) was added at 0° C. a solution of 1,1,1-triacetoxy-1,1-dihydro-1,2-benziodoxol-3(1H)-one in dichloromethane (15%, 27.2 g) and stirring was continued at 22° C. for 18 h. The mixture was diluted with isopropanol (6 ml), stirring was continued for 1 h, The mixture was washed with saturated aqueous sodium bicarbonate, the organic layer was dried, evaporated and the residue purified by flash chromatography (silica gel, 10-50% ethyl acetate/n-heptane) to give the title compound (1.45 g) as a colorless oil.

MS (ESI, m/z): 455.3 [(M+H)$^+$].

d) 5-Benzhydryl-1-(2-methoxy-1-methyl-ethyl)piperazin-2-one

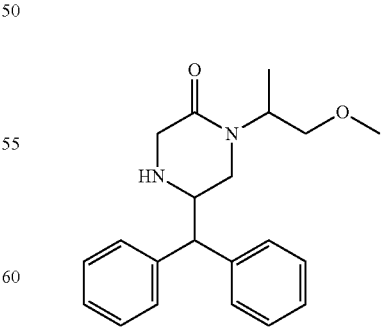

tert-Butyl N-[2-[(2-methoxy-1-methyl-ethyl)-(2-oxo-3,3-diphenyl-propyl)amino]-2-oxo-ethyl]carbamate was converted according to example 29 d-e to give the title compound as a mixture of four isomers. The mixture (900 mg,

143 yellow oil) was separated by chiral supercritical fluid chromatography (AD-H column, MeOH) to give a first eluting fraction A (210 mg), a second eluting fraction B (115 mg), a third eluting fraction C (130 mg) and a fourth eluting fraction D (165 mg).

MS (ESI, m/z) of all 4 fractions: 339.2 [(M+H)$^+$].

e) Fraction A-D were converted according to example 29 f-h to give example 96-99, respectively, as light brown solids.

MS (ESI, m/z): 450.3 [(M+H)$^+$].

Example 100-101

Preparation of (1a-69)

4-Benzhydryl-9-hydroxy-6-methoxy-2-(2-methoxyethyl)-3,4-dihydropyrazino[1,2-c]pyrimidine-1,8-dione

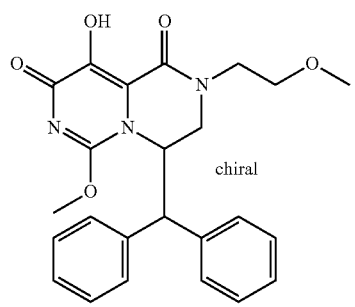 [SMILES: COCCN1CC(C(c2ccccc2)c2ccccc2)n2c(OC)nc(=O)c(O)c2C1=O]

a) 5-Benzhydryl-1-(2-methoxyethyl)piperazin-2-one

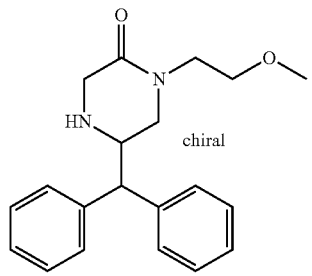 [SMILES: COCCN1CC(C(c2ccccc2)c2ccccc2)NCC1=O]

The racemic title compound was prepared according to example 96-99a-d but using 2-methoxyethanamine in step a. The racemate (1.05 g, light yellow oil) was separated by chiral supercritical fluid chromatography (IC, 25% methanol) to give a first eluting fraction A (450 mg) and a second eluting fraction B (360 mg). MS (ESI, m/z) of both fractions fractions: 325.2 [(M+H)$^+$].

b) Fractions A and B were converted according to example 29 f-h to give example 100 and 101, respectively, as light brown solids. MS (ESI, m/z): 450.3 [(M+H)$^+$].

144

Example 102

Preparation of (1a-70)

4-[(2-Bromophenyl)-phenyl-methyl]-9-hydroxy-6-methoxy-2-methyl-3,4-dihydropyrazino[1,2-c]pyrimidine-1,8-dione

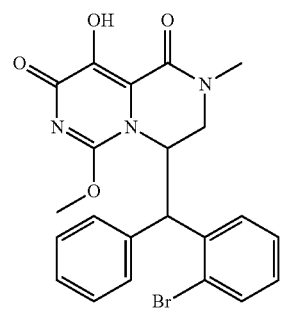 [SMILES: COc1nc(=O)c(O)c2n1C(C(c1ccccc1)c1ccccc1Br)CN(C)C2=O]

a) 2-[(2-Bromophenyl)-phenyl-methyl]oxirane

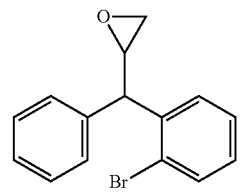 [SMILES: Brc1ccccc1C(c1ccccc1)C1CO1]

To a solution of trimethylsulfoxoniumiodide (5.60 g) in dimethylsulfoxide (20 ml) was added at 22° C. potassium tert-butoxide (2.85 g) and stirring was continued for 30 min. 2-(2-Bromophenyl)-2-phenylacetaldehyde (5.00 g, preparation: Besandre, R. et al., Organic Letters (2013), 15(7), 1666-1669) was added and stirring was continued at 50° C. for 45 min. The mixture was partitioned between n-heptane (30 ml) and water (30 ml) containing acetic acid (3 ml), the organic layer was dried and evaporated to give the crude title compound (3.20 g) as a light yellow oil, which was used without purification.

b) 2-[(2-Bromophenyl)-phenyl-methyl]oxirane was converted according to the procedures for examples 96-99 but using methylamine in step a to give example 102 as a mixture of 4 isomers.

MS (ESI, m/z): 470.2 and 472.2 [(M+H)$^+$].

Scheme 10

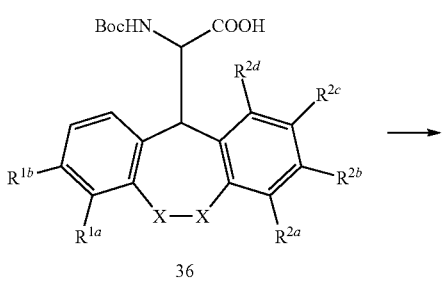

36

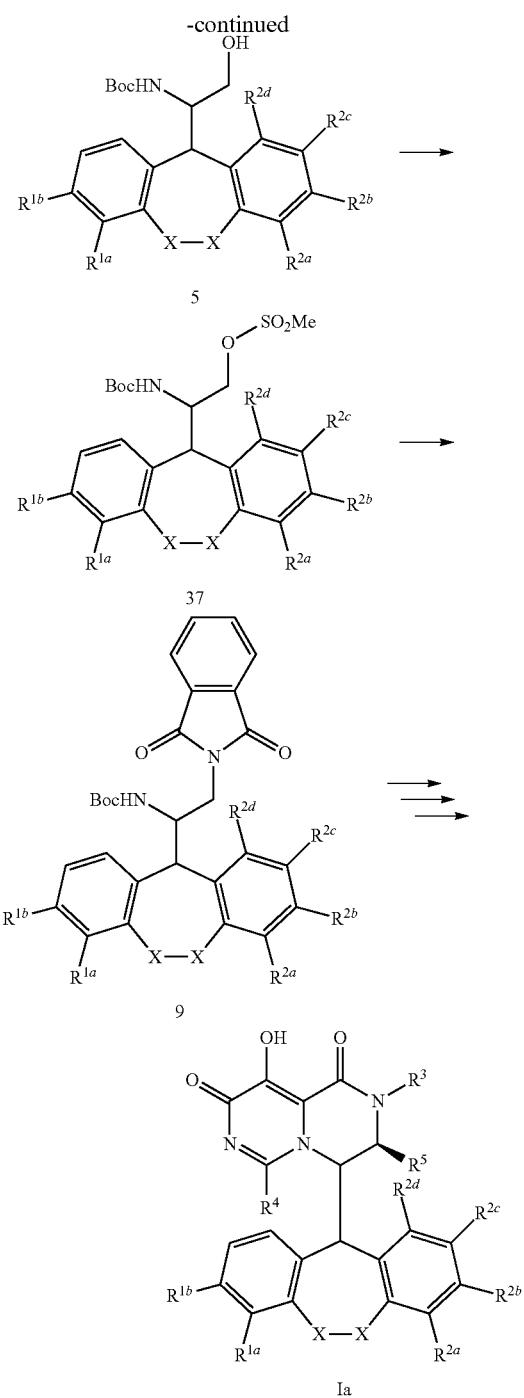

5

37

9

Ia

A Compound of Formula (Ia) Having the Following Substitution Pattern was Prepared According to Scheme 10:

|      | $R^{1a}$ | $R^{1b}$ | $R^{2a}$ | $R^{2b}$ | $R^{2c}$ | $R^{2d}$ | X-X | $R^3$ | $R^4$ | $R^5$ |
|------|----------|----------|----------|----------|----------|----------|-----|-------|-------|-------|
| 1a-71 | H | F | H | F | H | H | — | iPr | OMe | H |

Compounds of formula Ia ($R^{1b}=R^{2b}=F$) are prepared by the reduction of acids 36 via the anhydride intermediates using an alkyl chloroformate, preferably isobutyl chloroformate and a base, preferably N-methyl morpholine in tetrahydrofuran at −20° C., which was followed by the reduction of the intermediate anhydrides using sodium borohydride in a solvent such as water to give the alcohols 5.

Alcohols 5 can be activated with methanesulfonyl chloride and a base, e.g. triethylamine in a solvent such as dichloromethane at 0° C. furnishing the mesylates 37.

Substitution of the the mesylates 37 was effected with phthalimide potassium salt in dimethylformamide at 20-70° C., affording the phthalimides 9.

Example 103

Preparation of (1a-71)

(4S)-4-[Bis(4-fluorophenyl)methyl]-9-hydroxy-2-isopropyl-6-methoxy-3,4-dihydropyrazino[1,2-c]pyrimidine-1,8-dione

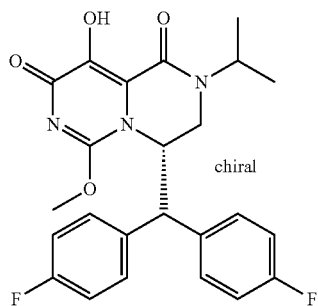 [SMILES: COc1nc(=O)c(O)c2n1[C@@H](C(c1ccc(F)cc1)c1ccc(F)cc1)CN(C(C)C)C2=O]

a) tert-Butyl N-[(1S)-2,2-bis(4-fluorophenyl)-1-(hydroxymethyl)ethyl]carbamate

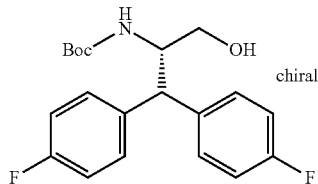 [SMILES: CC(C)(C)OC(=O)N[C@H](CO)C(c1ccc(F)cc1)c1ccc(F)cc1]

To a solution of (S)-2-((tert-butoxycarbonyl)amino)-3,3-bis(4-fluorophenyl)propanoic acid (3.60 g, preparation: Appell, R. B. et al., Organic Process Research & Development (2013), 17(1), 69-76) in tetrahydrofuran (50 ml) was added subsequently at −20° C. N-methyl morpholine (1.16 g) and isobutyl chloroformate (1.43 g) and stirring was continued at −20° C. for 20 min. A solution of sodium borohydride (722 mg) in water (6 ml) was added dropwise at −15° C. and stirring was continued at −15° C. for 1 h. The mixture was partitioned between aqueous sodium carbonate and ethyl acetate, the organic layer was dried and evaporated to give the crude title compound (4.58 g) as a yellow oil, which was used without further purification in the next step.

b) [(2S)-2-(tert-Butoxycarbonylamino)-3,3-bis(4-fluorophenyl)propyl]methanesulfonate

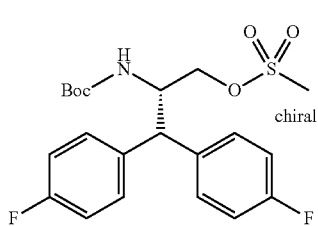 [SMILES: CC(C)(C)OC(=O)N[C@H](COS(C)(=O)=O)C(c1ccc(F)cc1)c1ccc(F)cc1]

To a solution of tert-butyl N-[(1S)-2,2-bis(4-fluorophenyl)-1-(hydroxymethyl)ethyl]carbamate (3.47 g) in dichloromethane (40 ml) was added subsequently at 0° C. triethylamine (1.93 g) and methanesulfonyl chloride (1.31 g) and stirring was continued at 0° C. for 30 min. The mixture was washed with aqueous sodium hydrogencarbonate, the organic layer was dried and evaporated to give the crude title compound (4.92 g) as an orange oil, which was used without further purification in the next step.

MS (ESI, m/z): 342.2 [(M-Boc+H)$^+$].

c) tert-Butyl N-[(1S)-1-[(1,3-dioxoisoindolin-2-yl)methyl]-2,2-bis(4-fluorophenyl)ethyl]carbamate

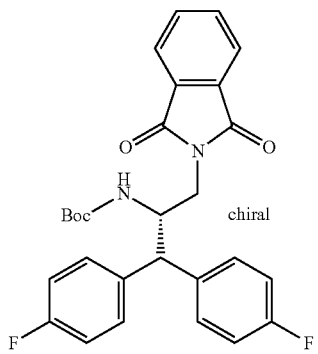 [SMILES: CC(C)(C)OC(=O)N[C@H](CN1C(=O)c2ccccc2C1=O)C(c1ccc(F)cc1)c1ccc(F)cc1]

To a solution of [(2S)-2-(tert-butoxycarbonylamino)-3,3-bis(4-fluorophenyl)propyl]methanesulfonate (4.22 g) in dimethylformamide (40 ml) was added at 22° C. phthalimide potassium salt (3.54 g) and stirring was continued at 22° C. for 16 h and at 70° C. for 4 h. The mixture was partitioned between aqueous sodium hydrogencarbonate and ethyl acetate, the organic layer was dried and evaporated to give the crude title compound (4.71 g) as a yellow solid, which was used without further purification in the next step.

MS (ESI, m/z): 393.2 [(M-Boc+H)].

d) tert-Butyl N-[(1S)-1-[(1,3-dioxoisoindolin-2-yl)methyl]-2,2-bis(4-fluorophenyl)ethyl]carbamate was converted according to the procedures for example 1b-g and example 4a-b to give example 103 as an orange powder.

MS (ESI, m/z): 456.3 [(M+H)$^+$].

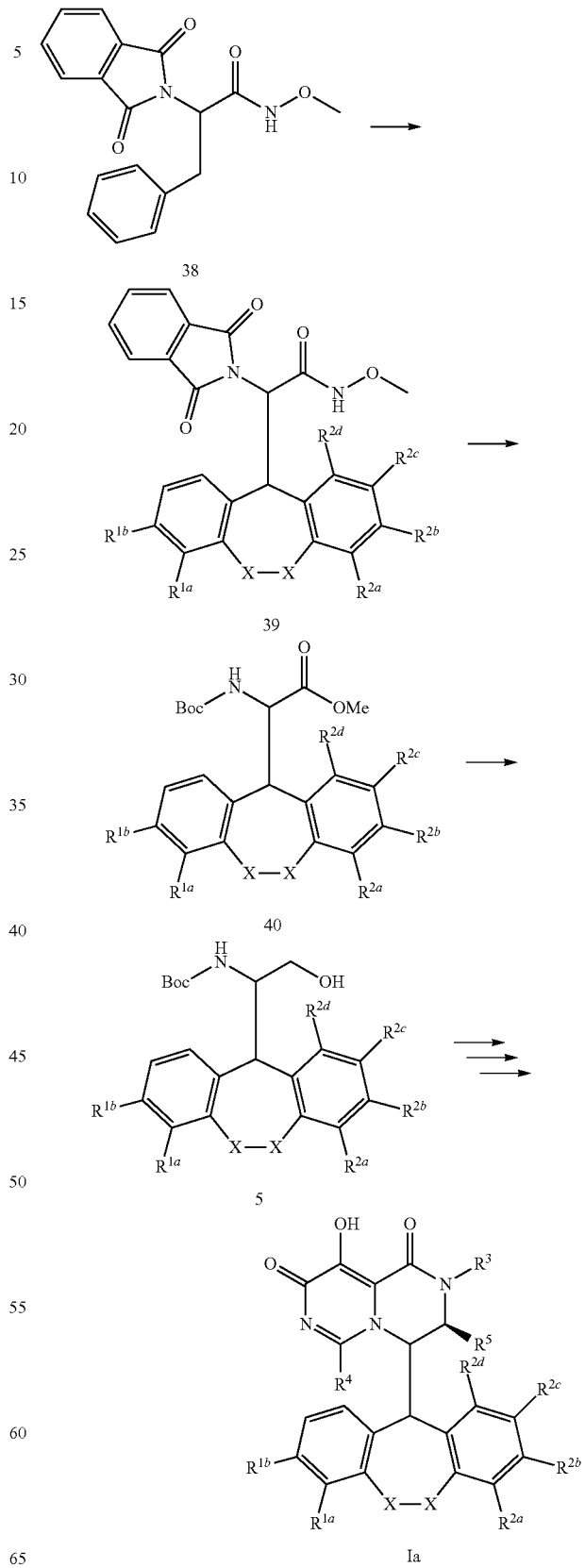

Scheme 11

149

A Compound of Formula (Ia) Having the Following Substitution Pattern was Prepared According to Scheme 11:

| | $R^{1a}$ $R^{1b}$ | $R^{2a}$ $R^{2b}$ | $R^{2c}$ $R^{2d}$ | X-X | $R^3$ | $R^4$ | $R^5$ |
|---|---|---|---|---|---|---|---|
| 1a-72 | H  H | H  Cl | H  H | — | iPr | OMe | H |

Compounds of formula Ia ($R^{2b}$=Cl) are prepared by the reaction of amides 38 with a halogen-4-iodobenzene, e.g. with 1-chloro-4-iodobenzene, palladium (II) acetate, silver acetate, sodium dihydrogen phosphate dihydrate and a base, e.g. 2,6-lutidine in a solvent such as hexafluoroisopropanol at 100° C. furnishing the amides 39.

Amides 39 can be reacted with methanol in the presence of boron trifluoride diethyl etherate at elevated temperature affording the intermediate methyl esters, which are reacted with ethylenediamine in a solvent mixture of methanol and dichloromethane to give the intermediate amines, which can be reprotected with the Boc group using Boc-anhydride and a base such as diisopropylethylamine in in dichloromethane at room temperature yielding the esters 40.

Esters 40 can be reduced with a hydride, preferably lithiumaluminium hydride in a solvent such as tetrahydrofuran at 0° C. affording the alcohols 5.

Example 104

Preparation of (1a-72)

(4S)-4-[(R)-(4-Chlorophenyl)-phenyl-methyl]-9-hydroxy-2-isopropyl-6-methoxy-3,4-dihydropyrazino[1,2-c]pyrimidine-1,8-dione

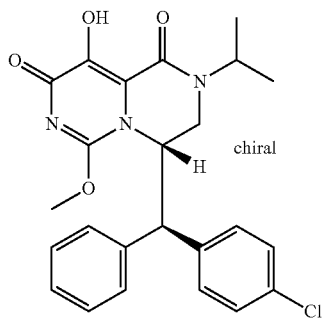 [SMILES: COc1nc(=O)c(O)c2n1[C@@H]([C@H](c1ccccc1)c1ccc(Cl)cc1)CN(C(C)C)C2=O]

a) (2S,3R)-3-(4-Chlorophenyl)-2-(1,3-dioxoisoindolin-2-yl)-N-methoxy-3-phenyl-propanamide

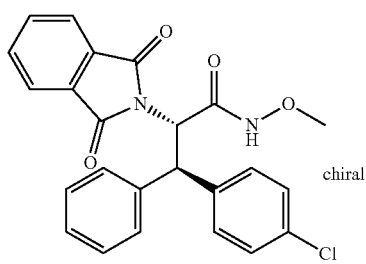 [SMILES: CONC(=O)[C@H]([C@H](c1ccccc1)c1ccc(Cl)cc1)N1C(=O)c2ccccc2C1=O]

150

To (S)-2-(1,3-dioxoisoindolin-2-yl)-N-methoxy-3-phenylpropanamide (1.00 g, preparation: Chen, G. et al., Journal of the American Chemical Society (2015), 137(9), 3338-3351) in hexafluoroisopropanol (20 ml) was subsequently added at 22° C. 1-chloro-4-iodobenzene (2.21 g), sodium dihydrogen phosphate dihydrate (1.44 g), silver acetate (1.03 g), 2,6-lutidine (198 mg) and palladium (II) acetate (208 mg) and stirring was continued in a sealed tube at 100° C. for 72 h. The mixture was evaporated and the residue purified by flash chromatography (silica gel, 0-100% ethyl acetate/n-heptane) to give the title compound (0.93 g) as a light yellow solid.

MS (ESI, m/z): 435.2 [(M+H)$^+$].

b) Methyl (2S,3R)-2-(tert-butoxycarbonylamino)-3-(4-chlorophenyl)-3-phenyl-propanoate

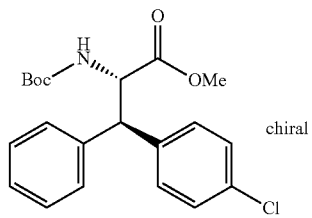 [SMILES: COC(=O)[C@@H](NC(=O)OC(C)(C)C)[C@H](c1ccccc1)c1ccc(Cl)cc1]

To (2S,3R)-3-(4-chlorophenyl)-2-(1,3-dioxoisoindolin-2-yl)-N-methoxy-3-phenyl-propanamide (930 mg) in methanol (61 ml) was added at 22° C. boron trifluoride diethyl etherate (1.82 g) and stirring was continued at 100° C. for 16 h. The mixture containing the desired methyl ester was evaporated and the residue dissolved in a mixture of methanol (10 ml) and dichloromethane (10 ml) to which was added at 22° C. ethylenediamine (643 mg) and stirring was continued at 40° C. for 16 h. The mixture containing the deprotected amine was evaporated, the residue dissolved in dichloromethane (24 ml) and subsequently was added diisopropylethyl amine (553 mg) and Boc-anhydride (933 mg) and stirring was continued at 22° C. for 8 h. The mixture was washed with aqueous sodium hydrogencarbonate, the organic layer was dried, evaporated and the residue purified by flash chromatography (silica gel, 0-100% ethyl acetate/n-heptane) to give the title compound (0.50 g) as a yellow oil.

MS (ESI, m/z): 290.1 [(M-Boc+H)$^+$].

c) tert-Butyl N-[(1S,2R)-2-(4-chlorophenyl)-1-(hydroxymethyl)-2-phenyl-ethyl]carbamate

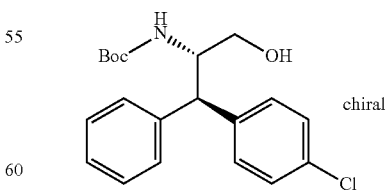

To a mixture of lithium aluminium hydride (63 mg) in tetrahydrofuran (5 ml) was added dropwise at 0° C. a solution of methyl (2S,3R)-2-(tert-butoxycarbonylamino)-3-(4-chlorophenyl)-3-phenyl-propanoate (500 mg) in tetrahydrofuran (5 ml) and stirring was continued at 0° C. for 3 h. Water (50 al) was added followed by the subsequent addition of an aqueous solution of sodium hydroxide (15%, 50 al), water (50 al) and sodium sulfate (3.1 g) and stirring was continued for 30 min. The suspension was filtered and the filtrate evaporated to give the crude title compound (0.42 g) as a white foam, which was used without further purification in the next step.

MS (ESI, m/z): 306.1 [(M-isobuten+H)$^+$].

d) tert-Butyl N-[(1S,2R)-2-(4-chlorophenyl)-1-(hydroxymethyl)-2-phenyl-ethyl]carbamate was converted in analogy to example 103b-d to give example 104 as a yellow solid.

MS (ESI, m/z): 454.1 [(M+H)$^+$].

Scheme 12

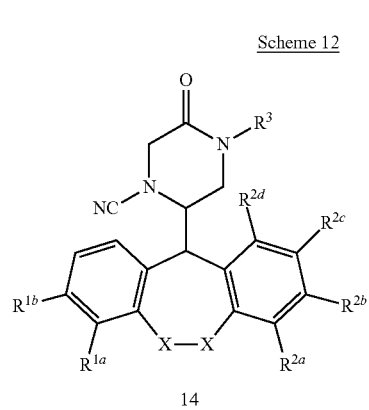

14

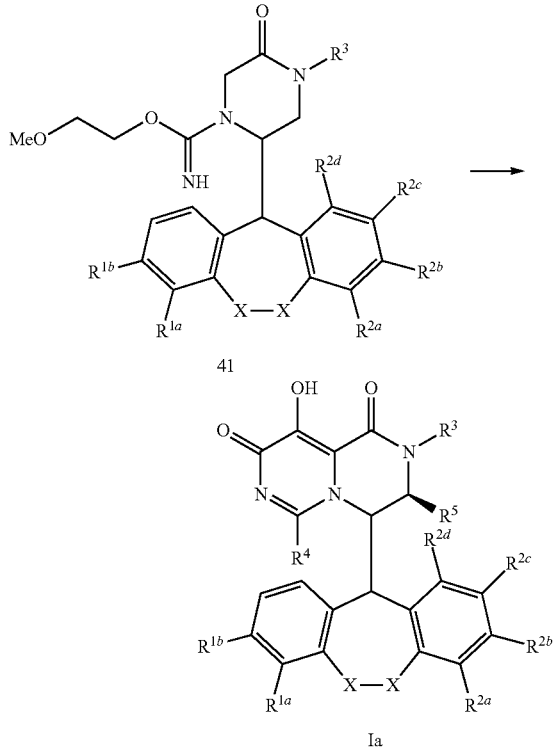

41

Ia

A Compound of formula (Ia) having the following substitution pattern was prepared according to Scheme 12:

|  | $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|---|
| 1a-73 | H | H | H | H | H | H | — | Me | OCH$_2$CH$_2$OMe | H |

Compounds of formula Ia (R$^4$=OCH$_2$CH$_2$OMe) are prepared by the reaction of nitriles 14 with alkoxyethanoles, e.g. with 2-methoxyethanol and a base, e.g. sodium hydroxide in water at elevated temperature, e.g at 70° C. to give the isourea derivatives 41.

Example 105

Preparation of (1a-73)

(4S)-4-Benzhydryl-9-hydroxy-6-(2-methoxyethoxy)-2-methyl-3,4-dihydropyrazino[1,2-c]pyrimidine-1,8-dione

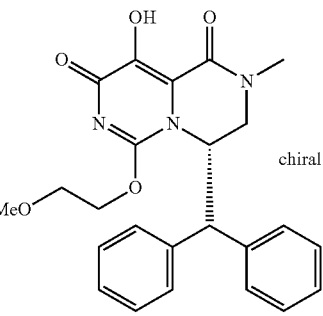

a) 2-Methoxyethyl (2S)-2-benzhydryl-4-methyl-5-oxo-piperazine-1-carboximidate

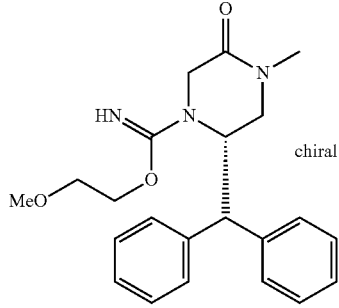 [SMILES: COCCOC(=N)N1CC(=O)N(C)C[C@@H]1C(c1ccccc1)c1ccccc1]

To a solution of (S)-2-benzhydryl-4-methyl-5-oxopiperazine-1-carbonitrile (122 mg, prepared according to example 93) in 2-methoxyethanol (5 ml) was added at 22° C. an aqueous solution of sodium hydroxide (20%, 195 mg) and stirring was continued at 70° C. for 20 min. The mixture was evaporated, the residue partitioned between water and dichloromethane, the organic layer was dried and evaporated to give the crude title compound (147 mg) as a colorless oil.

MS (ESI, m/z): 382.3 [(M+H)$^+$].

b) To a solution of 2-methoxyethyl (2S)-2-benzhydryl-4-methyl-5-oxo-piperazine-1-carboximidate (143 mg) in tetrahydrofuran (1.8 ml) was added dropwise at −50° C. a solution of lithium hexamethyldisilazide in tetrahydrofuran (1 M, 1.1 ml) and stirring was continued at −50° C. for 5 min. A solution of dimethyl oxalate (133 mg) in tetrahydrofuran (0.6 ml) was added and stirring was continued at −50° C. for 40 min. The mixture was quenched at −50° C. with aqueous hydrochloric acid (1 N, 2 ml), warmed to 22° C., extracted with dichloromethane, the organic layer was dried and evaporated to give the crude intermediate (211 mg), which was not yet ring closed. The intermediate was dissolved in tetrahydrofuran (1.5 ml) and treated at −40° C. with a solution of lithiumhexamethyldisilazide in tetrahydrofuran (1 M, 0.33 ml) and stirring was continued at −40° C. for 1 h. The mixture was quenched at −20° C. with aqueous hydrochloric acid (1 N, 1 ml), warmed to 22° C., extracted with dichloromethane, the organic layer was dried, evaporated and the residue purified by preparative HPLC (RP-18, acetonitrile/water containing 0.1% triethylamine) to give example 105 (7 mg) as a light yellow solid.

MS (ESI, m/z): 436.3 [(M+H)$^+$].

A Compound of Formula (Ia) Having the Following Substitution Pattern was Prepared According to Scheme 5:

| $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|
| 1a-74 H | H | H | H | H | H | — | iPr | CH$_2$OH | H |

Example 106

Preparation of (1a-74)

(4S)-4-Benzhydryl-9-hydroxy-6-(hydroxymethyl)-2-isopropyl-3,4-dihydropyrazino[1,2-c]pyrimidine-1,8-dione

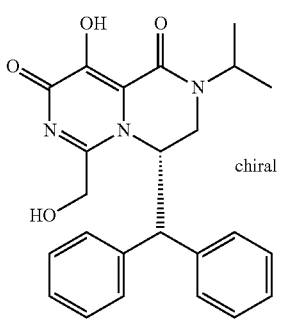 [SMILES: CC(C)N1C[C@H](C(c2ccccc2)c2ccccc2)n2c(CO)nc(=O)c(O)c2C1=O]

Example 106 was prepared in analogy to example 59 starting with example 49 to give the compound as a light yellow solid.

MS (ESI, m/z): 420.2 [(M+H)$^+$].

A Further Compound of Formula (Ia) Having the Following Substitution Pattern was Prepared According to Scheme 4:

| $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|
| 1a-75 H | H | H | H | H | H | CH$_2$CH$_2$ | iPr | SH | H |

Example 107

Preparation of (1a-75)

4-(6,11-Dihydro-5H-dibenzo[2,1-b:1',2'-e][7]annulen-11-yl)-9-hydroxy-2-isopropyl-6-sulfanyl-3,4-dihydropyrazino[1,2-c]pyrimidine-1,8-dione

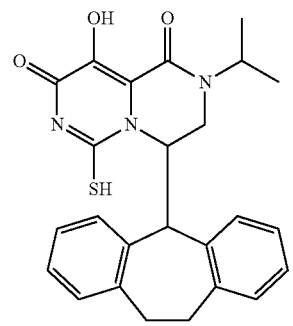 [SMILES: CC(C)N1CC(C2c3ccccc3CCc3ccccc32)n2c(S)nc(=O)c(O)c2C1=O]

The title compound was prepared from example 42 in analogy to the procedure for example 39 to give the compound as a yellow solid.

MS (ESI, m/z): 448.1 [(M+H)$^+$].

A further compound of formula (Ia) having the following substitution pattern was prepared according to Scheme 5:

| $R^{1a}$ | $R^{1b}$ | $R^{2a}$ | $R^{2b}$ | $R^{2c}$ | $R^{2d}$ | X-X | $R^3$ | $R^4$ | $R^5$ |
|---|---|---|---|---|---|---|---|---|---|
| 1a-76 H | H | H | H | H | H | CH$_2$CH$_2$ | iPr | SO$_2$Me | H |

Example 108

Preparation of (1a-76)

(4S)-4-(6,11-Dihydro-5H-dibenzo[2,1-b:1',2'-e][7]annulen-11-yl)-9-hydroxy-2-isopropyl-6-methylsulfonyl-3,4-dihydropyrazino[1,2-c]pyrimidine-1,8-dione

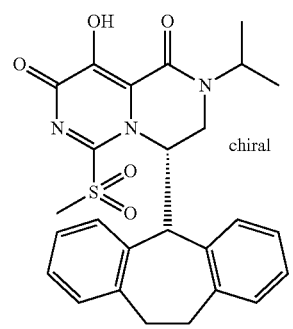 [SMILES: CC(C)N1C[C@H](C2c3ccccc3CCc3ccccc32)n2c(S(C)(=O)=O)nc(=O)c(O)c2C1=O]

The title compound was prepared from example 42 in analogy to the procedure for example 49 to give the compound as a white solid.

MS (ESI, m/z) 494.1 [(M+H)$^+$].

Scheme 13

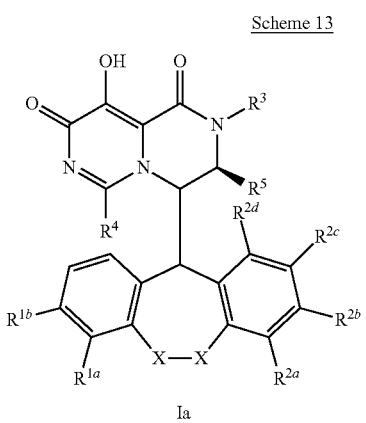

Ia

Compounds of formula Ia ($R^{10}$=CH$_3$CO) are prepared by the reaction of compounds of formula Ia ($R^{10}$=H) with acetic anhydride in the presence of a base such as pyridine and a catalytic amount of 4-dimethylaminopyridine, in a solvent such as dichloromethane at 22° C.

Compounds of formula Ia ($R^{10}$=CH$_3$COOCH$_2$ and CH$_3$OCOOCH$_2$) are prepared by the reaction of compounds of formula Ia ($R^{10}$=H) with bromomethyl acetate or iodomethyl methyl carbonate, respectively, tetrabutylammonium hydrogen sulfate and a base such as potassium carbonate in solvent mixture of dichloromethane and water at 22° C.

Example 109

Preparation of (1a-77)

[(4S)-4-Benzhydryl-2-isopropyl-6-methoxy-1,8-dioxo-3,4-dihydropyrazino[1,2-c]pyrimidin-9-yl] acetate

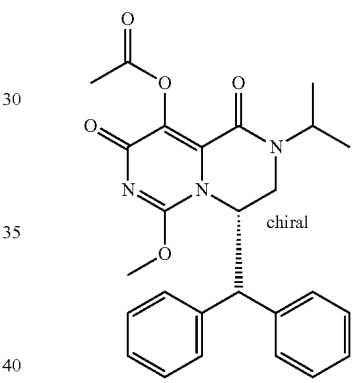

To a solution of (4S)-4-benzhydryl-9-hydroxy-2-isopropyl-6-methoxy-3,4-dihydropyrazino[1,2-c]pyrimidine-1,8-dione (20 mg, from example 4) in dichloromethane (1 ml) were added subsequently at 22° C. pyridine (12 mg) acetic anhydride (15 mg) and 4-dimethylaminopyridine (0.3 mg) and stirring was continued at 22° C. for 48 h. The mixture was evaporated, the residue purified by flash chromatography (silica gel, 0-5% methanol/dichloromethane), the product containing fractions were evaporated, the residue triturated with n-heptane and dried to give the title compound (15 mg) as a white solid.

MS (ESI, m/z): 462.4 [(M+H)$^+$].

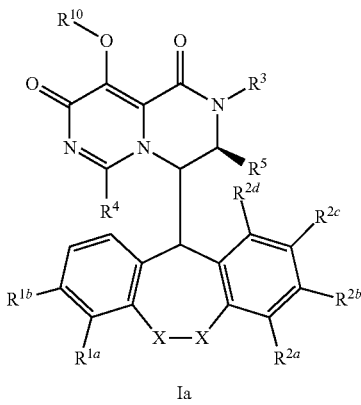

Ia

Compounds of formula (Ia) having the following substitution pattern were prepared according to Scheme 13:

|       | $R^{1a}$ | $R^{1b}$ | $R^{2a}$ | $R^{2b}$ | $R^{2c}$ | $R^{2d}$ | X-X | $R^3$ | $R^4$ | $R^5$ | $R^{10}$ |
|-------|------|------|------|------|------|------|-----|-----|-----|-----|----------|
| 1a-77 | H | H | H | H | H | H | — | iPr | OMe | H | CH$_3$CO |
| 1a-78 | H | H | H | H | H | H | — | iPr | OMe | H | CH$_3$COOCH$_2$ |
| 1a-79 | H | H | H | H | H | H | — | iPr | OMe | H | CH$_3$OCOOCH$_2$ |

Example 110

Preparation of (1a-78)

[(4S)-4-Benzhydryl-2-isopropyl-6-methoxy-1,8-dioxo-3,4-dihydropyrazino[1,2-c]pyrimidin-9-yl]oxymethyl acetate

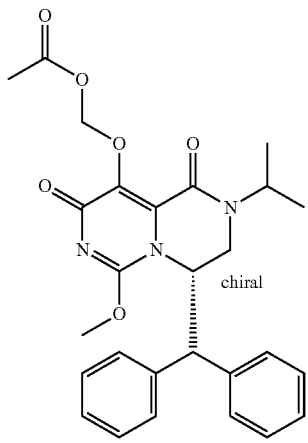 [SMILES: COc1nc(=O)c(OCOC(C)=O)c2n1[C@@H](C(c1ccccc1)c1ccccc1)CN(C(C)C)C2=O]

To a solution of (4S)-4-benzhydryl-9-hydroxy-2-isopropyl-6-methoxy-3,4-dihydropyrazino[1,2-c]pyrimidine-1,8-dione (20 mg, from example 4) in dichloromethane (0.3 ml) were added subsequently at 22° C. a solution of potassium carbonate (19 mg) in water (0.25 ml), tetrabutylammonium hydrogen sulfate (16 mg) and a solution of bromomethyl acetate (30 mg) in dichloromethane (0.3 ml) and stirring was continued at 22° C. for 96 h. The mixture was evaporated, the residue purified by flash chromatography (silica gel, ethyl acetate then 0-5% methanol/dichloromethane) to give the title compound (9 mg) as a colorless oil.

MS (ESI, m/z): 492.4 [(M+H)$^+$].

Example 111

Preparation of (1a-79)

[(4S)-4-Benzhydryl-2-isopropyl-6-methoxy-1,8-dioxo-3,4-dihydropyrazino[1,2-c]pyrimidin-9-yl]oxymethyl methyl carbonate

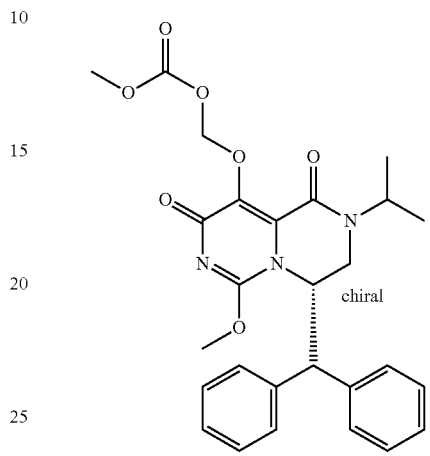

To a solution of (4S)-4-benzhydryl-9-hydroxy-2-isopropyl-6-methoxy-3,4-dihydropyrazino[1,2-c]pyrimidine-1,8-dione (40 mg, from example 4) in dichloromethane (0.3 ml) were added subsequently at 22° C. a solution of potassium carbonate (40 mg) in water (0.25 ml), tetrabutylammonium hydrogen sulfate (32 mg) and a solution of iodomethyl methyl carbonate (43 mg) in dichloromethane (0.3 ml) and stirring was continued at 22° C. for 18 h. The mixture was partitioned between dichloromethane and water, the organic layer was dried, evaporated and the residue purified by flash chromatography (silica gel, ethyl acetate) to give the title compound (15 mg) as an off-white solid.

MS (ESI, m/z): 508.3 [(M+H)$^+$].

The invention claimed is:

1. A compound having the formula (Ia) or (Ib), or a pharmaceutically acceptable salt solvate, prodrug, tautomer, racemate, enantiomer, or diastereomer or mixture thereof,

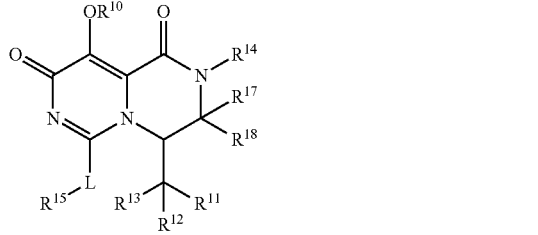

(Ia)

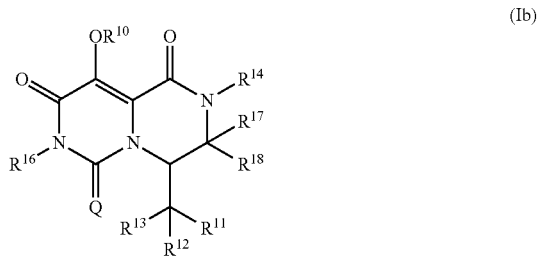

(Ib)

wherein
L is selected from $NR^L$, $N(R^L)C(O)$, $N(R^L)C(O)O$, $N(R^L)C(=NR^L)NR^L$, $C(O)N(R^L)$, $SO_2N(R^L)$, $N(R^L)SO_2O$, $C(O)O$, $OC(O)$, $OSO_2$, $S$, $SO$, $SO_2$ and a bond;

each $R^L$ is independently selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), and —$C_{1-4}$ alkyl-(optionally substituted aryl);

Q is selected from $NR^Q$, O and S;

$R^Q$ is selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), and —$C_{1-4}$ alkyl-(optionally substituted aryl);

$R^{10}$ is selected from —H, -(optionally substituted $C_{1-6}$ alkyl group) and —C(O)-(optionally substituted $C_{1-6}$ alkyl group);

$R^{11}$ is selected from —H, a —$C_{1-6}$ alkyl group, and a —$C_{1-6}$ alkyl group which is substituted by one or more halogen atoms;

$R^{12}$ and $R^{13}$ are each independently selected from a -(optionally substituted aryl or heteroaryl group which contains from 5 to 20 carbon atoms and optionally 1 to 4 heteroatoms selected from O, N and S);

or $R^{12}$ and $R^{13}$ are optionally joined together to form a group containing at least two carbo- or heterocyclic rings which are connected to each other via linking group Rc which is selected from the group consisting of a bond, —$CH_2$—, —C(O)—, —O—, —S—, —S(O)—, —N(H)—, —N(optionally substituted $C_{1-6}$ alkyl)-, —N(optionally substituted aryl)-, —C(O)NH—, —$CH_2$—$CH_2$—, —$CH_2$—O—, —$CH_2$—S—, —$CH_2$—N(H)—, —$CH_2$—N(optionally substituted $C_{1-6}$ alkyl)-, —$CH_2$—N(optionally substituted aryl)-, —$CH_2$—C(O)NH—, —$CH_2$—O—$CH_2$—, —$CH_2$—S—$CH_2$—, —$CH_2$—N(H)—$CH_2$—, —$CH_2$—N(optionally substituted $C_{1-6}$ alkyl)-$CH_2$—, —$CH_2$—N(optionally substituted aryl)-$CH_2$—, —$CH_2$—C(O)NH—$CH_2$— and —O—$CH_2$—O—;

$R^{14}$ is —H, -(optionally substituted $C_{1-6}$ alkyl), -(optionally substituted aryl), -(optionally substituted heterocycloalkyl), -(optionally substituted heteroaryl), —$C_{1-4}$ alkyl-(optionally substituted $C_{3-7}$ cycloalkyl), —$C_{1-4}$ alkyl-(optionally substituted aryl), —$C_{1-4}$ alkyl-(optionally substituted heterocycloalkyl), or —$C_{1-4}$ alkyl-(optionally substituted heteroaryl);

$R^{15}$ is selected from —H, —CN, -(optionally substituted $C_{1-6}$ alkyl), -(optionally substituted $C_{2-6}$ alkenyl), -(optionally substituted $C_{3-7}$ cycloalkyl), -(optionally substituted aryl), -(optionally substituted heteroaryl), —$C_{1-4}$ alkyl-(optionally substituted $C_{3-7}$ cycloalkyl), —$C_{1-4}$ alkyl-(optionally substituted aryl) and —$C_{1-4}$ alkyl-(optionally substituted heteroaryl);

$R^{16}$, $R^{17}$ and $R^{18}$ are each independently selected from —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl) and —$C_{1-4}$ alkyl-(optionally substituted aryl);

wherein the optional substituent(s) of the optionally substituted alkyl group is one or more substituents $R^a$, wherein each $R^a$ is independently selected from —C(O)—$C_{1-6}$ alkyl, -Hal, —$CF_3$, —CN, —COOR*, —OR*, —$(CH_2)_q$NR*R**, —C(O)—NR*R** and —NR*—C(O)—$C_{1-6}$ alkyl;

wherein the optional substituent(s) of the optionally substituted alkenyl group, optionally substituted cycloalkyl group, optionally substituted heterocycloalkyl group, optionally substituted aryl group, optionally substituted heteroaryl group is one or more substituents $R^b$, wherein each $R^b$ is independently selected from —$C_{1-6}$ alkyl, —C(O)—$C_{1-6}$ alkyl, -Hal, —$CF_3$, —CN, —COOR*, —OR*, —$(CH_2)_q$NR*R**, —C(O)—NR*R** and —NR*—C(O)—$C_{1-6}$ alkyl;

wherein the optional substituent(s) of the optionally substituted hydrocarbon group is one or more substituents $R^d$, wherein each $R^d$ is independently selected from —$C_{1-6}$ alkyl, —C(O)—$C_{1-6}$ alkyl, -Hal, —$CF_3$, —CN, —COOR*, —OR*, —$(CH_2)_q$NR*R**, —C(O)—NR*R** and —NR*—C(O)—$C_{1-6}$ alkyl;

wherein
R** is selected from —H, and —$C_{1-6}$ alkyl;
R* is selected from —H, —$C_{1-6}$ alkyl, and —$(CH_2CH_2O)_r$H;
r 1 to 3; and
q is 0 to 4 wherein the prodrug is a compound in which $R^{10}$ is replaced by $P(O)(O)OR^{19}$; $C(O)OR^{19}$; $C(O)R^{19}$; $C(R)_2$—$R^{19}$ or $R^{19}$; wherein $R^{19}$ is selected from $C_{5-10}$ aryl, $C_{1-6}$ alkylene-$C_{5-10}$ aryl, $C_{1-6}$ alkyl, $C_{1-6}$ alkylene (-O—$C_{1-6}$ alkyl)$_n$ (with n=1 to 30), $C_{1-6}$ alkylene-C(O)OR, $C_{5-10}$ arylene-C(O)OR, $C_{1-6}$ alkylene-O—C(O)OR and $C_{1-6}$ alkylene-O—C(O)R, and wherein the group R is H or $C_{1-6}$ alkyl.

2. The compound according to claim 1, being of the formula (Ia), or a pharmaceutically acceptable salt solvate, prodrug, tautomer, racemate, enantiomer, or diastereomer or mixture thereof,

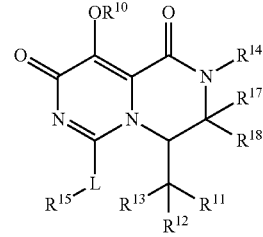

(Ia)

3. The compound according to claim 1, being of the formula (Ib), or a pharmaceutically acceptable salt solvate, prodrug, tautomer, racemate, enantiomer, or diastereomer or mixture thereof,

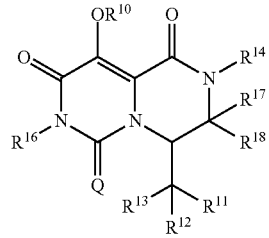

(Ib)

4. The compound according to claim 1, wherein $R^{12}$ and $R^{13}$ are joined together to form a group containing at least two carbo- or heterocyclic rings which are connected to each other via linking group Rc which is selected from the group consisting of a bond, —$CH_2$—, —C(O)—, —O—, —S—, —S(O)—, —N(H)—, —N(optionally substituted $C_{1-6}$ alkyl)-, —N(optionally substituted aryl)-, —C(O)NH—, —$CH_2$—$CH_2$—, —$CH_2$—O—, —$CH_2$—S—, —$CH_2$—N(H)—, —$CH_2$—N(optionally substituted $C_{1-6}$ alkyl)-, —$CH_2$—N(optionally substituted aryl)-, —$CH_2$—C(O)NH—, —$CH_2$—O—$CH_2$—, —$CH_2$—S—$CH_2$—, —$CH_2$—N(H)—$CH_2$—, —$CH_2$—N(optionally substituted $C_{1-6}$ alkyl)-$CH_2$—, —$CH_2$—N(optionally substituted aryl)-$CH_2$—, —$CH_2$—C(O)NH—$CH_2$— and —O—$CH_2$—O—.

5. The compound of formula (Ia) according to claim 1 wherein L is selected from $NR^L$, $N(R^L)C(O)$, $C(O)N(R^L)$, $SO_2N(R^L)$, $N(R^L)SO_2O$, C(O)O, OC(O), S, SO and $SO_2$;

wherein $R^L$ is —H or -(optionally substituted $C_{1-6}$ alkyl.

6. The compound according to claim 1, wherein $R^{10}$ is —H, —C(O)—$C_{1-6}$ alkyl group, wherein the alkyl group can be optionally substituted by one or more halogen atoms, or a —$C_{1-6}$ alkyl group which may optionally be substituted by one or more halogen atoms.

7. The compound according to claim 1, wherein is $R^{14}$ is selected from —H, -(optionally substituted $C_{1-6}$ alkyl), and -(optionally substituted aryl).

8. A pharmaceutical composition comprising:
a compound having the formula (Ia) or (Ib) as defined in claim 1, or a pharmaceutically acceptable salt, solvate, prodrug, tautomer, racemate, enantiomer, or diastereomer or mixture thereof, and one or more pharmaceutically acceptable excipient(s) and/or carrier(s).

9. A method of treating influenza; the method comprising administering to a patient in need thereof an effective amount of a compound having the formula (Ia) or (Ib) as defined in claim 1 or a pharmaceutically acceptable salt, solvate, prodrug, tautomer, racemate, enantiomer, or diastereomer or mixture thereof.

* * * * *